(12) United States Patent
Ridder et al.

(10) Patent No.: US 8,174,394 B2
(45) Date of Patent: *May 8, 2012

(54) SYSTEM FOR NONINVASIVE DETERMINATION OF ANALYTES IN TISSUE

(75) Inventors: Trent Ridder, Tucson, AZ (US); Ben ver Steeg, Redlands, CA (US); Mike Mills, Tijeras, NM (US); Bentley Laaksonen, Albuquerque, NM (US); James McNally, Albuquerque, NM (US); John Maynard, Albuquerque, NM (US); Russell Abbink, Sandia Park, NM (US)

(73) Assignee: TruTouch Technologies, Inc., Albuquerque, NM (US)

( * ) Notice: Subject to any disclaimer, the term of this patent is extended or adjusted under 35 U.S.C. 154(b) by 376 days.
This patent is subject to a terminal disclaimer.

(21) Appl. No.: 12/562,050

(22) Filed: Sep. 17, 2009

(65) Prior Publication Data

US 2010/0010325 A1    Jan. 14, 2010

Related U.S. Application Data

(63) Continuation-in-part of application No. 11/515,565, filed on Sep. 5, 2006, now Pat. No. 7,616,123, which is a continuation-in-part of application No. 11/305,964, filed on Dec. 19, 2005, now Pat. No. 7,756,558, which is a continuation-in-part of application No. 10/852,415, filed on May 24, 2004, now Pat. No. 7,403,804, which is a continuation-in-part of application No. 09/832,585, filed on Apr. 11, 2001, now Pat. No. 6,574,490, which is a continuation-in-part of application No. 10/281,576, filed on Oct. 28, 2002, now Pat. No. 7,202,091, which is a continuation-in-part of application No. 10/378,237, filed on Mar. 3, 2003, now Pat. No. 6,865,408, which is a continuation-in-part of application No. 10/753,506, filed on Jan. 8, 2004, now Pat. No. 7,016,713.

(60) Provisional application No. 61/147,107, filed on Jan. 25, 2009.

(51) Int. Cl.
*G08B 13/14* (2006.01)
*A61B 5/1455* (2006.01)
(52) U.S. Cl. ............... 340/573.1; 340/576; 600/310
(58) Field of Classification Search .............. 340/573.1, 340/573.4, 573.5, 573.7, 552, 554, 555, 557, 340/567, 575, 576, 5.2, 5.53, 5.83; 600/310, 600/312, 316, 322, 473, 476; 702/104; 250/339.08, 250/339.09, 573
See application file for complete search history.

(56) References Cited

U.S. PATENT DOCUMENTS 4,592,443 A    6/1986   Simon
(Continued)

OTHER PUBLICATIONS

Miller et. al. in "Minimally invasive spectroscopic system for intraocular drug detection", Journal of Biomedical Optics 7(1), 27-33 (2002).

(Continued)

*Primary Examiner* — Van T. Trieu
(74) *Attorney, Agent, or Firm* — V. Gerald Grafe

(57) ABSTRACT

An apparatus and method for noninvasive determination of analyte properties of human tissue by quantitative infrared spectroscopy to clinically relevant levels of precision and accuracy. The system includes subsystems optimized to contend with the complexities of the tissue spectrum, high signal-to-noise ratio and photometric accuracy requirements, tissue sampling errors, calibration maintenance problems, and calibration transfer problems. The subsystems can include an illumination/modulation subsystem, a tissue sampling subsystem, a data acquisition subsystem, a computing subsystem, and a calibration subsystem. The invention can provide analyte property determination and identity determination or verification from the same spectroscopic information, making unauthorized use or misleading results less likely than in systems that use separate analyte and identity determinations. The invention can be used to control and monitor individuals accessing controlled environments.

34 Claims, 41 Drawing Sheets

U.S. PATENT DOCUMENTS

| | | | |
|---|---|---|---|
| 4,699,149 A | 10/1987 | Rice | |
| 4,703,474 A | 10/1987 | Foschini et al. | |
| 4,738,333 A | 4/1988 | Collier | |
| 4,975,581 A | 12/1990 | Robinson et al. | |
| 4,996,161 A | 2/1991 | Conners | |
| 5,055,268 A | 10/1991 | Martin | |
| 5,224,566 A | 7/1993 | Stepanian | |
| 5,348,002 A * | 9/1994 | Caro | 600/310 |
| 5,348,003 A | 9/1994 | Caro | |
| 5,426,415 A | 6/1995 | Prachar | |
| 5,638,816 A | 6/1997 | Kiani-Azarbayiany | |
| 5,655,530 A | 8/1997 | Messerschmidt | |
| 5,696,582 A | 12/1997 | Barwald | |
| 5,743,262 A | 4/1998 | Lepper et al. | |
| 5,743,349 A | 4/1998 | Steinberg | |
| 5,747,806 A | 5/1998 | Khalil | |
| 5,823,951 A | 10/1998 | Messerschmidt | |
| 5,830,112 A | 11/1998 | Wang et al. | |
| 5,830,132 A | 11/1998 | Robinson et al. | |
| 5,835,213 A | 11/1998 | Curbelo | |
| 5,860,919 A | 1/1999 | Kiani-Azarbayiany | |
| 5,907,407 A | 5/1999 | Atkinson | |
| 5,914,780 A | 6/1999 | Turner et al. | |
| 5,923,422 A | 7/1999 | Keens et al. | |
| 5,945,676 A | 8/1999 | Khalil | |
| 5,953,477 A | 9/1999 | Watch et al. | |
| 5,963,322 A | 10/1999 | Rapp et al. | |
| 6,006,001 A | 12/1999 | Alfano et al. | |
| 6,040,194 A | 3/2000 | Chick | |
| 6,040,578 A | 3/2000 | Malin | |
| 6,067,167 A | 5/2000 | Atkinson | |
| 6,110,522 A | 8/2000 | Lepper et al. | |
| 6,151,516 A | 11/2000 | Kiani-Azarbayiany | |
| 6,152,876 A | 11/2000 | Robinson | |
| 6,157,041 A * | 12/2000 | Thomas et al. | 250/573 |
| 6,219,565 B1 | 4/2001 | Cupp et al. | |
| 6,223,063 B1 | 4/2001 | Chaiken | |
| 6,229,908 B1 | 5/2001 | Edmonds | |
| 6,278,889 B1 | 8/2001 | Robinson | |
| 6,411,373 B1 | 6/2002 | Garside et al. | |
| 6,415,167 B1 | 7/2002 | Blank | |
| 6,424,848 B1 | 7/2002 | Berman | |
| 6,441,388 B1 | 8/2002 | Thomas | |
| 6,493,566 B1 | 12/2002 | Ruchti | |
| 6,512,937 B2 | 1/2003 | Blank | |
| 6,528,809 B1 | 3/2003 | Thomas | |
| 6,559,947 B1 | 5/2003 | Turner | |
| 6,560,352 B2 | 5/2003 | Rowe | |
| 6,574,490 B2 | 6/2003 | Abbink et al. | |
| 6,574,501 B2 | 6/2003 | Lambert | |
| 6,587,196 B1 | 7/2003 | Stippick | |
| 6,587,199 B1 | 7/2003 | Luu | |
| 6,622,032 B1 | 9/2003 | Robinson et al. | |
| 6,628,809 B1 | 9/2003 | Thomas | |
| 6,640,117 B2 | 10/2003 | Makarewicz | |
| 6,654,125 B2 | 11/2003 | Maynard | |
| 6,654,620 B2 * | 11/2003 | Wu et al. | 600/310 |
| 6,678,541 B1 | 1/2004 | Durkin et al. | |
| 6,684,099 B2 | 1/2004 | Ridder et al. | |
| 6,687,521 B2 | 2/2004 | Sato | |
| 6,748,301 B1 | 6/2004 | Ryu | |
| 6,748,792 B1 | 6/2004 | Freund | |
| 6,816,241 B2 | 11/2004 | Grubisic | |
| 6,816,605 B2 | 11/2004 | Rowe | |
| 6,862,091 B2 | 3/2005 | Johnson | |
| 6,864,978 B1 | 3/2005 | Hazen | |
| 6,865,408 B1 | 3/2005 | Abbink et al. | |
| 6,870,620 B2 | 3/2005 | Faupel et al. | |
| 6,898,451 B2 * | 5/2005 | Wuori | 600/322 |
| 6,931,268 B1 | 8/2005 | Kiani-Azarbayiany | |
| 6,956,484 B2 | 10/2005 | Crespo | |
| 6,956,649 B2 | 10/2005 | Acosta | |
| 6,983,176 B2 | 1/2006 | Gardner | |
| 7,016,713 B2 | 3/2006 | Gardner | |
| 7,038,774 B2 | 5/2006 | Hazen | |
| 7,043,288 B2 | 5/2006 | Davis, III et al. | |
| 7,092,832 B2 | 8/2006 | Brown | |
| 7,098,037 B2 | 8/2006 | Haas | |
| 7,133,710 B2 | 11/2006 | Acosta | |
| 7,139,076 B1 | 11/2006 | Marbach | |
| 7,147,153 B2 | 12/2006 | Rowe | |
| 7,167,735 B2 | 1/2007 | Uchida | |
| 7,183,102 B2 | 2/2007 | Monfre | |
| 7,194,369 B2 * | 3/2007 | Lundstedt et al. | 702/104 |
| 7,202,091 B2 | 4/2007 | Jones | |
| 7,203,345 B2 | 4/2007 | Rowe | |
| 7,206,623 B2 | 4/2007 | Blank | |
| 7,233,816 B2 | 6/2007 | Blank | |
| 7,263,213 B2 | 8/2007 | Rowe | |
| 7,299,080 B2 | 11/2007 | Acosta | |
| 7,333,843 B2 | 2/2008 | Monfre | |
| 7,347,365 B2 | 3/2008 | Rowe | |
| 7,386,152 B2 | 6/2008 | Rowe | |
| 7,398,119 B2 | 7/2008 | Lambert | |
| 7,403,804 B2 | 7/2008 | Ridder et al. | |
| 7,460,696 B2 | 12/2008 | Rowe | |
| 7,505,801 B2 | 3/2009 | Monfre | |
| 7,508,965 B2 | 3/2009 | Rowe | |
| 7,509,153 B2 | 3/2009 | Blank | |
| 7,519,406 B2 | 4/2009 | Blank | |
| 7,539,330 B2 | 5/2009 | Rowe | |
| 7,545,963 B2 | 6/2009 | Rowe | |
| 7,606,608 B2 | 10/2009 | Blank | |
| 7,613,504 B2 | 11/2009 | Rowe | |
| 7,616,123 B2 | 11/2009 | Ridder et al. | |
| 7,620,212 B1 | 11/2009 | Allen | |
| 7,627,151 B2 | 12/2009 | Rowe | |
| 7,756,558 B2 | 7/2010 | Ridder et al. | |
| 7,848,605 B2 | 12/2010 | Ridder et al. | |
| 7,889,349 B2 | 2/2011 | Ridder et al. | |
| 2003/0032064 A1 * | 2/2003 | Soller et al. | 435/7.1 |
| 2003/0163710 A1 | 8/2003 | Ortiz | |
| 2004/0204868 A1 | 10/2004 | Maynard | |
| 2005/0130321 A1 | 6/2005 | Nicholson | |
| 2005/0230175 A1 | 10/2005 | Brown | |
| 2005/0261560 A1 | 11/2005 | Ridder et al. | |
| 2006/0002597 A1 | 1/2006 | Rowe | |
| 2006/0002598 A1 | 1/2006 | Rowe | |
| 2006/0062438 A1 | 3/2006 | Rowe | |
| 2006/0110015 A1 | 5/2006 | Rowe | |
| 2006/0167349 A1 | 7/2006 | Gardner | |
| 2006/0173256 A1 | 8/2006 | Ridder et al. | |
| 2006/0202028 A1 | 9/2006 | Rowe | |
| 2006/0210120 A1 | 9/2006 | Rowe | |
| 2006/0244947 A1 | 11/2006 | Rowe | |
| 2006/0274921 A1 | 12/2006 | Rowe | |
| 2007/0030475 A1 | 2/2007 | Rowe | |
| 2007/0073118 A1 | 3/2007 | Ridder et al. | |
| 2007/0142720 A1 | 6/2007 | Ridder et al. | |
| 2007/0230754 A1 | 10/2007 | Jain | |
| 2007/0239992 A1 | 10/2007 | White | |
| 2008/0025579 A1 | 1/2008 | Sidlauskas | |
| 2008/0025580 A1 | 1/2008 | Sidlauskas | |
| 2008/0192988 A1 | 8/2008 | Uludag | |
| 2008/0208018 A1 | 8/2008 | Ridder et al. | |
| 2008/0232653 A1 | 9/2008 | Rowe | |
| 2008/0297788 A1 | 12/2008 | Rowe | |
| 2008/0298649 A1 | 12/2008 | Ennis | |
| 2008/0304712 A1 | 12/2008 | Rowe | |
| 2008/0319286 A1 | 12/2008 | Ridder et al. | |
| 2009/0046903 A1 | 2/2009 | Corcoran | |
| 2009/0074255 A1 | 3/2009 | Holm | |
| 2009/0080709 A1 | 3/2009 | Rowe | |
| 2009/0092290 A1 | 4/2009 | Rowe | |
| 2009/0148005 A1 | 6/2009 | Rowe | |
| 2009/0234204 A1 | 9/2009 | Ridder et al. | |
| 2009/0245591 A1 | 10/2009 | Rowe | |
| 2009/0247840 A1 | 10/2009 | Blank | |
| 2010/0010325 A1 | 1/2010 | Ridder et al. | |
| 2011/0178420 A1 | 7/2011 | Ridder et al. | |

OTHER PUBLICATIONS

Brault, "New Approach to High-Precision Fourier Transform Spectrometer Design," Applied Optics, vol. 35, No. 16, Jun. 1, 1996, pp. 2891-2896.

Brasunas and Cusman, "Uniform Time-Sampling Fourier Transform Spectroscopy," Applied Optics, vol. 36, No. 10, Apr. 1, 1997, pp. 2206-2210.

* cited by examiner

SYSTEM FOR NONINVASIVE DETERMINATION OF ANALYTES IN TISSUE

CROSS REFERENCES TO RELATED APPLICATIONS

This application claims priority under 35 U.S.C §120 as a continuation-in-part of U.S. patent application Ser. No. 11/515,565, titled "Apparatus and Method for Noninvasively Monitoring for the Presence of Alcohol or Substances of Abuse in Controlled Environments," filed Sep. 5, 2006, now U.S. Pat. No. 7,616,123, which application was a continuation-in-part of U.S. patent application Ser. No. 11/305,964, titled "Apparatus and Methods for Mitigating the Effects of Foreign Interferents on Analyte Measurements in Spectroscopy," filed Dec. 19, 2005, now U.S. Pat. No. 7,756,558, which application was a continuation-in-part of U.S. patent application Ser. No. 10/852,415, titled "Noninvasive determination of alcohol in tissue," filed May 24, 2004, now U.S. Pat. No. 7,403,804, which application was a continuation-in-part of U.S. patent application Ser. No. 09/832,585, titled "System For Non-Invasive Measurement Of Glucose In Humans," filed Apr. 11, 2001, now U.S. Pat. No. 6,574,490, and of U.S. patent application Ser. No. 10/281,576, titled "Optically Similar Reference Samples", filed Oct. 28, 2002, now U.S. Pat. No. 7,202,091, and of U.S. patent application Ser. No. 10/378,237, titled "System For Non-Invasive Measurement Of Glucose In Humans," filed Mar. 3, 2003, now U.S. Pat. No. 6,865,408, and of U.S. patent application Ser. No. 10/753,506, "Noninvasive Determination of Direction and Rate of Change of an Analyte," filed Jan. 8, 2004, now U.S. Pat. No. 7,016,713; each of the preceding applications is incorporated herein by reference. This application claims the benefit of U.S. Provisional Application No. 61/147,107, titled "System for Noninvasive Determination of Alcohol in Tissue," filed Jan. 25, 2009, which is incorporated herein by reference.

TECHNICAL FIELD

The present invention relates to a quantitative spectroscopy system for measuring the presence or concentration of alcohol, alcohol byproducts, alcohol adducts, or substances of abuse utilizing noninvasive techniques in combination with multivariate analysis. The present invention further relates to noninvasive monitoring for the presence or concentration of alcohol or other substances in individuals in probation/corrections, alcohol treatment centers, and restricted access environments, and more specifically to spectroscopic methods and apparatuses for detecting the presence or concentration of alcohol or substances of abuse in individuals in any of a variety of controlled environments.

BACKGROUND OF THE INVENTION

Alcohol abuse is a national problem that extends into virtually all aspects of society. Current practice for alcohol measurements to detect alcohol abuse is based upon either blood measurements or breath testing. Blood measurements define the gold standard for determining alcohol intoxication levels. However, blood measurements require either a venous or capillary sample and involve significant handling precautions in order to minimize health risks. Once extracted, the blood sample must be properly labeled and transported to a clinical laboratory or other suitable location where a clinical gas chromatograph is typically used to measure the blood alcohol level. Due to the invasiveness of the procedure and the amount of sample handling involved, blood alcohol measurements are usually limited to critical situations such as for traffic accidents, violations where the suspect requests this type of test, and accidents where injuries are involved.

Because it is less invasive, breath testing is more commonly encountered in the field. In breath testing, the subject must expire air into the instrument for a sufficient time and volume to achieve a stable breath flow that originates from the alveoli deep within the lungs. The device then measures the alcohol content in the air, which is related to blood alcohol through a breath-blood partition coefficient. The blood-breath partition coefficient used in the United States is 2100 (implied units of mg EtOH/dL blood per mg EtOH/dL air) and varies between 1900 and 2400 in other nations. The variability in the partition coefficient is due to the fact that it is highly subject dependent. In other words, each subject will have a partition coefficient in the 1900 to 2400 range that depends on his or her physiology. Since knowledge of each subject's partition coefficient is unavailable in field applications, each nation assumes a single partition coefficient value that is globally applied to all measurements. In the U.S., defendants in DUI cases often use the globally applied partition coefficient as an argument to impede prosecution.

Breath measurements have additional limitations. First, the presence of "mouth alcohol" can falsely elevate the breath alcohol measurement. This necessitates a 15-minute waiting period prior to making a measurement in order to ensure that no mouth alcohol is present. For a similar reason, a 15 minute delay is required for individuals who are observed to burp or vomit. A delay of 10 minutes or more is often required between breath measurements to allow the instrument to return to equilibrium with the ambient air and zero alcohol levels. In addition, the accuracy of breath alcohol measurements is sensitive to numerous physiological and environmental factors.

Multiple government agencies, and society in general, seek noninvasive alternatives to blood and breath alcohol measurements. Quantitative spectroscopy offers the potential for a completely noninvasive alcohol measurement that is not sensitive to the limitations of the current measurement methodologies. While noninvasive determination of biological attributes by quantitative spectroscopy has been found to be highly desirable, it has been very difficult to accomplish. Attribute properties of interest include, as examples, analyte presence, analyte concentration (e.g., alcohol concentration), direction of change of an analyte concentration, rate of change of an analyte concentration, disease presence (e.g., alcoholism), disease state, and combinations and subsets thereof. Noninvasive measurements via quantitative spectroscopy are desirable because they are painless, do not require a fluid draw from the body, carry little risk of contamination or infection, do not generate any hazardous waste, and can have short measurement times.

Several systems have been proposed for the noninvasive determination of attribute properties of biological tissue. These systems have included technologies incorporating polarimetry, mid-infrared spectroscopy, Raman spectroscopy, Kromoscopy, fluorescence spectroscopy, nuclear magnetic resonance spectroscopy, radio-frequency spectroscopy, ultrasound, transdermal measurements, photo-acoustic spectroscopy, and near-infrared spectroscopy. However, these systems have not replaced direct and invasive measurements.

As an example, Robinson et al. in U.S. Pat. No. 4,975,581 disclose a method and apparatus for measuring a characteristic of unknown value in a biological sample using infrared spectroscopy in conjunction with a multivariate model that is empirically derived from a set of spectra of biological samples of known characteristic values. The above-mentioned characteristic is generally the concentration of an analyte, such as alcohol, but also can be any chemical or physical property of the sample. The method of Robinson et al. involves a two-step process that includes both calibration and prediction steps.

In the calibration step, the infrared light is coupled to calibration samples of known characteristic values so that there is attenuation of at least several wavelengths of the infrared radiation as a function of the various components and analytes comprising the sample with known characteristic value. The infrared light is coupled to the sample by passing the light through the sample or by reflecting the light off the sample. Absorption of the infrared light by the sample causes intensity variations of the light that are a function of the wavelength of the light. The resulting intensity variations at a minimum of several wavelengths are measured for the set of calibration samples of known characteristic values. Original or transformed intensity variations are then empirically related to the known characteristics of the calibration samples using multivariate algorithms to obtain a multivariate calibration model. The model preferably accounts for subject variability, instrument variability, and environment variability.

In the prediction step, the infrared light is coupled to a sample of unknown characteristic value, and a multivariate calibration model is applied to the original or transformed intensity variations of the appropriate wavelengths of light measured from this unknown sample. The result of the prediction step is the estimated value of the characteristic of the unknown sample. The disclosure of Robinson et al. is incorporated herein by reference.

A further method of building a calibration model and using such model for prediction of analytes and/or attributes of tissue is disclosed in commonly assigned U.S. Pat. No. 6,157,041 to Thomas et al., titled "Method and Apparatus for Tailoring Spectrographic Calibration Models," the disclosure of which is incorporated herein by reference. In U.S. Pat. No. 5,830,112, Robinson describes a general method of robust sampling of tissue for noninvasive analyte measurement. The sampling method utilizes a tissue-sampling accessory that is pathlength optimized by spectral region for measuring an analyte, such as alcohol. The patent discloses several types of spectrometers for measuring the spectrum of the tissue from 400 to 2500 nm, including acousto-optical tunable filters, discrete wavelength spectrometers, filters, grating spectrometers and FTIR spectrometers. The disclosure of Robinson is incorporated hereby reference.

Spectroscopic measurements offer promise for completely noninvasive alcohol measurements in people in controlled environments. In U.S. Pat. No. 5,743,349, titled "Non-invasive optical blood alcohol concentration reader and vehicle ignition interlock system and method", Steinberg discloses a vehicle ignition interlock that incorporates a spectroscopic means for noninvasively measuring blood alcohol concentration. Steinberg does not disclose any means for verifying the identity of the tested individual. Furthermore, Steinberg discloses the measurement of electromagnetic radiation in the 250 to 3000 nm wavelength range by introducing radiation to a finger and measuring the light exiting the opposite side of the finger. Such transmission approaches, while potentially feasible in the visible region (400 to 800 nm), are limited by the strong absorption of water (water is a major component of the tissue) in the near- and mid-infrared regions (>800 nm). For tissue samples greater than a few millimeters in thickness, the absorption of water results in virtually no measurable radiation exiting the opposite side of the sample. Consequently, little if any radiation remains for subsequent measurement of alcohol concentration.

In U.S. Pat. No. 6,229,908, titled "Driver Alcohol Ignition Interlock", Edmonds and Hopta disclose an ignition interlock incorporating a spectroscopic alcohol measurement of the finger combined with a means for generating a finger print image. The finger print image is intended to identify the operator in order to ensure that the alcohol measurement was acquired from the prospective driver and not a passenger. Similar to existing breath-based interlocks, the finger print image is obtained from a measurement that is distinct from the spectroscopic measurement, thereby yielding potential for circumventing the interlock. Further, the method disclosed by Edmonds and Hopta relies on automated fingerprint reading, a technology which has demonstrated performance shortcomings.

Therefore, although there has been substantial work conducted in attempting to produce commercially viable noninvasive near-infrared spectroscopy-based systems for determination of biological attribute properties, including the presence of alcohol, or substances of abuse, no such device is presently available. It is believed that prior art systems discussed above have failed for one or more reasons to fully meet the challenges imposed by the spectral characteristics of tissue which make the design of a noninvasive measurement system a formidable task. Thus, there is a substantial need for a commercially viable device which incorporates subsystems and methods with sufficient accuracy and precision to make clinically relevant determinations of biological attribute properties in human tissue.

SUMMARY OF THE INVENTION

The present invention provides an effective apparatus and method for monitoring for the presence or concentration of alcohol or substances of abuse in controlled environments, and is considered in terms of three primary components. FIG. 1 is a schematic illustration of an embodiment of such an apparatus and method. A first component is a system 1 that can measure the presence or concentration of alcohol or substance of abuse in an individual. A second component 2 is a system that can verify or determine that the measurement was obtained from a specific individual or a member of a specific group of individuals. A third component 3 is a system that performs an action based upon the alcohol or substance of abuse measurement and identity verification/determination results, where the action can be dependent on and vary according to the specific environment under consideration. For example, when alcohol is detected in an individual housed in a residential treatment center, the action performed by the present invention can be documentation of the positive alcohol test followed by notification of a facility administrator. In other embodiments, such as those intended to control access to secure facilities, the present invention can deny entry to any individual that either failed the alcohol/substance of abuse measurement or was determined to be unauthorized to enter by the identity verification or determination measurement. The present invention links the first two components of the disclosed apparatuses and methods via a single spectroscopic measurement, which significantly reduces methods for circumvention. For demonstrative purposes the discussion herein generally refers to infrared and near-infrared spectroscopic measurements, however, visible (UV-vis), Raman, and fluorescence spectroscopic measurements are also feasible techniques for the present invention, Absorption spectroscopy is a generally known analytical method. In some forms, absorption spectroscopy measures the electromagnetic radiation (typical wavelength range of 0.3-25 μm) that a substance absorbs at various wavelengths, though other methods measure other effects a substance has on incident light. Absorption phenomena can be related to molecular vibrations and shifts in energy levels of individual atoms or electrons within a molecule. These phenomena cause the absorbing molecule or atom to switch to a higher energy state. Absorption occurs most frequently in limited ranges of wavelengths that are based upon the molecular structure of the species present in the measured sample. Thus, for light passing through a substance at several wavelengths, the substance will absorb a greater percentage of photons at certain wavelengths than it will at others.

At the molecular level, many primary vibrational transitions occur in the mid-infrared wavelength region (i.e., wavelengths between 2.5-6 μm). However, for some measurements, use of the mid-infrared region can be problematic because molecules with strong absorbance properties (e.g., water) can result in the total absorption of virtually all light introduced to the sample being measured. The problem can often be overcome through the use of shorter wavelengths (typically in the near infrared region of 0.7-2.5 μm) where weaker overtones and combinations of the mid-infrared vibrations exist. Thus, the near-infrared region can be employed in such situations as it preserves the qualitative and quantitative properties of mid-infrared measurements while helping to alleviate the problem of total light absorption.

As mentioned above, alcohol and other analytes absorb light at multiple wavelengths in both the mid- and near-infrared range. Due to the overlapping nature of these absorption bands, reliable analyte measurements can be very difficult if only a single wavelength were used for analysis. Thus, analysis of spectral data can incorporate absorption characteristics at several wavelengths, which enables sensitive and selective measurements of the desired analytes. In multi-wavelength spectroscopy, multivariate analysis techniques can be used to empirically determine the relationship between measured spectra and a property of interest (e.g., analyte concentration).

Advances in optical materials and multivariate algorithms over the last several decades have created the potential for expanding spectroscopic measurements into new areas of interest. One such area is noninvasive measurements of analytes in skin. Human skin, as depicted in FIG. 2, is a multi-layer system comprised of the epidermis, dermis, and subcutaneous layers. Each layer has different physiological and chemical characteristics that influence its relative contribution to spectroscopic measurements of tissue. For example, the subcutaneous layer is largely comprised of lipids that are typically absent in other tissue layers. In contrast, the dermal layer is composed primarily of water and collagen. As a result, spectroscopic measurements of the present invention inherently contain contributions of the analytes within each tissue layer and therefore can provide insight into both the chemical composition and the structure of the tissue.

In many cases the complexity of the spectroscopic tissue measurements requires application of multivariate models to elucidate the property of interest (e.g., alcohol concentration or biometric identification/verification). In some applications, such as the apparatuses and methods of the present invention, the inherent spectral complexity can be advantageous. Due to natural physiological variation in skin, people have different tissue properties (e.g., dermal hydration, collagen densities, and tissue layer thicknesses). A spectroscopic measurement can capture the inter-subject differences, which enables discrimination between individuals. In other words, the noninvasive spectroscopic signal of the present invention simultaneously enables both analyte (alcohol or substances of abuse) and biometric measurements thereby providing and integrally linking two of the three components of an effective method or apparatus for monitoring for the presence or concentration of alcohol or a substance of abuse in a controlled environment.

The third component of the embodiments of the present invention is a system that combines the analyte and identity verification measurements, stores the results, and performs an action based upon the results. For example, when alcohol is detected in an individual housed in a residential treatment center, the action performed by the present invention can include documentation of the positive alcohol test and notification of a facility administrator. In other embodiments, such as those intended to control access to secure facilities, the present invention can deny entry to any individual that either failed the alcohol/substance of abuse measurement or was determined to be unauthorized to enter by the identity measurement.

The present invention further relates to a quantitative spectroscopy system for measuring the presence or concentration of alcohol, alcohol byproducts, alcohol adducts, or substances of abuse utilizing noninvasive techniques in combination with multivariate analysis. The present system overcomes the challenges posed by the spectral characteristics of tissue by incorporating a design that includes, in some embodiments, five optimized subsystems. The design contends with the complexities of the tissue spectrum, high signal-to-noise ratio and photometric accuracy requirements, tissue sampling errors, calibration maintenance problems, calibration transfer problems plus a host of other issues. The five subsystems include an illumination/modulation subsystem, a tissue sampling subsystem, a data acquisition subsystem, a computing subsystem, and a calibration subsystem.

The present invention further includes apparatus and methods that allow for implementation and integration of each of these subsystems in order to maximize the net attribute signal-to-noise ratio. The net attribute signal is the portion of the near-infrared spectrum that is specific for the attribute of interest because it is orthogonal to all other sources of spectral variance. The orthogonal nature of the net attribute signal makes it perpendicular to the space defined by any interfering species and as a result, the net attribute signal is uncorrelated to these sources of variance. The net attribute signal-to-noise ratio is directly related to the accuracy and precision of the present invention for noninvasive determination of the attribute by quantitative near-infrared spectroscopy.

The present invention can use near-infrared radiation for analysis. Radiation in the wavelength range of 1.0 to 2.5 microns (or wavenumber range of 10,000 to 4,000 $cm^{-1}$) can be suitable for making some noninvasive measurements because such radiation has acceptable specificity for a number of analytes, including alcohol, along with tissue optical penetration depths of up to 5 millimeters with acceptable absorbance characteristics. In the 1.0 to 2.5 micron spectral region, the large number of optically active substances that make up the tissue complicate the measurement of any given substance due to the overlapped nature of their absorbance spectra. Multivariate analysis techniques can be used to resolve these overlapped spectra such that accurate measurements of the substance of interest can be achieved. Multivariate analysis techniques, however, can require that multivariate calibrations remain robust over time (calibration maintenance) and be applicable to multiple instruments (calibration transfer). Other wavelength regions, such as the visible and infrared, can also be suitable for the present invention.

The present invention uses a multidisciplinary approach to the design of a spectroscopic instrument that incorporates an understanding of the instrument subsystems, tissue physiology, multivariate analysis, near-infrared spectroscopy and overall system operation. Further, the interactions between the subsystems have been analyzed so that the behavior and requirements for the entire noninvasive measurement device are well understood and result in a design for a commercial instrument that can make noninvasive measurements with sufficient accuracy and precision at a price and size that is commercially viable.

The subsystems of the noninvasive monitor are highly optimized to provide reproducible and, preferably, uniform radiance of the tissue, low tissue sampling error, depth targeting of the tissue layers that contain the property of interest, efficient collection of diffuse reflectance spectra from the tissue, high optical throughput, high photometric accuracy, large dynamic range, excellent thermal stability, effective calibration maintenance, effective calibration transfer, built-in quality control, and ease-of-use.

The advantages and features of novelty that characterize the present invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter in which there are illustrated and described preferred embodiments of the present invention.

Detailed embodiments of the present invention are disclosed herein. However, it is to be understood that the disclosed embodiments are merely exemplary of the present invention that can be embodied in various systems. Therefore, specific details disclosed herein are not to be interpreted as limiting, but rather as a basis for the claims and as a representative basis for teaching one of skill in the art to variously practice the invention.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
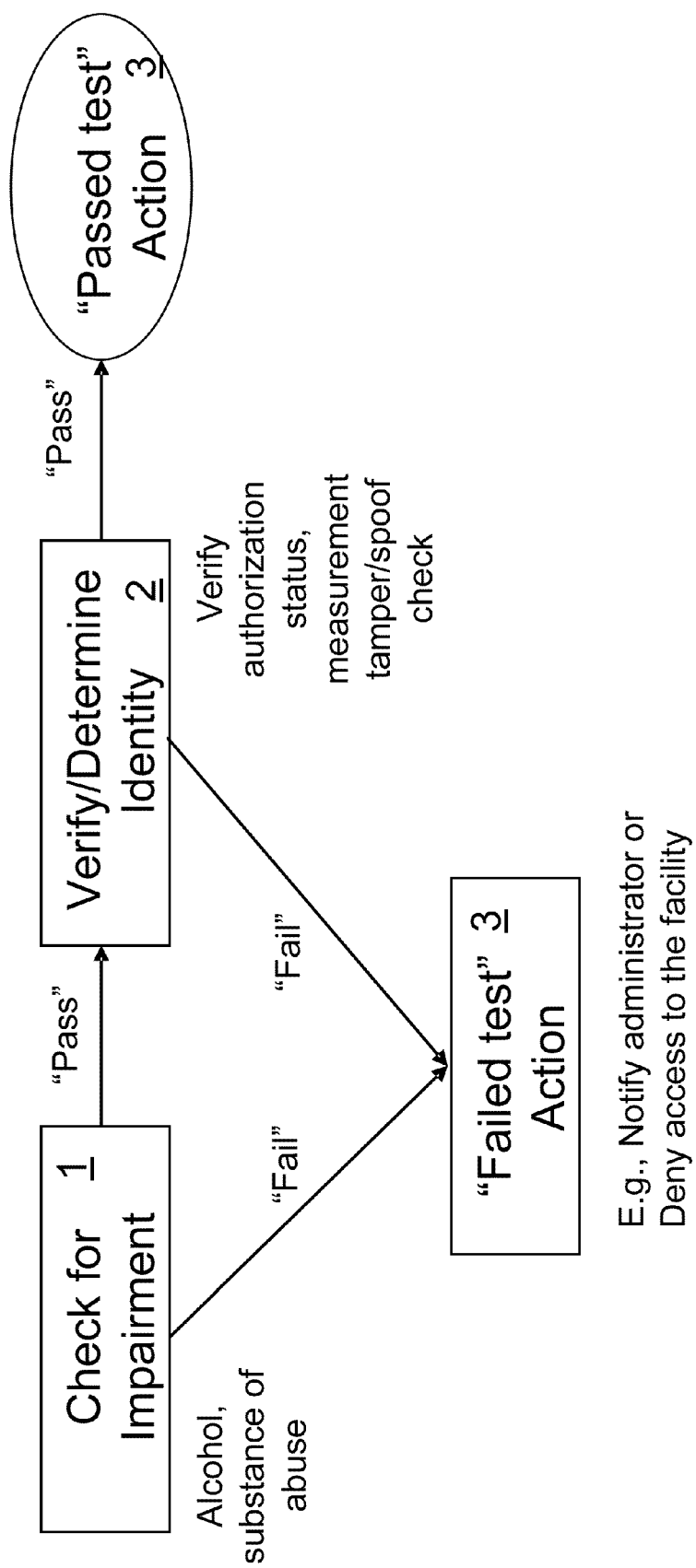
FIG. 1 is a schematic illustration of an embodiment of the present invention.

In U.S. Pat. No. 7,403,804, titled "Noninvasive determination of alcohol in tissue," Ridder et al. disclose a method for the noninvasive measurement of alcohol based on spectroscopic techniques that provides an alternative to the current blood, breath, urine, saliva, and transdermal methods. The device requires passive contact between the noninvasive device and a tissue surface such as a finger, forearm, palm, or earlobe in order to measure the alcohol concentration in the tissue. The alcohol measurement described in Ridder typically requires only a short period of time (i.e. 1 minute) and thus is suitable for use the environments disclosed in the present invention.

In U.S. Pat. No. 6,628,809, titled "Apparatus and method for identification of individuals by near-infrared spectrum", and in U.S. Pat. No. 6,560,352, titled "Apparatus and method of biometric identification or verification of individuals using optical spectroscopy", both incorporated herein by reference, Rowe et. al. disclose spectroscopic methods for determining the identity or verifying the identity of an individual using spectroscopic measurements of tissue. Such spectroscopic methods provide an alternative to existing fingerprint, voice recognition, video recognition, and bodily feature identification for the controlled environments contemplated with the present invention.

An advantage of the present invention is that the spectroscopic signal used to measure alcohol concentration, such as that described by Ridder, also contains chemical and structural biometric information of the individual being measured as described by Rowe. As the spectroscopic signal inherently contains both alcohol and biometric information, the two measurements can be integrally linked, which results in a more robust measurement that is not susceptible to many circumvention approaches. The spectroscopic measurement of analytes can also be combined with other identification approaches (e.g., to produce a system that identifies an individual and indicates the presence or concentration of alcohol or a substance of abuse), and with other systems alone (e.g., to prevent admission of any intoxicated or drug-using person to a facility regardless of identity) or with identification (e.g., to limit facility admission to authorized individuals who are not intoxicated).

Another aspect of the present invention is the ability to incorporate the measurement of analytes other than alcohol into the measurement system. For example, spectroscopic methods, such as those described by Miller et. al. in "Minimally invasive spectroscopic system for intraocular drug detection", Journal of Biomedical Optics 7(1), 27-33, have been applied to the detection and quantification of substances of abuse. As such the noninvasive spectroscopic measurement described in Ridder will contain the spectroscopic signals of substances of abuse if present within the measured tissue. From the perspective of the present invention, methods based upon the combination of noninvasive spectroscopic measurements of alcohol or substances of abuse with an explicitly linked spectroscopic biometric measurement represent a significant advantage relative to existing approaches.

For the purposes of this invention, the term "analyte concentration" generally refers to the concentration of an analyte, such as alcohol. The term "analyte property" includes analyte concentration and other properties, such as the presence or absence of the analyte or the direction or rate of change of the analyte concentration, which can be measured in conjunction with or instead of the analyte concentration. While the term "analyte" generally refers to alcohol, other chemicals, particularly substances of abuse and alcohol byproducts, can also be determined with the present invention. The term "alcohol" is used as an example analyte of interest; the term is intended to include ethanol, methanol, ethyl glycol or any other chemical commonly referred to as alcohol. For the purposes of this invention, the term "alcohol byproducts" includes the adducts and byproducts of the metabolism of alcohol by the body including, but not limited to, acetone, acetaldehyde, and acetic acid. The term "alcohol biomarkers" includes, but is not limited to, Gamma Glutamyl Transferase (GGT), Aspartate Amino Transferase (AST), Alanine Amino Transferase (ALT), Mean Corpuscular Volume (MCV), Carbohydrate-Deficient Transferrin (CDT), Ethyl Glucuronide (EtG), Ethyl Sulfate (EtS), and Phosphatidyl Ethanol (PEth). The term "substances of abuse" refers to, but is not limited to, THC (Tetrahydrocannabinol or marijuana), cocaine, M-AMP (methamphetamine), OPI (morphine and heroin), OxyContin, Oxycodone, and PCP (phencyclidine). The term "biometric" refers to a biological characteristic that can be used to identify or verify the identity of a specific person or subject. The term "attribute" refers to an analyte or a biometric. The present invention addresses the need for analyte measurements of samples utilizing spectroscopy where the term "sample" generally refers to biological tissue. The term "subject" generally refers to a person from whom a sample measurement was acquired. The term "controlled environments" refers to any environment where the presence of an individual is subject to any restrictions related to alcohol, substances of abuse, or identity. This includes, but is not limited to, business offices, government buildings, probation centers, locations where individuals are located under home arrest, community corrections facilities, alcohol and substance of abuse treatment centers, public places incorporating check-in kiosks, and facilities or equipment with restricted access such as nuclear power plants and weapons storage facilities.

The terms "solid state light source" or "semiconductor light source" refer to all sources of light, whether spectrally narrow (e.g., a laser) or broad (e.g., an LED) that are based upon semiconductors which include, but are not limited to, light emitting diodes (LED's), vertical cavity surface emitting lasers (VCSEL's), horizontal cavity surface emitting lasers (HCSEL's), quantum cascade lasers, quantum dot lasers, diode lasers, or other semiconductor lasers. Furthermore, plasma light sources and organic LED's, while not strictly based on semiconductors, are also contemplated in the embodiments of the present invention and are thus included under the solid state light source and semiconductor light source definitions for the purposes of this disclosure.

For the purposes of this invention the term "dispersive spectrometer" indicates a spectrometer based upon any device, component, or group of components that spatially separate one or more wavelengths of light from other wavelengths. Examples include, but are not limited to, spectrometers that use one or more diffraction gratings, prisms, or holographic gratings. For the purposes of this invention the term "interferometric/modulating spectrometer" indicates a class of spectrometers based upon any device, component, or group of components that either modulate different wavelengths of light to different frequencies in time or selectively transmits or reflects certain wavelengths of light based upon the properties of light interference. Examples include, but are not limited to, Fourier transform interferometers, Hadamard spectrometers, Sagnac interferometers, mock interferometers, Michelson interferometers, one or more etalons, acousto-optical tunable filters (AOTF's), and one or more LEDs or VCSELs that are scanned or modulated. One skilled in the art recognizes that spectrometers based on combinations of dispersive and interferometric/modulating properties, such as those based on lamellar gratings, are also suitable for the present invention.

The invention makes use of "signals", described in some of the examples as absorbance or other spectroscopic measurements. Signals can comprise any measurement obtained concerning the spectroscopic measurement of a sample or change in a sample, e.g., absorbance, reflectance, intensity of light returned, fluorescence, transmission, Raman spectra, or various combinations of measurements, at one or more wavelengths. Some embodiments make use of one or more models, where such a model can be anything that relates a signal to the desired property. Some examples of models include those derived from multivariate analysis methods such as partial least squares regression (PLS), linear regression, multiple linear regression (MLR), classical least squares regression (CLS), neural networks, discriminant analysis, principal components analysis (PCA), principal components regression (PCR), cluster analysis, and K-nearest neighbors. Single or multi-wavelength models based on the Beer-Lambert law are special cases of classical least squares and are thus included in the term multivariate analysis for the purposes of the present invention.

The following detailed description should be read with reference to the drawings. The drawings, which are not necessarily to scale, depict illustrative embodiments that are not intended to limit the scope of the invention. For the purposes of the application, the term "about" applies to all numeric values, whether or not explicitly indicated. The term "about" generally refers to a range of numbers that one of skill in the art would consider equivalent to the recited value (i.e., having the same function or result). In some instances, the term "about" can include numbers that are rounded to the nearest significant figure.

As mentioned above, an effective apparatus or method for monitoring for the presence or concentration of alcohol or substances of abuse in controlled environments can be considered in terms of three primary components. The first component is a system that can measure the presence or concentration of an analyte (alcohol or substance of abuse) in an individual. The second component is a system that can verify that the measurement was obtained from a specific individual or member of a specific group of individuals. The third component is a system that combines the analyte and identity verification measurements, stores the results, and performs an action based upon the results where said action can be dependent on and vary according to the specific environment under consideration. For example, when alcohol is detected in an individual housed in a residential treatment center, the action performed by the present invention can be documentation of the positive alcohol test and notification of a facility administrator. In other embodiments, such as those intended to control access to secure facilities, the present invention can deny entry to any individual that either failed the alcohol/substance of abuse measurement or was determined to be unauthorized to enter by the identity verification measurement. The present invention links the first two components of the disclosed apparatuses and methods via a single spectroscopic measurement, which significantly reduces methods for circumvention.

Background of Tissue and Origins of the Spectroscopic Signal

Figure 2:
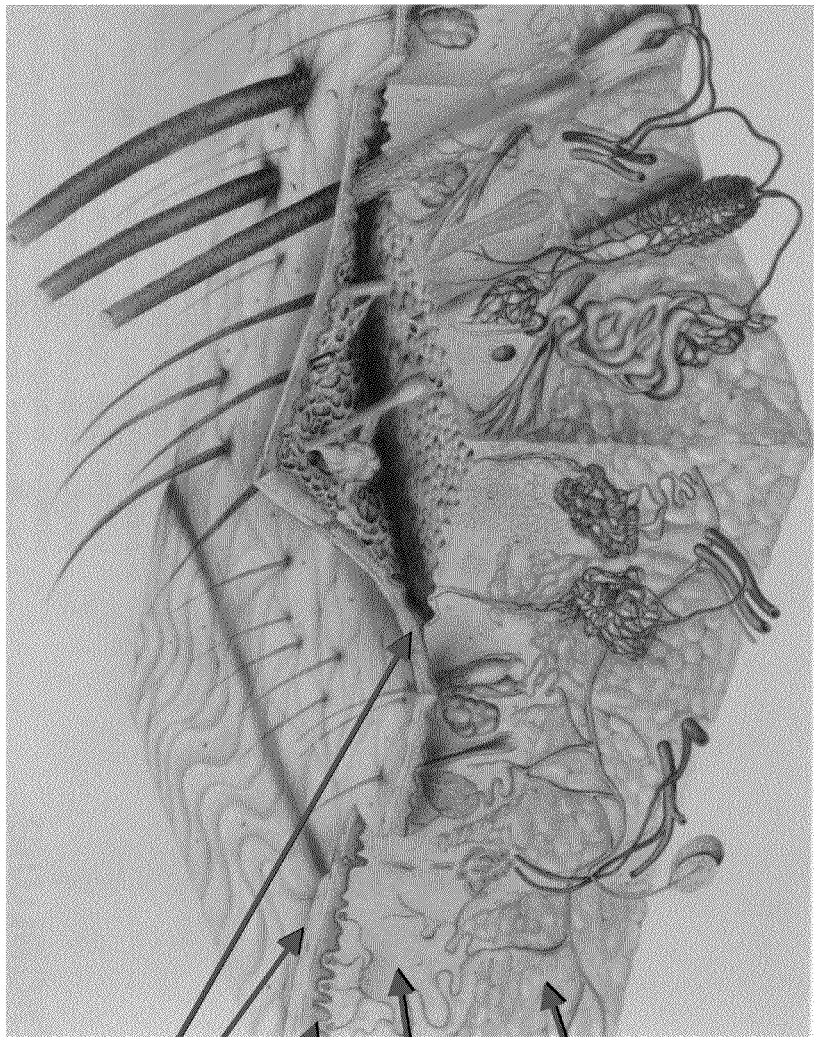
FIG. 2 is a diagram of the layered structure of human skin.
Figure 2:
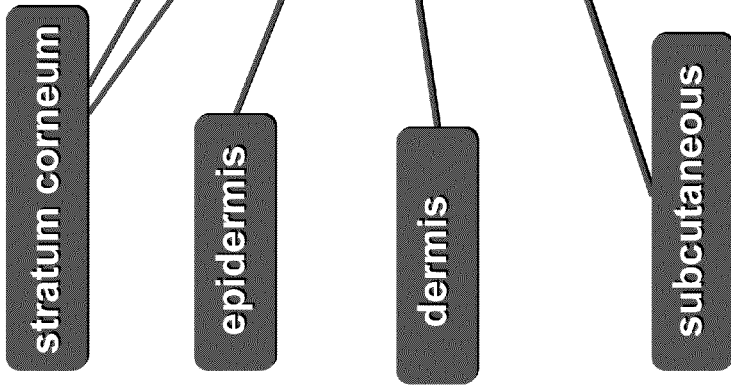

Human skin (FIG. 2) is comprised of epidermal, dermal, and subcutaneous layers, each of which has different physiological and chemical characteristics that influence their relative utility for alcohol measurements. The epidermis contains very little extracellular fluid, and therefore contains minimal information about hydrophilic analytes such as alcohol. The subcutaneous layer is largely comprised of lipids that have low water (and alcohol) solubility which make it poorly suited to alcohol measurements. However, the dermal layer has high water content (generally around 65%) and an extensive capillary bed conducive to the transport of alcohol, which makes it a useful layer of skin tissue for alcohol (or any analyte with high water solubility) measurements. The relative utility of the layers can depend upon the analyte property of interest. For example, THC is strongly soluble in lipids, which can increase the importance of the subcutaneous layer in THC measurements relative to its importance in alcohol measurements.

The layered structure of the tissue provides a wealth of spectroscopic information that can be used to discriminate between people. This biometric signal is a function of many skin properties such as the relative thicknesses of the tissue layers, their scattering coefficients, and the analyte concentrations within each layer. For example, the subcutaneous layer is largely comprised of lipids that are typically absent in other tissue layers. In contrast, the dermal layer is composed primarily of water and collagen. As a result, the spectroscopic measurement contains the relative signal contributions of these analytes and therefore provides insight into both the chemical composition and structure of the tissue. Because different people have different tissue properties (dermal hydration, collagen densities, tissue layer thicknesses), the spectroscopic measurement simultaneously captures both analyte signals (e.g., alcohol signal) and the inter-subject differences that collectively form the biometric signal.

Figure 3:
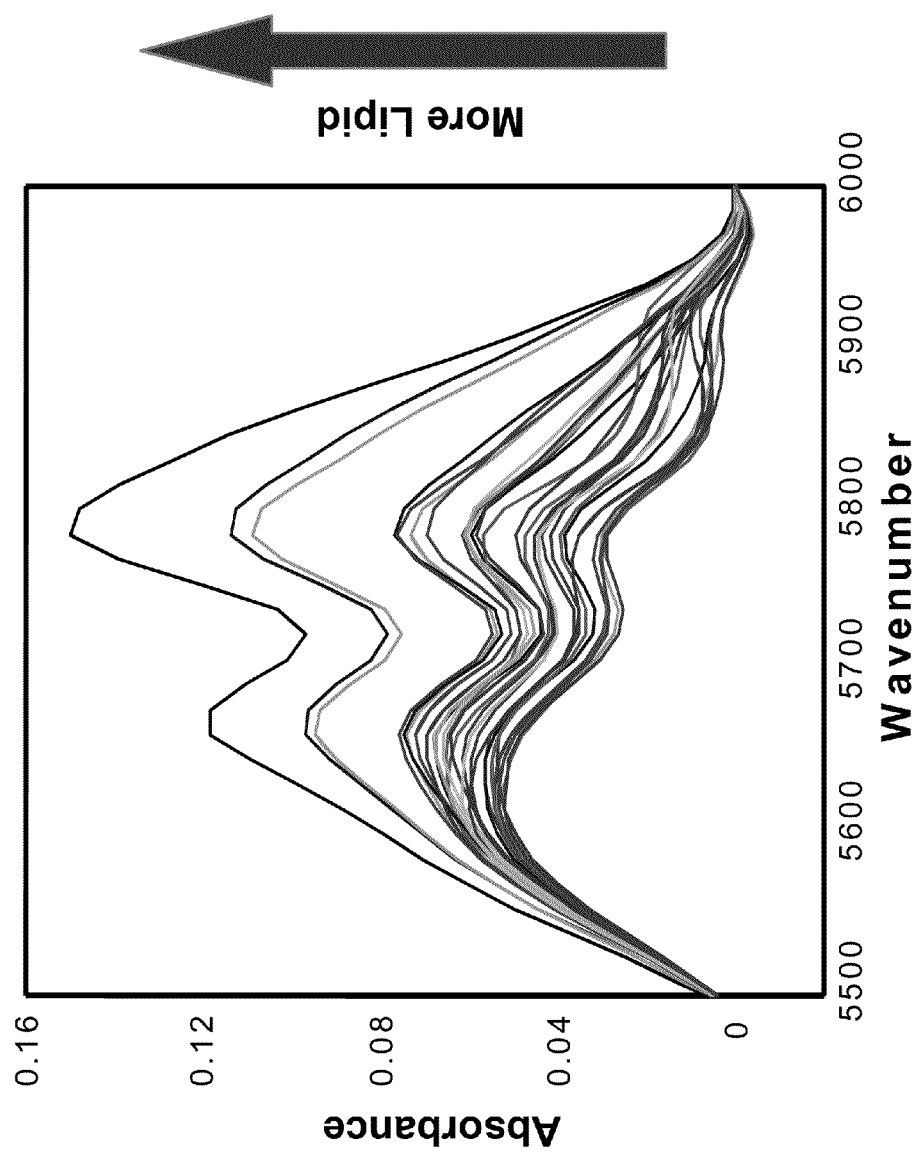
FIG. 3 shows the lipid signals obtained from spectroscopic measurements of 31 individuals.
Figure 4:
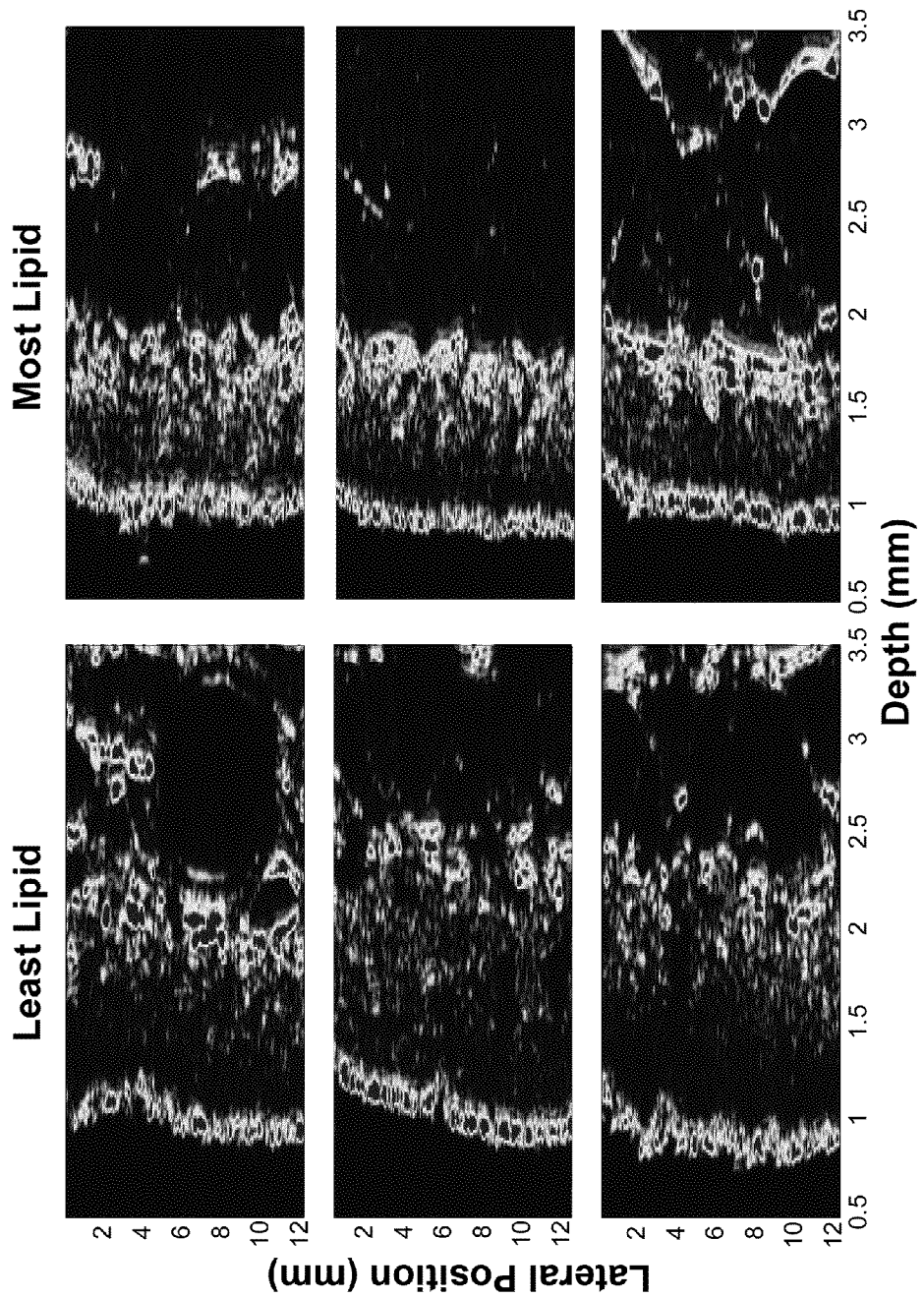
FIG. 4 shows ultrasound images of 6 individuals that demonstrate the difference in tissue structure between people.

FIGS. 3 and 4 combine to provide an example of the inter-subject discriminatory power of the spectroscopic signal. FIG. 3 shows the 5500-6000 $cm^{-1}$ region of NIR spectra obtained from 31 subjects. The pronounced peaks at 5675 and 5800 $cm^{-1}$ correspond to the spectral signature of lipids, which is an indicator that a portion of the NIR signal originated in the subcutaneous tissue layer for some of the 31 subjects. The variation of the lipid signature suggests that the subjects with weaker lipid signal have thicker epidermal and dermal tissue layers, thus preventing the NIR light from reaching the deeper subcutaneous layer where lipids are located. FIG. 4 offers a different perspective that shows ultrasound images that were obtained from 3 of the 31 subjects who exhibited a strong lipid signal and 3 subjects of the 31 that exhibited no discernable lipid signal. In ultrasound images of tissue, a large signal (brighter parts of the image) generally corresponds to a boundary between layers. As such, the strong signal near 1 mm of depth in each window of FIG. 3 corresponds to the ultrasound probe-epidermal interface. The next region of interest is the dermal-subcutaneous boundary, which generally occurs between 1.5 mm and 2.5 mm of depth. Comparison of the two groups demonstrates a marked difference in dermal thickness between the strong and weak lipid signal subjects. Consequently, the magnitude of the lipid signal is of interest because it provides chemical and structural information that can be used to differentiate subjects.

Figure 5:
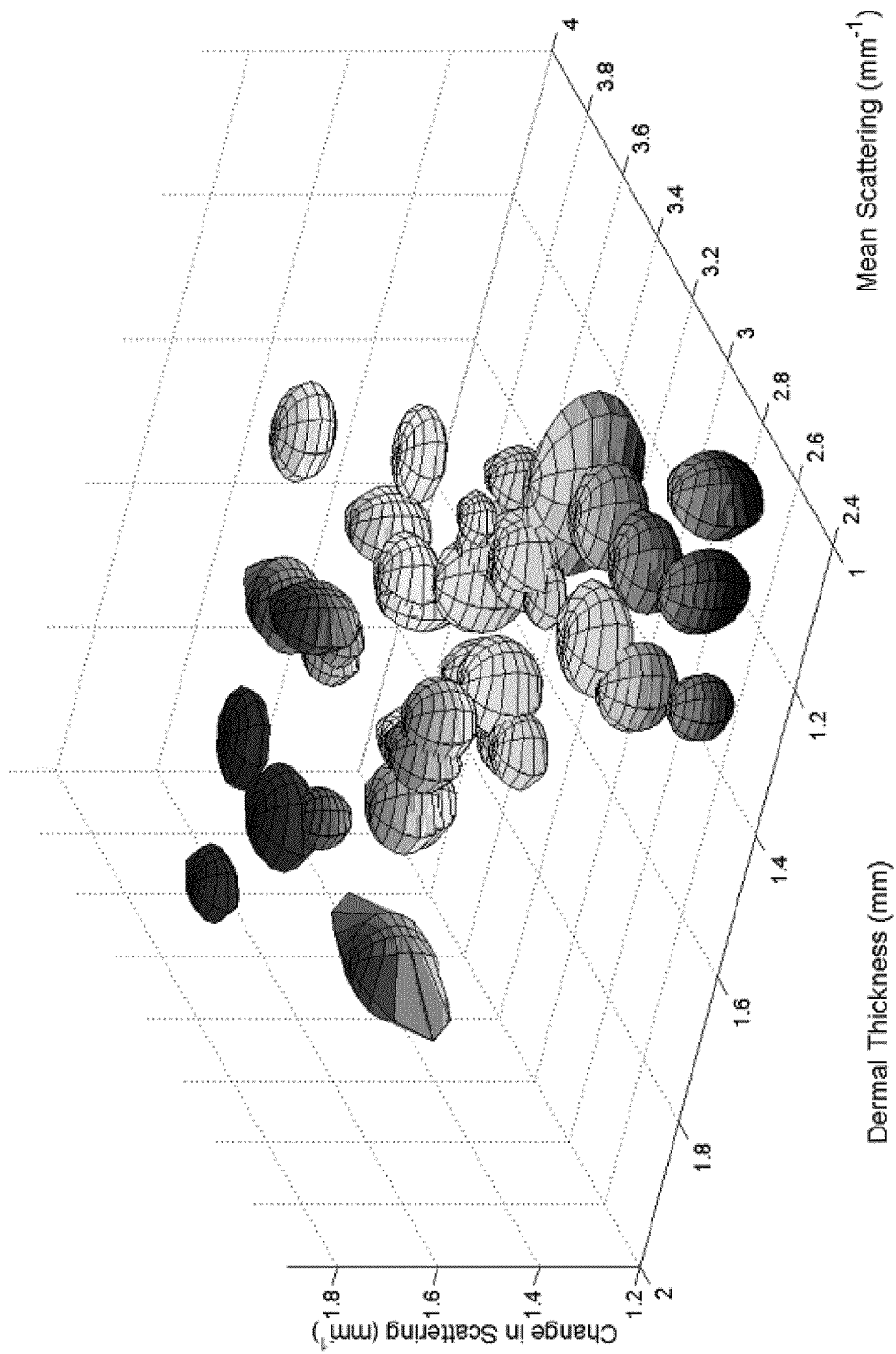
FIG. 5 is a diagram showing the inter-subject discriminatory power of the spectroscopic measurement of the present invention.

While lipid content provides an intuitive example of a discernable property in the spectroscopic measurement, multiple structural and chemical properties can be extracted. In aggregate, these properties form a powerful technique to discriminate between people. FIG. 5 is a visual presentation of the inter-subject resolving power of the measurement using 3 extracted properties. Each ellipsoid in FIG. 5 encompasses the properties extracted from multiple measurements (typically 10-15) obtained from a single subject. Even with only three properties, the measurements acquired from each subject reside in a distinct region of the 3-dimensional space. This example can be extended to include additional properties and thereby further improve the discriminatory power of the biometric signal. The extracted properties can be representative of physical variables (e.g., dermal thickness or scattering coefficient) or mathematically derived from subject measurements (e.g., factors from a principal components analysis, PCA).

The present invention obtains the first two components of the disclosed apparatuses and methods from a single spectroscopic measurement of tissue (e.g., skin). Some demonstrative embodiments of suitable spectroscopic measurement devices are described below. These examples should not be construed as limiting to the invention as one skilled in the art recognizes that other embodiments exist that serve substantially the same function. For example, while the majority of the disclosure relates to near infrared spectroscopic measurements, Raman measurements (and therefore Raman spectrometers) can also be suitable for the present invention.

Embodiments for Measuring the Spectroscopic Signal

Figure 6:
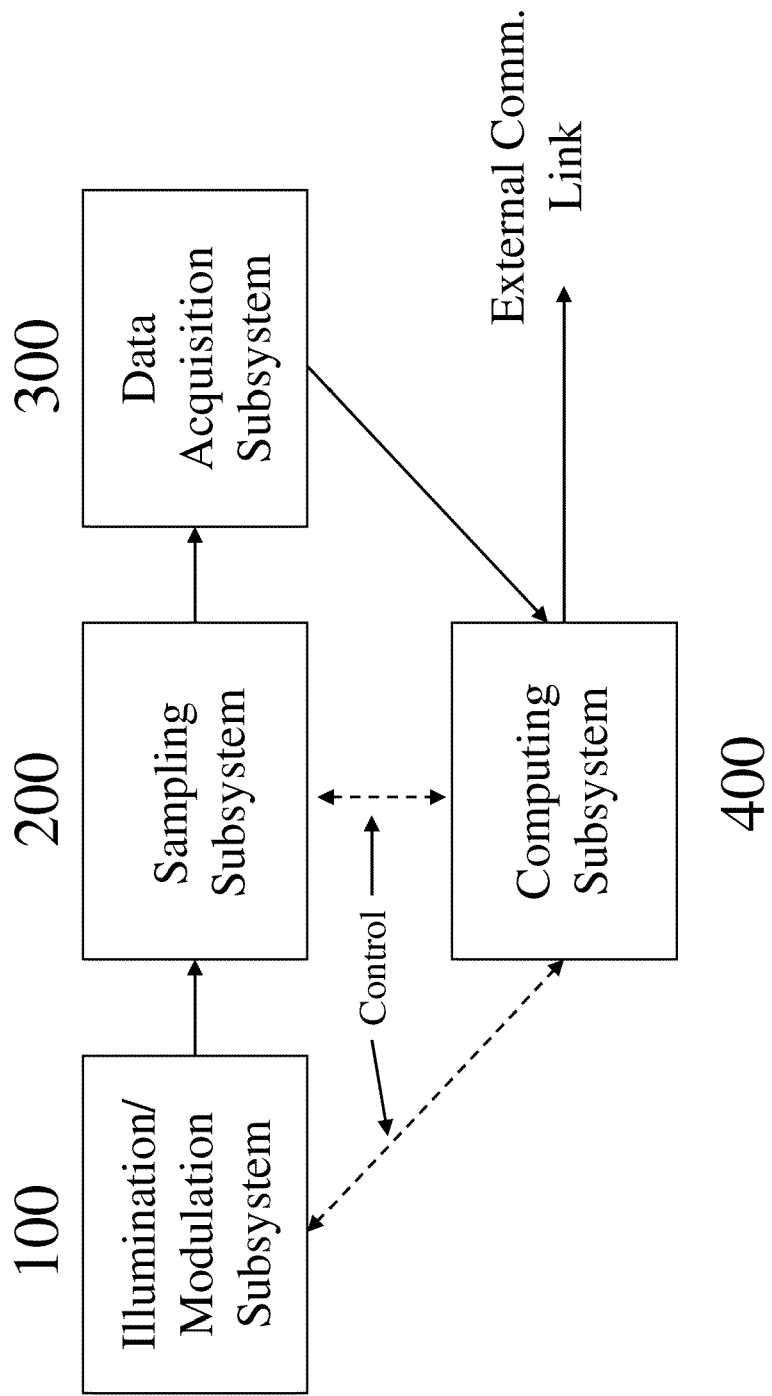
FIG. 6 is a schematic depiction of a noninvasive spectrometer system incorporating the subsystems of the present invention.

Several embodiments of the present invention include an apparatus for measuring the spectroscopic signal of tissue, typically skin. Referring now to FIG. 6, a noninvasive monitoring system that is able to achieve acceptable levels of accuracy and precision for analyte property measurements is depicted in schematic view. The overall systems of the present invention can be viewed for discussion purposes as comprising five subsystems; those skilled in the art will appreciate other subdivisions of the functionality disclosed. The subsystems include an illumination/modulation subsystem 100, a tissue sampling subsystem 200, a data acquisition subsystem 300, a computing subsystem 400, and a calibration subsystem 500 (not shown).

Figure 7:
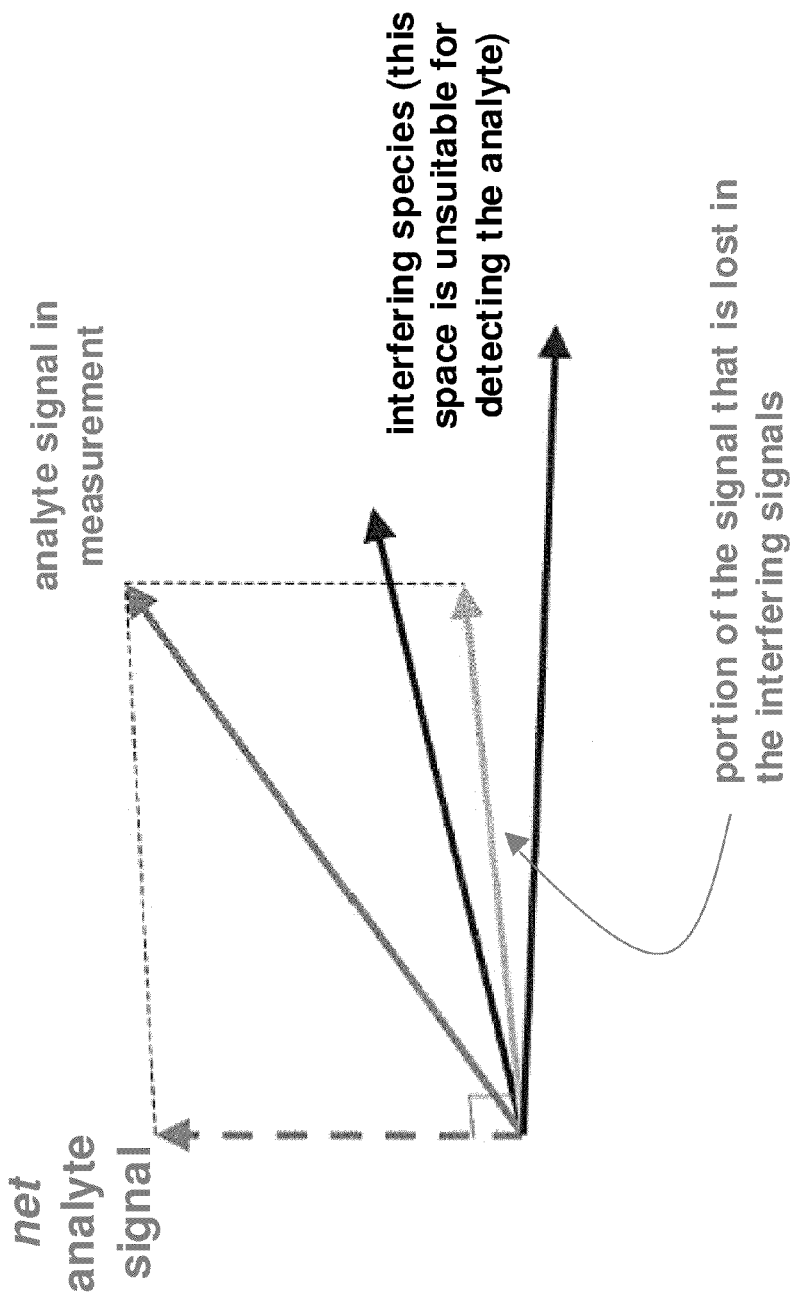
FIG. 7 is a graphical depiction of the concept of net attribute signal in a three-component system.

The subsystems can be designed and integrated in order to achieve a desirable net attribute signal-to-noise ratio. The net attribute signal is the portion of the near-infrared spectrum that is specific for the attribute of interest because it is orthogonal to other sources of spectral variance. FIG. 7 is a graphical representation of the net attribute signal in a three-dimensional system. The net attribute signal-to-noise ratio is directly related to the accuracy and precision of the noninvasive attribute determination by quantitative near-infrared spectroscopy with the present invention.

The subsystems provide reproducible and preferably spatially uniform radiance of the tissue, low tissue sampling error, depth targeting of appropriate layers of the tissue, efficient collection of diffuse reflectance spectra from the tissue, high optical throughput, high photometric accuracy, large dynamic range, excellent thermal stability, effective calibration maintenance, effective calibration transfer, built-in quality control and ease-of-use. Each of the subsystems is discussed below in more detail.

Illumination/Modulation Subsystem 100

The illumination/modulation subsystem 100 generates the light used to interrogate the sample (e.g., skin tissue of a human). In classical spectroscopy using dispersive or interferometric spectrometers, the spectrum of a polychromatic light source (or sample of interest) is measured either by dispersing the different wavelengths of light spatially (e.g., using a prism or a diffraction grating) or by modulating different wavelengths of light to different frequencies (e.g., using a Michelson interferometer). In these cases, a spectrometer (a subsystem distinct from the light source) is required to perform the function of "encoding" different wavelengths either spatially or in time such that each can be measured substantially independently of other wavelengths. While dispersive and interferometric spectrometers are known in the art and can adequately serve their function in some environments and applications, they can be limited by their cost, size, fragility, and complexity in other applications and environments.

An advantage of solid state light sources incorporated in the systems disclosed in the present invention is that they can be modulated in intensity. Thus, multiple light sources that emit different wavelengths of light can be used, with each light source modulated at a different frequency. The independently modulated light sources can be optically combined into a single beam and introduced to the sample. A portion of the light can be collected from the sample and measured by a single photodetector. The result is the effective combination of the light source and the spectrometer into a single illumination/modulation subsystem that can offer significant benefits in size, cost, energy consumption, and overall system stability since the spectrometer, as an independent subsystem, is eliminated from the measurement system.

Several parameters of systems for measuring analyte properties incorporating solid state light sources must be considered including, but not limited to, the number of solid state light sources required to perform the desired measurement, the emission profile of the light sources (e.g., spectral width, intensity), light source stability and control, and their optical combination. As each light source is a discrete element, it can be advantageous to combine the output of multiple light sources into a single beam such that they are consistently introduced and collected from the sample.

Furthermore, the modulation scheme for the light sources must also be considered as some types of sources can be amenable to sinusoidal modulations in intensity whereas others can be amenable to being switched on and off. In the case of sinusoidal modulation, multiple light sources can be modulated at different frequencies based on the electronics design of the system. The light emitted by the multiple sources can be optically combined, for example using a light pipe or other homogenizer, introduced and collected from the sample of interest, and then measured by a single detector. The resulting signal can be converted into an intensity versus wavelength spectrum via a Fourier, or similar, transform. Alternatively, some light sources are switched between the on and off state which is amenable to a Hadamard transform approach. However, in some embodiments, rather than a traditional Hadamard mask that blocks or passes different wavelengths at different times during a measurement, the Hadamard scheme can be implemented in electronics as solid state light sources can be cycled at high frequencies. A Hadamard transform can be used to determine the intensity versus wavelength spectrum.

Another advantage of solid state light sources is that many types (e.g., VCSEL's) emit a narrow range of wavelengths (which determines the effective resolution of the measurement). Consequently, in preferred embodiments, shaping or narrowing the emission profile of light sources with optical filters or other approaches is not required as they are already sufficiently narrow. This can be advantageous due to decreased system complexity and cost. Furthermore, the emission wavelengths of some solid state light sources, such as VCSEL's, are tunable over a range of wavelengths via either the supplied drive current, drive voltage, or by changing the temperature of the light source. The advantage of this approach is that if a given measurement requires a specific number of wavelengths, the system can achieve the requirement with fewer discrete light sources by tuning them over their feasible ranges. For example, if measurement of a non-invasive property required 20 wavelengths, 10 discrete VCSEL's might be used with each of the 10 being tuned to 2 different wavelengths during the course of a measurement. In this type of scheme, a Fourier or Hadamard approach remains appropriate by changing the modulation frequency for each tuning point of a light source or by combining the modulation scheme with a scanning scheme.

It is important to note that the present invention also envisions several embodiments of broadband light sources rather than narrowband solid state light sources. An example of a suitable blackbody light source is a tungsten filament lamp. Another example light source is a resistive element such as those commonly used as igniters for furnaces and stoves. These light sources have a lower color temperature than standard filament lamps and are therefore more efficient in the near-infrared spectral region. These sources also have comparatively large emissive surfaces that are less sensitive to spatial effects that are encountered throughout the lifetime of the light source. An additional advantage of igniter-based light sources is a substantially longer lifetime when compared to filament lamps. In these embodiments, the broad blackbody source can be converted to multiple, narrow light sources using optical filters such as, but not limited to, linearly variable filters (LVF's), dielectric stacks, distributed Bragg gratings, photonic crystal lattice filters, polymer films, absorption filters, reflection filters, etalons, dispersive elements such as prisms and gratings, and quantum dot filters. The resulting multiple bands of wavelengths can be modulated by a Fourier scheme or Hadamard mask.

Figure 8:
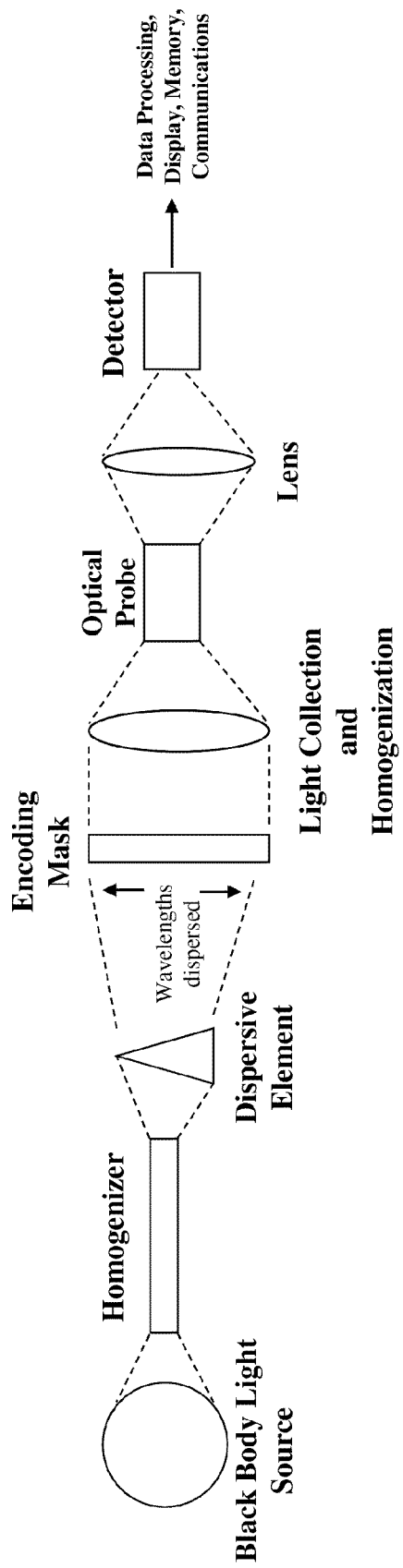
FIG. 8 is a schematic of an embodiment of the present invention incorporating a blackbody light source with Hadamard encoding.
Figure 9:
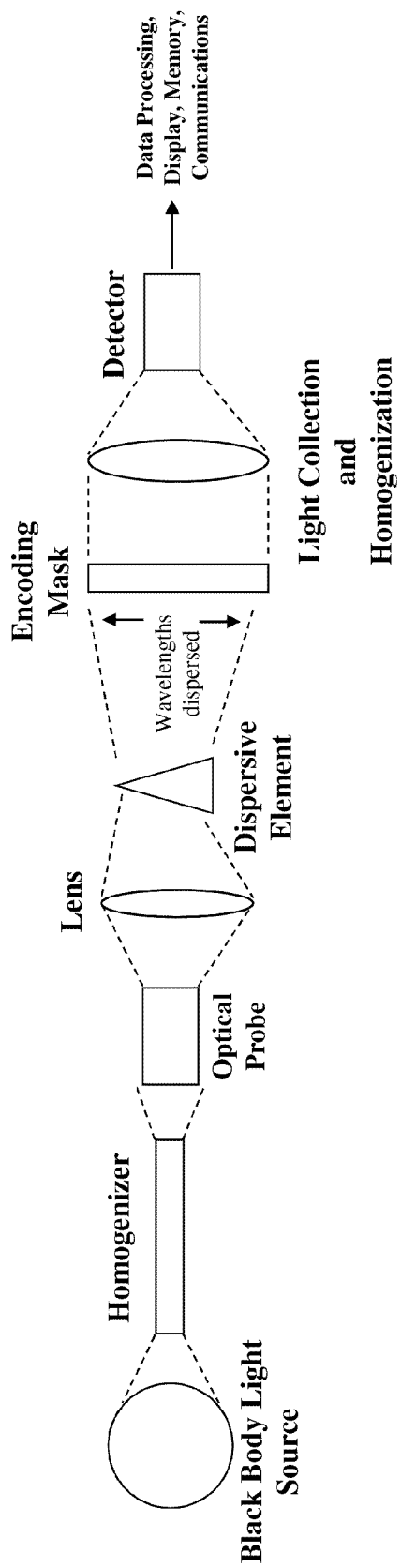
FIG. 9 is a schematic of an embodiment of the present invention incorporating a blackbody light source with Hadamard encoding, where the encoding is performed after the light has interacted with the sample.

In other embodiments, a dispersive element such as a grating or prism is used to spatially separate the wavelengths of light from a broadband source (either a blackbody, LED, or other broad emitting light source). The dispersive element separates the different wavelengths which can be independently modulated at their locations on a focal plane using a Hadamard mask or mechanical chopper (e.g., for a Fourier scheme). Similar to the embodiments previously described, the resulting light can be homogenized and introduced to the optical probe. FIGS. 8 and 9 show schematics of embodiments of the present invention that incorporate a blackbody light source with Hadamard encoding. In mechanically modulated embodiments incorporating a Hadamard mask or mechanical chopper, in some cases it can be advantageous to perform the modulating step after the light has been collected from the sample by the optical probe. FIG. 9 shows a schematic of an embodiment of such a system.

Analyte properties can be measured at a variety of wavelengths spanning the ultraviolet and infrared regions of the electromagnetic spectrum. For in vivo measurements in skin, such as alcohol or substances of abuse, the near infrared (NIR) region of 1,000 nm to 2,500 nm region can be important due to the sensitivity and specificity of the spectroscopic signals for the analyte of interest as well as other chemical species (e.g. water) that are present in human skin. Furthermore, the absorptivities of the analytes are low enough that the near infrared light can penetrate a few millimeters into the skin where the analytes of interest reside. The 2,000 nm to 2,500 nm wavelength range can be of particular utility as it contains combination bands rather than the weaker, less distinct overtones encountered in the 1,000 to 2,000 nm portion of the NIR.

In addition to the commonly available LED's, VCSEL's, diode lasers in the visible region of the spectrum, there are solid state light sources available with emission wavelengths throughout the NIR region (1,000 to 2,500 nm). These light sources are suitable for the analyte and biometric property measurement systems of the present invention. Some examples of available NIR solid state light sources that are VCSEL's produced by Vertilas GmbH, and the VCSEL's, quantum cascade lasers, and laser diodes available from Laser Components GmbH. These examples are included for demonstrative purposes and are not intended to be limiting of the types of solid state light sources suitable for use with the present invention.

Measurement Resolution and Resolution Enhancement

In a dispersive spectrometer, the effective resolution of a spectroscopic measurement is often determined by the width of an aperture in the system. The resolution limiting aperture is often the width of the entrance slit. At the focal plane where light within the spectrometer is detected, multiple images of the slit are formed, with different wavelengths located at different spatial locations on the focal plane. Thus, the ability to detect one wavelength independent of its neighbors is dependent on the width of the slit. Narrower widths allow better resolution between wavelengths at the expense of the amount of light that can be passed through the spectrometer. Consequently, resolution and signal to noise ratio generally trade against each other. Interferometric spectrometers have a similar trade between resolution and signal to noise ratio. In the case of a Michelson interferometer the resolution of the spectrum is in part determined by the distance over which a moving mirror is translated with longer distances resulting in greater resolution. The consequence is that the greater the distance, the more time is required to complete a scan (a full translation of the mirror).

In the case of the measurement systems of the present invention, the resolution of the spectrum is determined by the spectral width of each of the discrete light sources (whether a different light source, one tuned to multiple wavelengths, or a combination thereof). For measurements of analyte properties requiring high resolution, a VCSEL or other suitable solid state laser can be used. The widths of the laser's emission can be very narrow, which translates into high resolution. In measurement applications where moderate to low resolution are required, LED's can be suitable as they typically have wider emission profiles (the output intensity is distributed across a wider range of wavelengths) than solid state laser alternatives.

The effective resolution of light sources can be enhanced through the use, or combination of, different types of optical filters. The spectral width of a light source can be narrowed or attenuated using one or more optical filters in order to achieve higher resolution (e.g., a tighter range of emitted wavelengths). Examples of optical filters that are contemplated in embodiments of the present invention include, but are not limited to: linearly variable filters (LVF's), dielectric stacks, distributed Bragg gratings, photonic crystal lattice filters, polymer films, absorption filters, reflection filters, etalons, dispersive elements such as prisms and gratings, and quantum dot filters.

Another means for improving the resolution of measurements obtained from embodiments of the present invention is deconvolution. Deconvolution, and other similar approaches, can be used to isolate the signal difference that is present between two or more overlapping broad light sources. For example, two light sources with partially overlapping emission profiles can be incorporated into a measurement system. A measurement can be acquired from a sample and a spectrum generated (via a Hadamard, Fourier transform, or other suitable transform). With knowledge of the emission profiles of the light sources, the profiles can be deconvolved from the spectrum in order to enhance the resolution of the spectrum.

Stabilization and Control of Light Source Wavelength and Intensity

The peak emission wavelength of solid state light sources, particularly lasers, can be influenced by changing the thermal state or electrical properties (e.g., drive current or voltage) of the light source. In the case of semiconductor lasers, changing the thermal state and electrical properties alters the optical properties or physical dimensions of the lattice structure of the semiconductor. The result is a change in the cavity spacing within the device, which alters the peak wavelength emitted. Since solid state light sources exhibit these effects, when they are used in spectroscopic measurement systems the stability of the peak wavelength of emission and its associated intensity can be important parameters. Consequently, during a measurement, control of both the thermal state and electrical properties of each light source can be advantageous in terms of overall system robustness and performance. Furthermore, the change in optical properties caused by thermal state and electrical conditions can be leveraged to allow a single light source to be tuned to multiple peak wavelength locations. This can result in analyte property measurement systems that can measure more wavelength locations than the number of discrete light sources which can reduce system cost and complexity.

Figure 10:
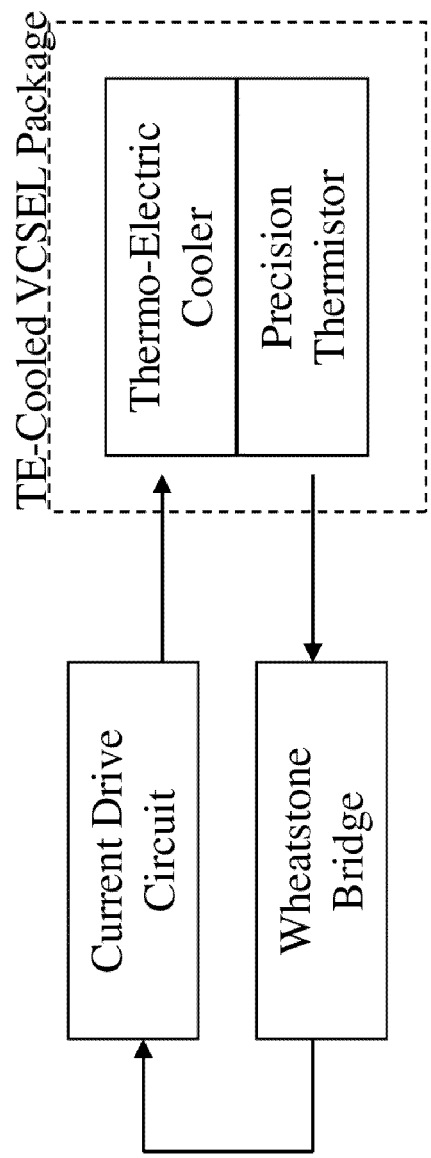
FIG. 10 is an embodiment of an electronic circuit designed to monitor and control the temperature of a solid state light source.

Temperature stabilization can be achieved using multiple approaches. In some embodiments, a light source or light sources can be stabilized by raising the temperature above (or cooling below) ambient conditions with no additional control of the temperature. In other embodiments, the light source or light sources can be actively controlled to a set temperature (either cooled or heated) using a control loop. A diagram of a temperature control loop circuit suitable for the present invention is shown in FIG. 10.

Figure 11:
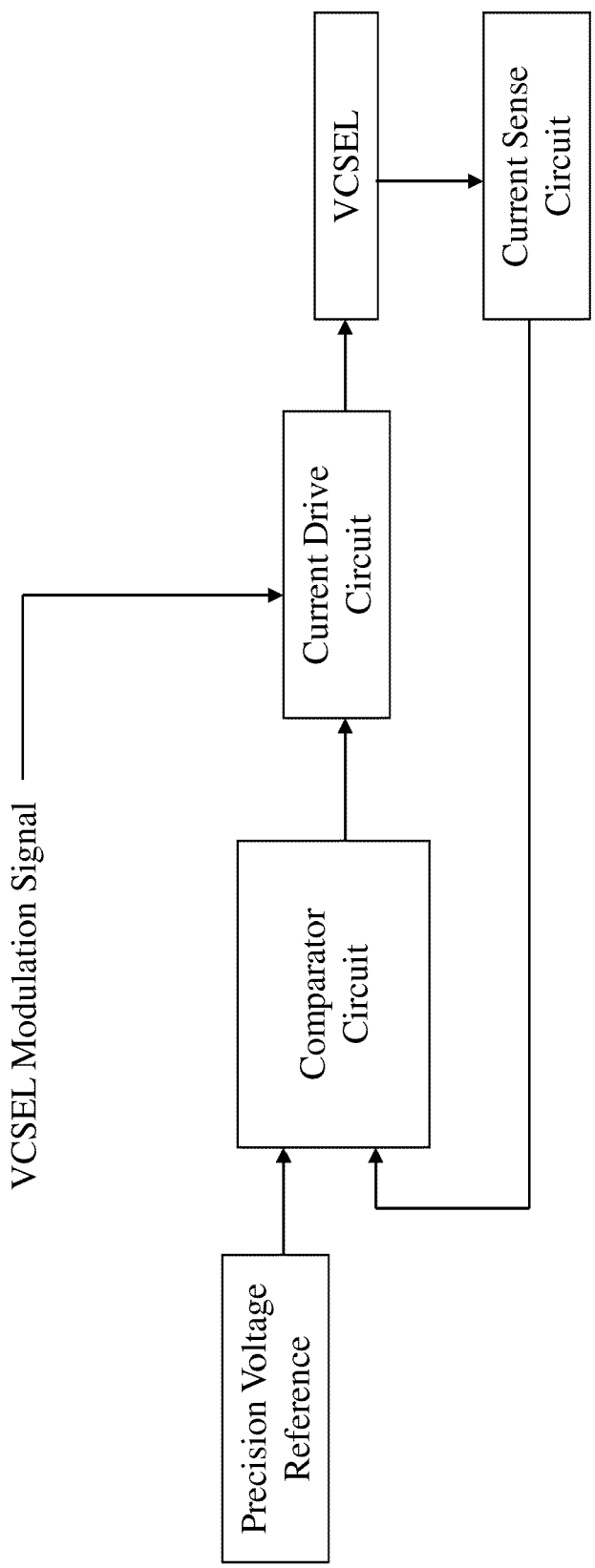
FIG. 11 is an embodiment of an electronic circuit designed to control the drive current of a solid state light source including means for turning the light source on and off.

The electrical properties of light sources also influence the emission profile (e.g., wavelength locations of emission) of solid state light sources. It can be advantageous to stabilize the current and/or voltage supplied to the light source or light sources. For example, the peak emission of VCSEL's depends on drive current. For embodiments where the stability of the peak wavelength is important, the stability of the drive current becomes an important figure of merit. In such cases, an electronic circuit can be designed to supply a stable drive current to the VCSEL. The complexity and cost of the circuit can depend on the required stability of the drive current. FIG. 11 shows a current drive circuit suitable for use with the present invention. One skilled in the art recognizes that alternative embodiments of current control circuits are known in the art and can also be suitable for the present invention. Furthermore, some solid state light sources require control of the drive voltage, rather than drive current; one skilled in the art recognizes that electronics circuits designed to control voltage rather than current are readily available.

Figure 12:
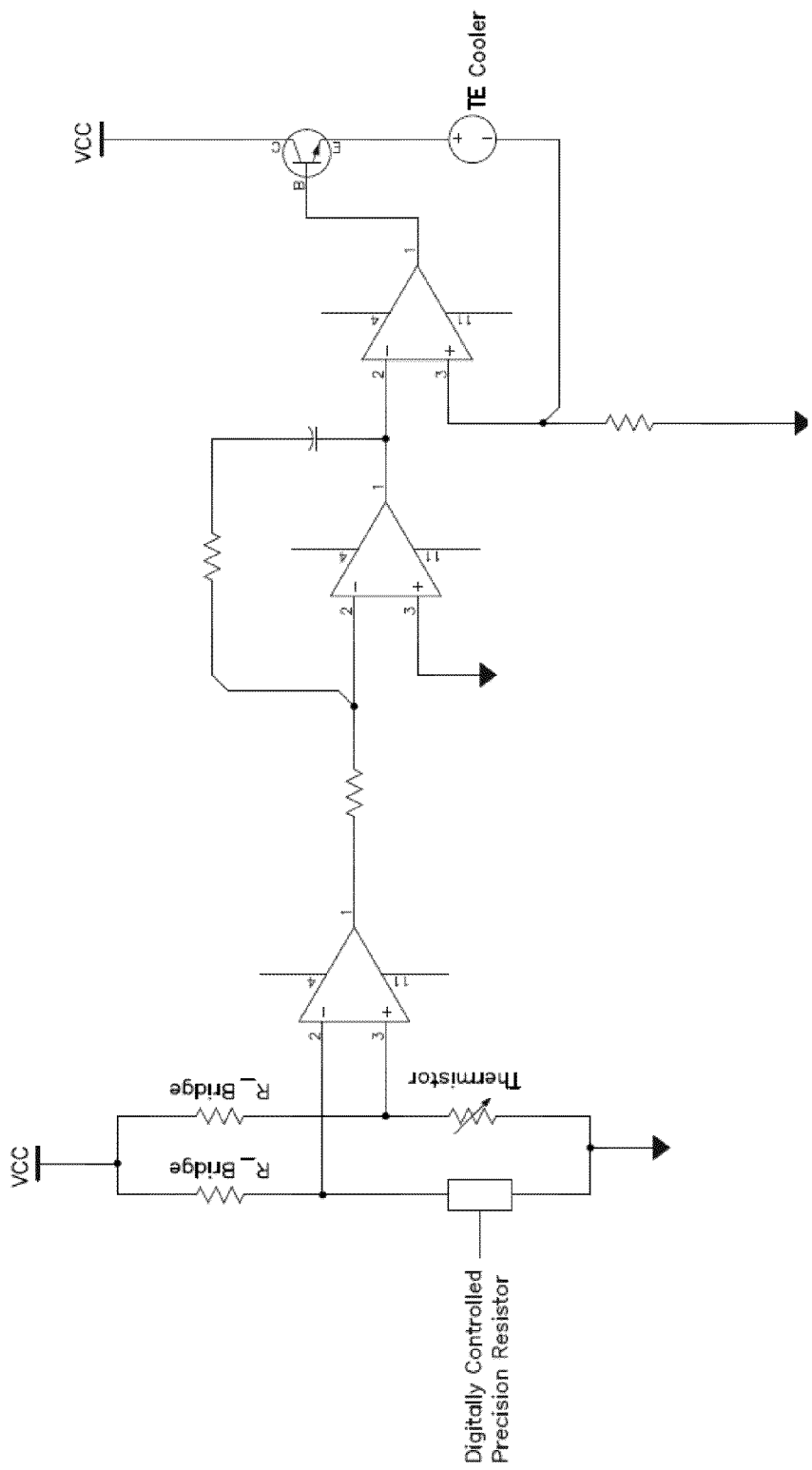
FIG. 12 is an embodiment of an electronic circuit designed to monitor and control the temperature of a solid state light source including means for altering the desired control temperature.
Figure 13:
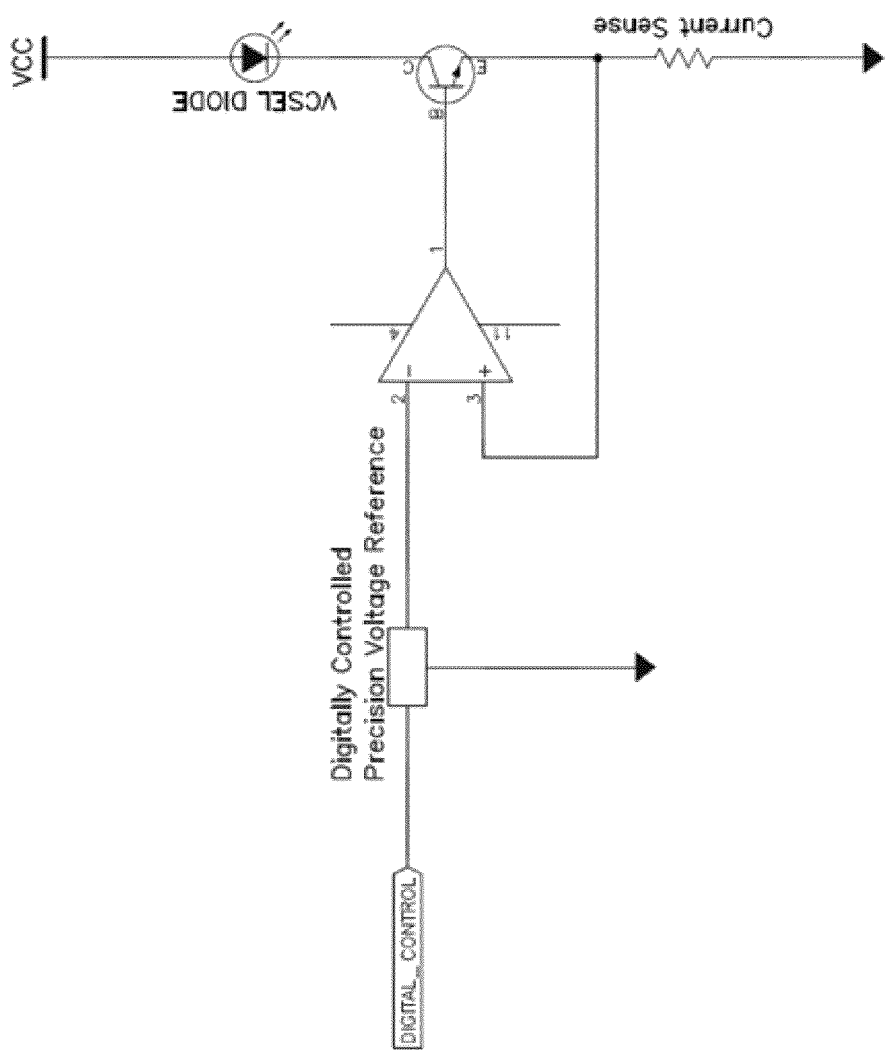
FIG. 13 is an embodiment of an electronic circuit designed to control the drive current of a solid state light source including means for turning the light source on and off and altering the desired drive current.

In some embodiments, a single solid state light source, such as a VCSEL, is tuned to multiple wavelengths during the course of a measurement. In order to achieve the tuning of the light sources, the circuits shown in FIGS. 10 and 11 can be modified to include the control of the temperature set point and current, respectively. FIGS. 12 and 13 depict embodiments of temperature and current control circuits, respectively, that allow tuning of the emission wavelength. In some embodiments, either tuning temperature or drive current/voltage can be sufficient to realize the desired tuning of the peak emission wavelength. In other embodiments, control of both the temperature and drive current/voltage can be required to achieve the desired tuning range.

Furthermore, optical means for measuring and stabilizing the peak emission wavelength can also be incorporated into the systems described in connection with the present invention. A Fabry-Perot etalon can be used to provide a relative wavelength standard. The free spectral range and finesse of the etalon can be specified to provide an optical passband that allows active measurement and control of the VCSEL peak wavelength. An example embodiment of this etalon uses a thermally stabilized, flat fused-silica plate with partially mirrored surfaces. For systems where each VCSEL is required to provide multiple wavelengths, the free spectral range of the etalon can be chosen such that its transmission peaks coincide with the desired wavelength spacing for tuning. One skilled in the art will recognize that there are many optical configurations and electronic control circuits that are viable for this application. One example control circuit is shown in FIG. 13. An alternate wavelength encoding scheme uses a dispersive grating and a secondary array detector to encode the VCSEL wavelength into a spatial location on the array. For either the dispersive or the etalon based schemes, a secondary optical detector that has less stringent performance requirements than the main optical detector can be used. Active control can reduce the stability requirements of the VCSEL temperature and current control circuits by allowing real time correction for any drift.

Light homogenizers such as optical diffusers, light pipes, and other scramblers can be incorporated into some embodiments of the illumination/modulation subsystem 100 in order to provide reproducible and, preferably, uniform radiance at the input of the tissue sampling subsystem 200. Uniform radiance can ensure good photometric accuracy and even illumination of the tissue. Uniform radiance can also reduce errors associated with manufacturing differences between light sources. Uniform radiance can be utilized in the present invention for achieving accurate and precise measurements. See, e.g., U.S. Pat. No. 6,684,099, which is incorporated herein by reference.

A ground glass plate is an example of an optical diffuser. The ground surface of the plate effectively scrambles the angle of the radiation emanating from the light source and its transfer optics. A light pipe can be used to homogenize the intensity of the radiation such that it is spatially uniform at the output of the light pipe. In addition, light pipes with a double bend will scramble the angles of the radiation. For creation of uniform spatial intensity and angular distribution, the cross section of the light pipe should not be circular. Square, hexagonal and octagonal cross sections are effective scrambling geometries. The output of the light pipe can directly couple to the input of the tissue sampler or can be used in conjunction with additional transfer optics before the light is sent to the tissue sampler. See, e.g., U.S. patent application Ser. No. 09/832,586, "Illumination Device and Method for Spectroscopic Analysis," which is incorporated herein by reference.

Sampling Subsystem 200

FIG. 6 indicates that the orientation of the tissue sampling subsystem 200 is between the illumination/modulation 100 and data acquisition 300 subsystems. The tissue sampling subsystem 200 introduces radiation generated by the illumination/modulation subsystem 100 into the tissue of the subject, collects a portion of the radiation that is not absorbed by the tissue and sends that radiation to optical detector in the data acquisition subsystem 300 for measurement.

Figure 14:
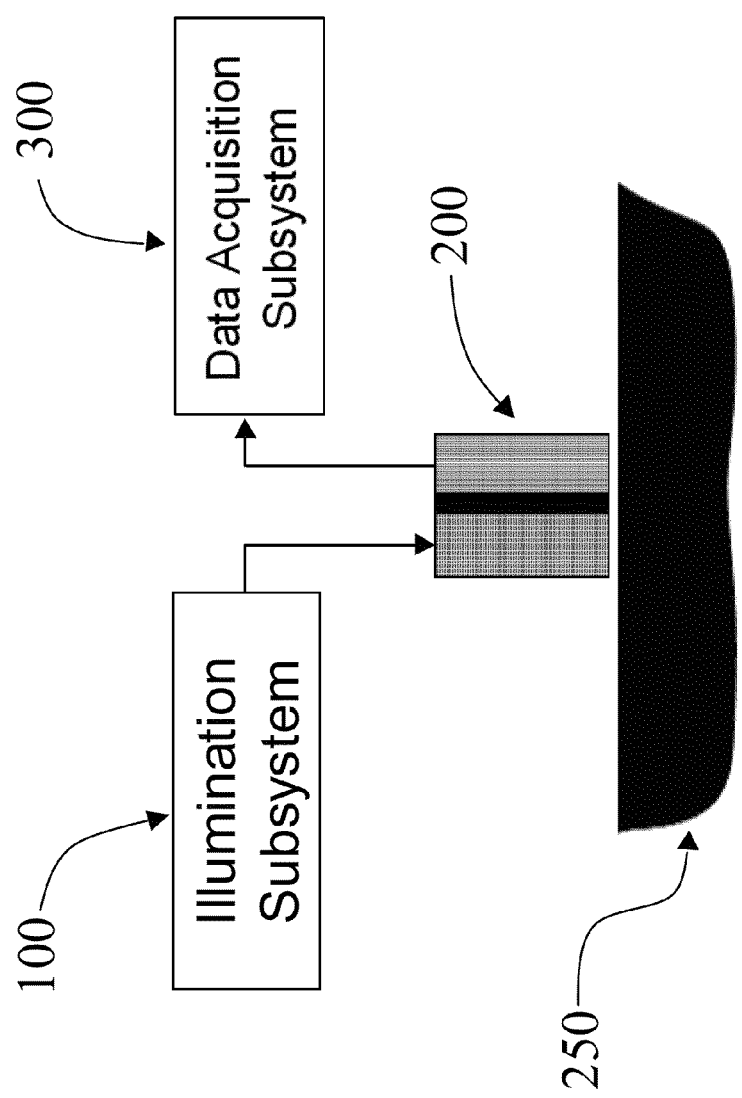
FIG. 14 is a schematic depiction of a system that measures a sample in reflectance.
Figure 15:
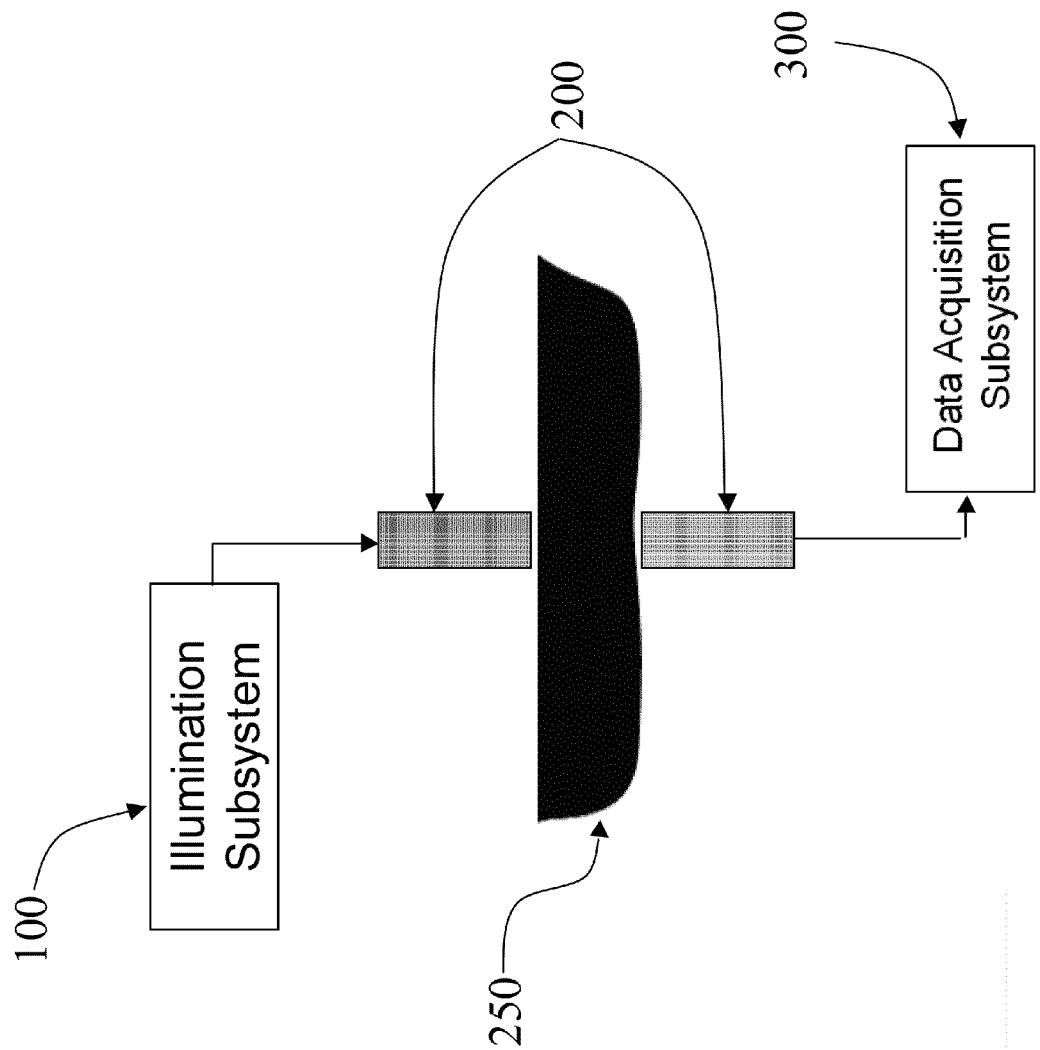
FIG. 15 is a schematic depiction of a system that measures a sample in transmission.

In practicing the method of the present invention, an area of the sample can be selected as the point of analysis for the sampling subsystem 200. In the case of noninvasive tissue measurements, this area can include the finger, palms, wrists, earlobe, forearms or any other skin surface. Further, even in the case of using fingers, the present invention allows use of multiple sites along the area. For example, the finger can be measured on both the dorsal and ventral surfaces. Embodiments of the sampling subsystem 200 can be such that light is introduced and collected from the sample 250 in either reflectance or transmission geometries (shown in FIGS. 14 and 15, respectively).

Another advantage of the present invention is that it, unlike fingerprint readers, can use different fingers (or other sites) for enrollment and for subsequent verification. This capability provides for increased enrollment efficiency since the user only has to present one enrollment site to the system, but also provides critical flexibility during the use of the device. An example of this flexibility is the case where the user has enrolled a site on a particular hand and that particular site is unavailable for subsequent analysis due to some injury or other contamination of the site. This spectroscopic-based biometric system of the present invention can operate on the site from the other hand without previous enrollment of such site.

Figure 16:
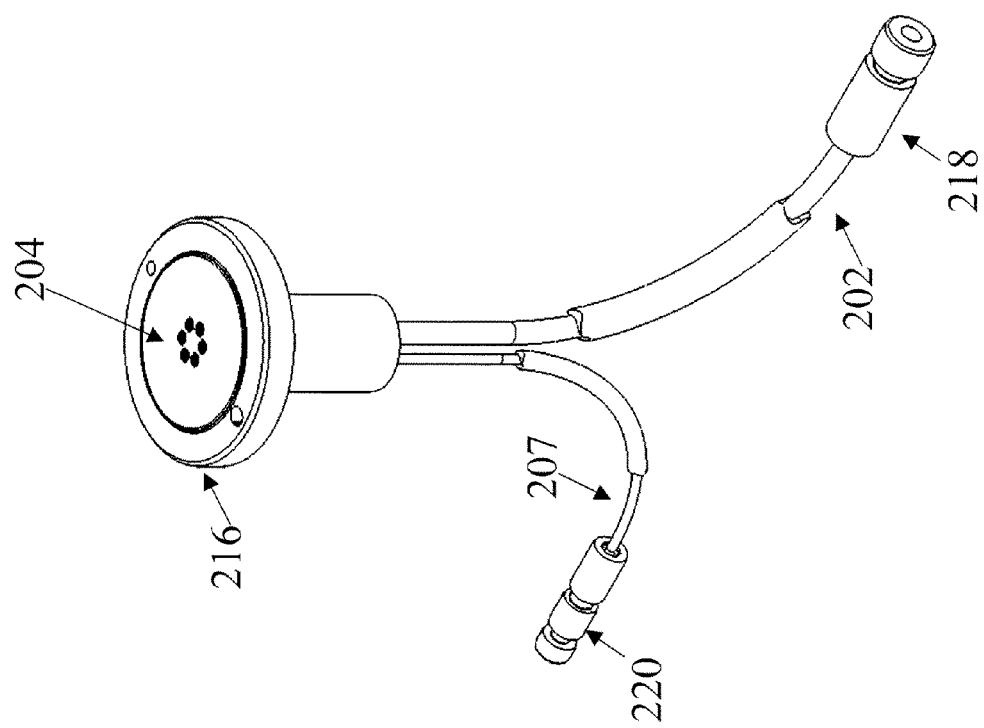
FIG. 16 is a perspective view of elements of a preferred tissue sampling subsystem.

FIGS. 16 through 26 depict elements of an example tissue sampling subsystem 200. Referring to FIG. 16, the tissue sampling subsystem 200 has an optical input 202, a sampling surface 204 which forms a tissue interface that interrogates the tissue and an optical output 207. The subsystem can further include an ergonomic apparatus 210, depicted in FIG. 17, which holds the sampling surface 204 and positions the tissue at the interface. In a preferred subsystem, a device that thermostats the tissue interface is included and, in some embodiments, an apparatus that repositions the tissue on the tissue interface in a repetitive fashion is included. In other embodiments, an index matching fluid can be used to improve the optical interface between the tissue and sampling surface. The improved interface can reduce error and increase the efficiency, thereby improving the net attribute signal. See, e.g., U.S. Pat. Nos. 6,622,032, 6,152,876, 5,823,951, and 5,655,530, which are incorporated herein by reference.

Figure 18:
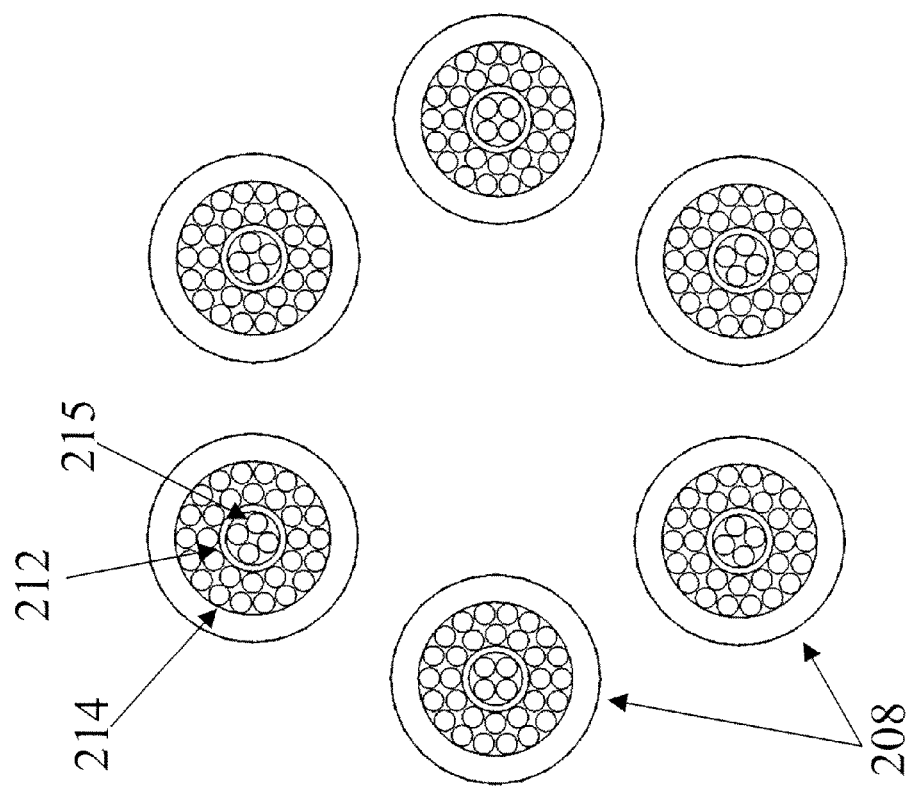
FIG. 18 is a plan view of the sampling surface of the tissue sampling subsystem, showing a preferred arrangement of illumination and collection optical fibers.

The optical input 202 of the tissue sampling subsystem 200 receives radiation from the illumination/modulation subsystem 100 (e.g., light exiting a light pipe) and transfers that radiation to the tissue interface. As an example, the optical input can comprise a bundle of optical fibers that are arranged in a geometric pattern that collects an appropriate amount of light from the illumination/modulation subsystem. FIG. 18 depicts one example arrangement. The plan view depicts the ends of the input and output fibers in a geometry at the sampling surface including six clusters 208 arranged in a circular pattern. Each cluster includes four central output fibers 215 which collect diffusely reflected light from the tissue. Around each grouping of four central output fibers 215 is a cylinder of material 212 which ensures about a 100 μm gap between the edges of the central output fibers 215 and the inner ring of input fibers 214. The 100 μm gap can be important to measuring ethanol in the dermis. As shown in FIG. 18, two concentric rings of input fibers 214 are arranged around the cylinder of material 212. As shown in one example embodiment, 32 input fibers surround four output fibers.

The clustered input and output fibers can be mounted into a cluster ferrule that is mounted into a sampling head 216. The sampling head 216 includes the sampling surface 204 that is polished flat to allow formation of a good tissue interface. Likewise, the input fibers are clustered into a ferrule 218 connected at the input ends to interface with the illumination/modulation subsystem 100. The output ends of the output fibers are clustered into a ferrule 220 for interface with the data acquisition subsystem 300.

Alternatively, the optical input can use a combination of light pipes, refractive and/or reflective optics to transfer input light to the tissue interface. It is important that the input optics of the tissue sampling subsystem collect sufficient light from the illumination/modulation subsystem 100 in order to achieve an acceptable net attribute signal.

Figure 19:
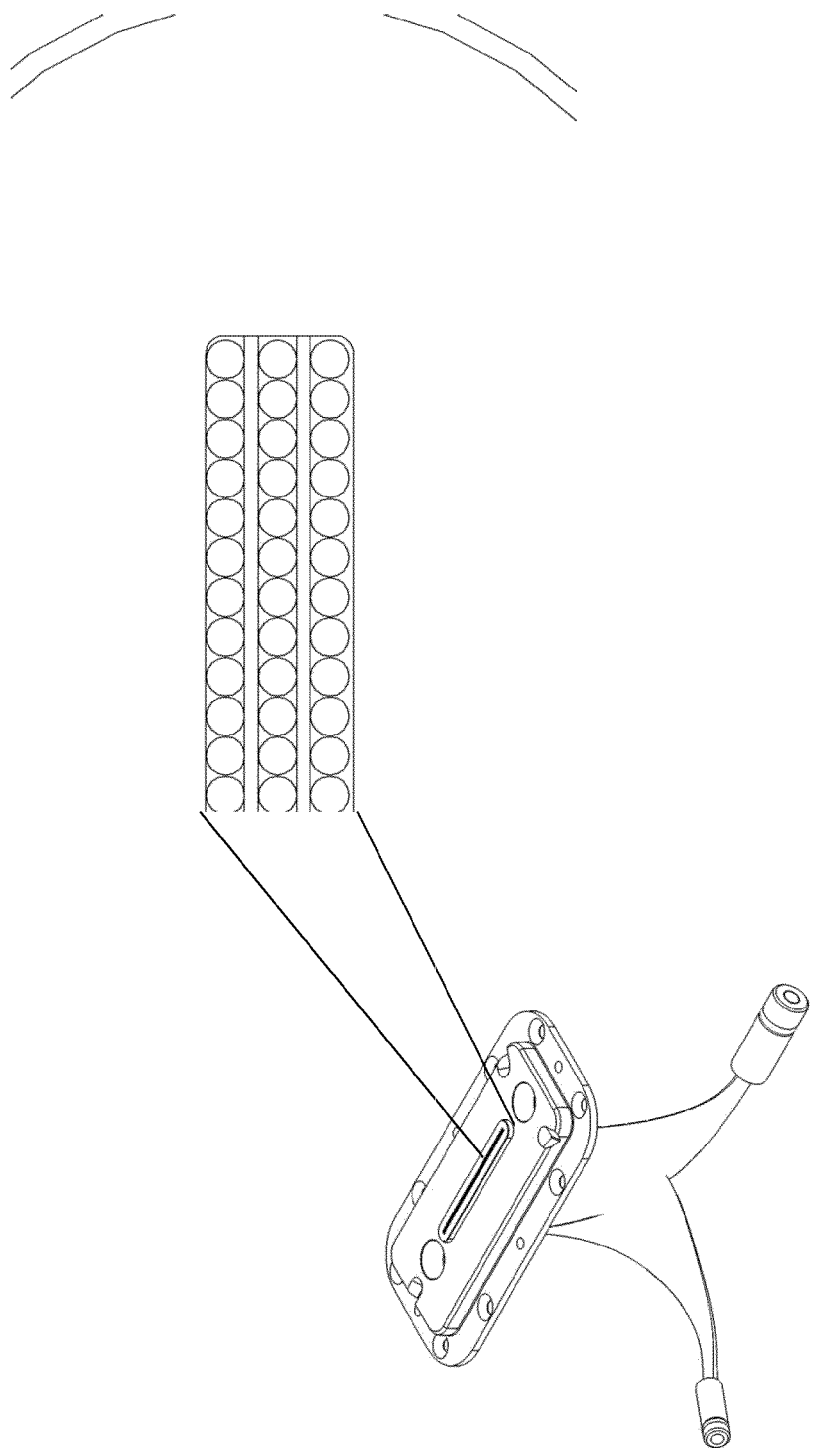
FIG. 19 is an alternative embodiment of the sampling surface of the tissue sampling subsystem.

FIG. 19 demonstrates an alternative to cluster geometries for the sampling subsystem. In this embodiment, the illumination and collection fiber optics are arranged in a linear geometry. Each row can be either for illumination or light collection and can be of any length suitable to achieve sufficient signal to noise. In addition, the number of rows can be 2 or more in order to alter the physical area covered by the sampling subsystem. The total number of potential illumination fibers is dependent on the physical size of emissive area of the light source and the diameter of each fiber. Multiple light sources can be used to increase the number of illumination fibers. The number of collection fibers depends upon the area of the interface to the interferometer subsystem. If the number of collection fibers results in an area larger than the interferometer subsystem interface allows, a light pipe or other homogenizer followed by an aperture can be used to reduce the size of the output area of the sampling subsystem. The purpose of the light pipe or other homogenizer is to ensure that each collection fiber contributes substantially equally to the light that passes through the aperture.

Figure 20:
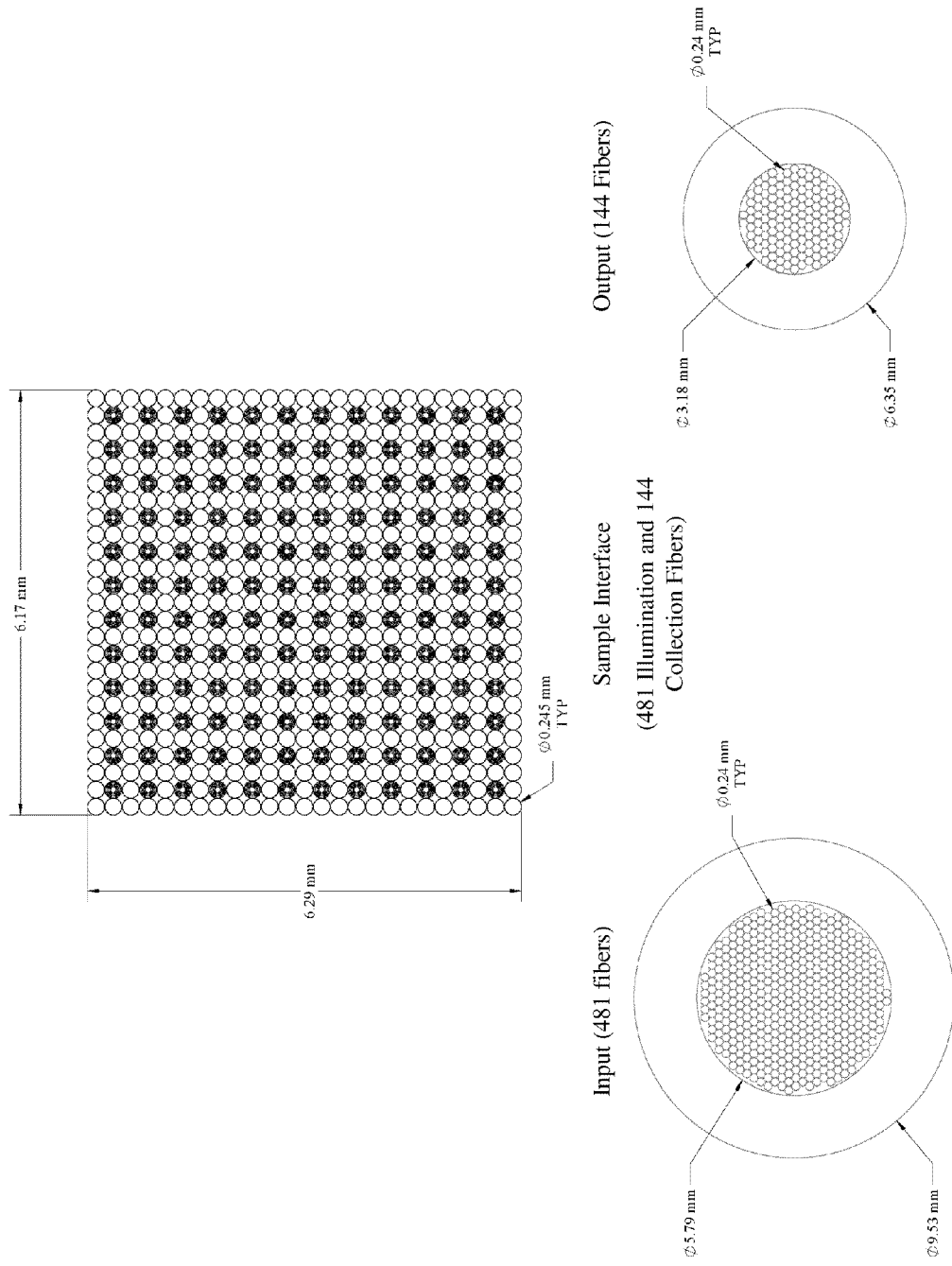
FIG. 20 is an alternative embodiment of the sampling surface of the tissue sampling subsystem.

In some embodiments the sampling subsystem of the present invention, the portion of the optical probe that interacts with the sample can be comprised of a stack of two or more linear ribbons of optical fibers. These arrangements allow the size and shape of the optical probe interface to be designed appropriately for the sample and measurement location (e.g., hand, finger) of interest. FIG. 20 shows an example embodiment of a sampling subsystem based on a linear stack off ribbons. Additional details regarding suitable embodiments for use in the present invention can be found in co-pending U.S. patent application Ser. Nos. 12/185,217 and 12/185,224, each of which is incorporated herein by reference.

Figure 21:
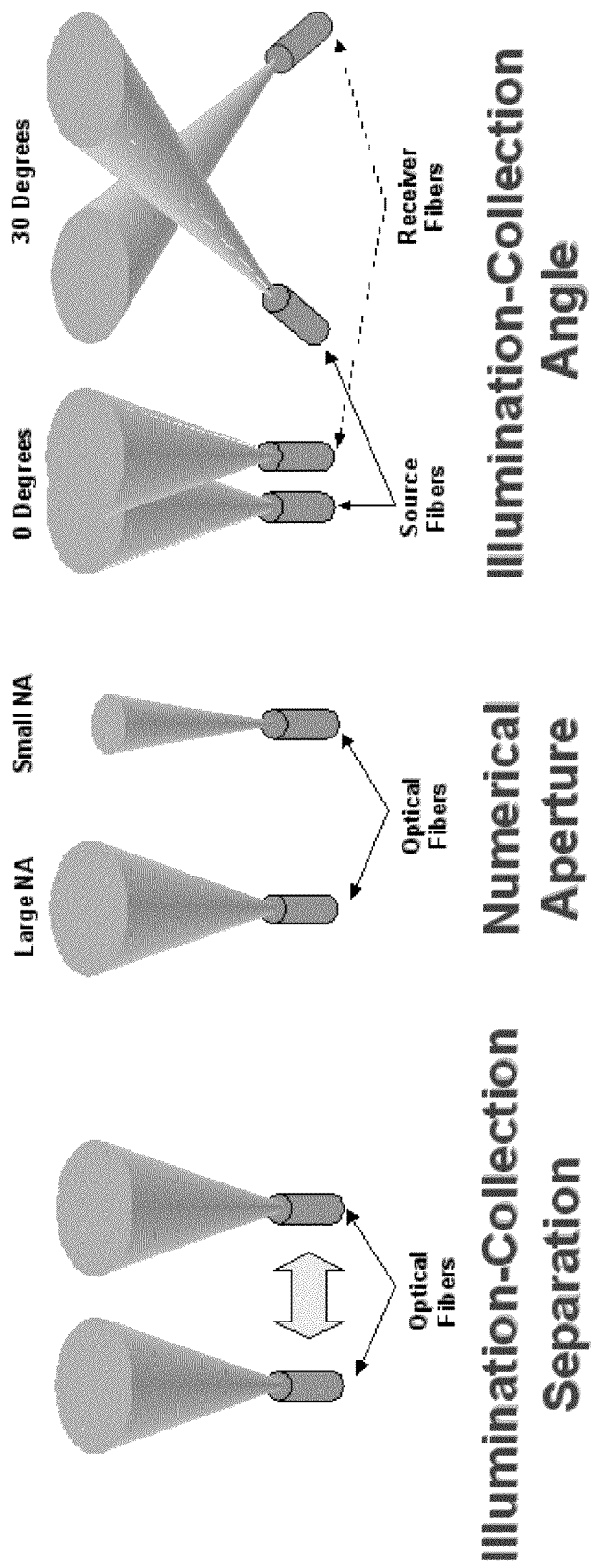
FIG. 21 is a depicts the various aspects of a sampler orientation.
Figure 22:
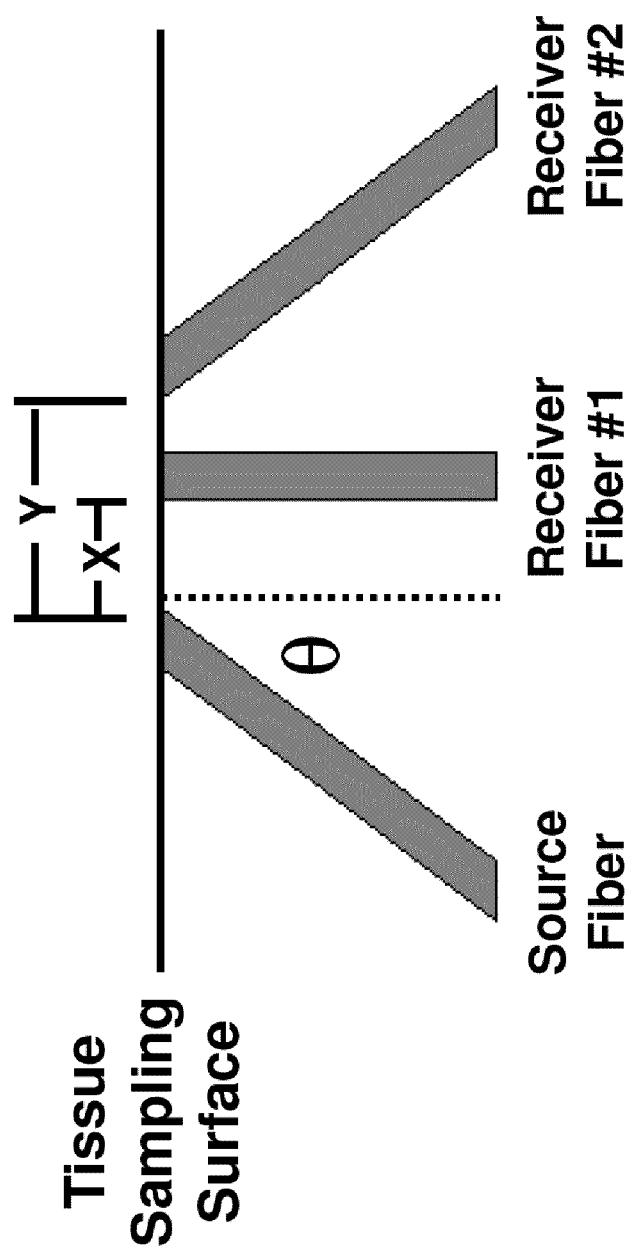
FIG. 22 is a diagramed view of a two-channel sampling subsystem.

The sampling subsystems can also use one or more channels, where a channel refers to a specific orientation of the illumination and collection fibers. An orientation is comprised of the angle of the illumination fiber or fibers, the angle of the collection fiber or fibers, the numerical aperture of the illumination fiber or fibers, the numerical aperture of the collection fiber or fibers, and the separation distance between the illumination and collection fiber or fibers. FIG. 21 is a diagram of parameters that form an orientation. Multiple channels can be used in conjunction, either simultaneously or serially, to improve the accuracy of the noninvasive measurements. FIG. 22 is a diagram of a two channel sampling subsystem. In this example, the two channels are measuring the same tissue structure. Therefore each channel provides a measurement of the same tissue from a different perspective. The second perspective helps to provide additional spectroscopic information that helps to decouple the signals due to scattering and absorption. Referring to FIG. 22, the group of fibers (1 source fiber, 1 receiver fiber #1, and 1 receiver fiber

2 in this example) can be replicated 1 to N times in order to increase the sampler area and improve optical efficiency. Each of the fibers can have a different numerical aperture and angle (θ). The distances between fibers, X and Y, determine the source-receiver separation. Furthermore, an additional source channel can be added that creates a 4-channel sampling subsystem. One skilled in the art recognizes the large number of possible variants on the number and relationship between channels.

In practice, reflectance measurements obtained from a given channel are comprised of many photons that have traveled a range of pathlengths (all photons do not travel the same distance due to scattering effects). The collective behavior of photon pathlength for a given channel can be characterized by a pathlength distribution, which defines the probability as a function of pathlength. The specific design parameters of a sampling channel can strongly influence the pathlength distribution.

In a single channel sampling subsystem, the spectroscopic effects of concentration and pathlength can be similar. In such cases, the combination of multiple channels into a sampling subsystem can provide the ability to decouple the confounding effects of concentration and photon pathlength through tissue. For example, the concentration of water is presumed constant (albeit unknown) for all channels during the acquisition of the spectroscopic signal. The channels are then selected such that they interrogate essentially the same tissue volume but with different pathlength distributions through the tissue. Thus concentration is held constant while pathlengths are varied which allows the isolation of the spectroscopic effect of pathlength on the measurement. The number of channels can be determined by the cost and performance requirements of the system, and can range from 1 to any number of channels.

Figure 23:
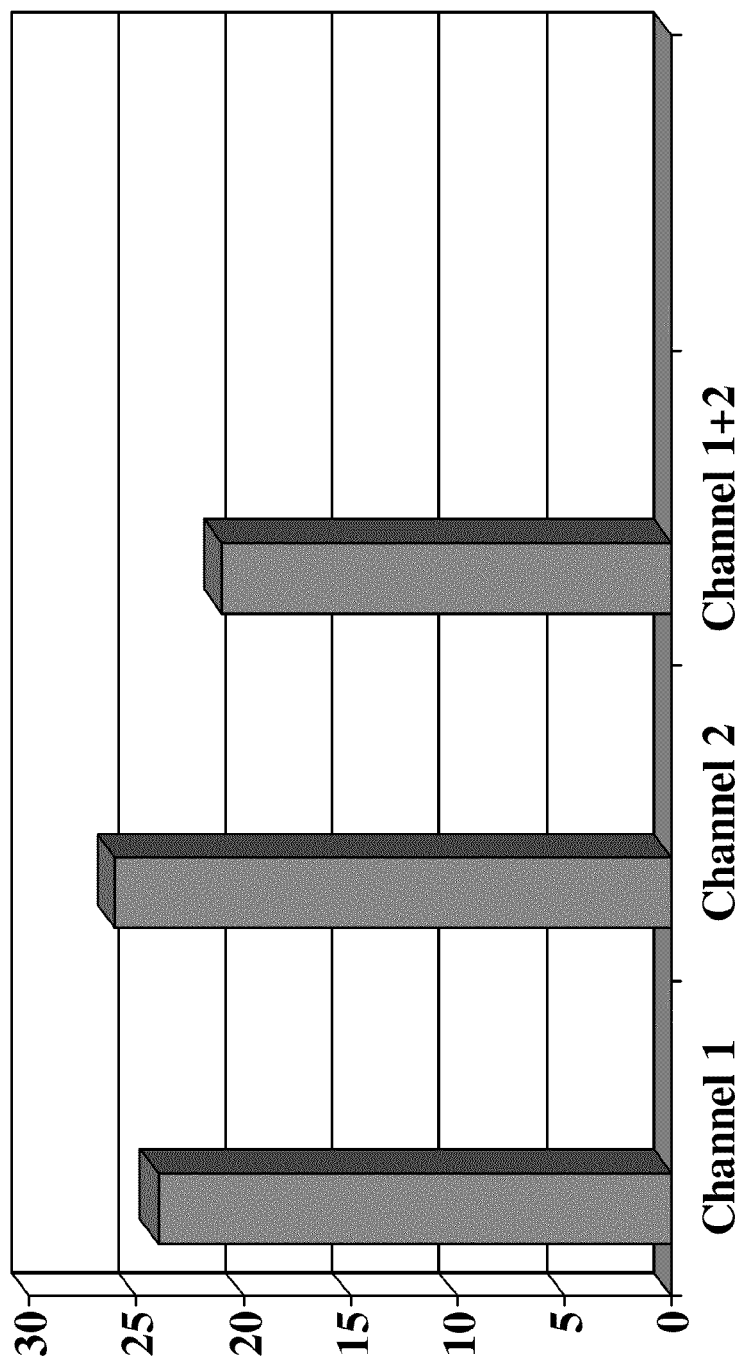
FIG. 23 is a graphical representation showing the benefits of a two-channel sampling subsystem.

FIG. 23 is a bar chart of example of the benefits of a multiple channel sampler that was used for noninvasive glucose measurements. It is clear from the figure that the combination of the two channels provides superior measurement accuracy when compared to either channel individually. While this example uses two channels, additional channels can provide additional information that can further improve the measurement.

Figure 24:
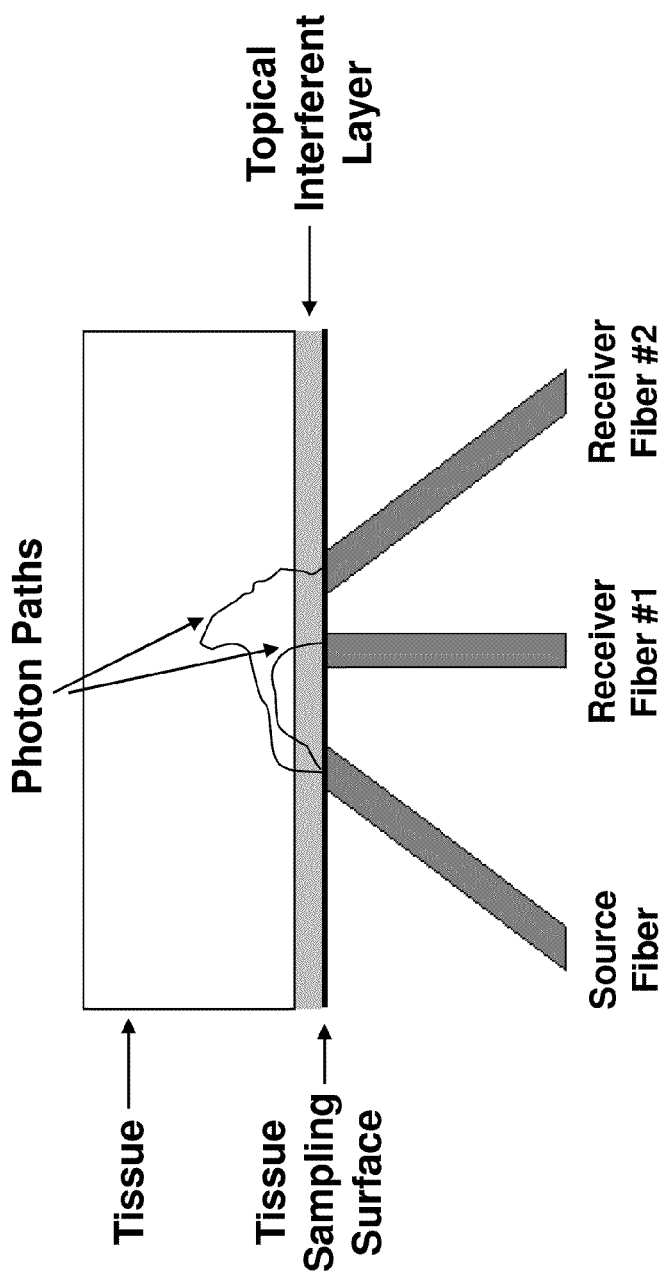
FIG. 24 is a diagramed view of the interface between the sampling surface and the tissue when topical interferents are present on the tissue.

Another aspect of a multiple channel sampling subsystem is the ability to improve detection and mitigation of topical interferents, such as sweat or lotion, present on the sample. FIG. 24 is a diagram of the multiple channel sampling subsystem in the presence of a topical interferent. The figure shows the sampling subsystem at the tissue interface, a layer of topical interferent, and the tissue. In this example the contribution to each channel's measurement due to the topical interferent is identical. This allows the potential to decouple the common topical interferent signal present in both channels from the tissue signal that will be different for the two channels.

The tissue interface can irradiate the tissue in a manner that targets the compartments of the tissue pertinent to the attribute of interest, and can discriminate against light that does not travel a significant distance through those compartments. As an example, a 100-μm gap discriminates against light that contains little attribute information. In addition, the tissue interface can average over a certain area of the tissue to reduce errors due to the heterogeneous nature of the tissue. The tissue sampling interface can reject specular and short pathlength rays and it can collect the portion of the light that travels the desired pathlength through the tissue with high efficiency in order to maximize the net attribute signal of the system. The tissue sampling interface can employ optical fibers to channel the light from the input to the tissue in a predetermined geometry as discussed above. The optical fibers can be arranged in pattern that targets certain layers of the tissue that contain good attribute information.

The spacing, angle, numerical aperture, and placement of the input and output fibers can be arranged in a manner to achieve effective depth targeting. In addition to the use of optical fibers, the tissue sampling interface can use a non-fiber based arrangement that places a pattern of input and output areas on the surface of the tissue. Proper masking of the non-fiber based tissue sampling interface ensures that the input light travels a minimum distance in the tissue and contains valid attribute information. Finally, the tissue sampling interface can be thermostatted to control the temperature of the tissue in a predetermined fashion. The temperature of the tissue sampling interface can be set such that the invention reduces prediction errors due to temperature variation. Further, reference errors are reduced when building a calibration model. These methods are disclosed in U.S. patent application Ser. No. 09/343,800, titled "Method and Apparatus for Non-Invasive Blood Analyte Measurement with Fluid Compartment Equilibration," which is incorporated herein by reference.

In addition to the use of optical fibers, the sampling subsystem can use a non-fiber based arrangement that places a pattern of input and output areas on the sample surface. In some embodiments, the input and output elements of the sampling subsystem can be comprised of a lens system. In a preferred embodiment, the input element and output element comprise a single lens system that is utilized for both input of light from the energy source and the collection of both specularly and diffusely reflected light from the sample. Alternatively, the input element and output element can comprise two lens systems, placed on opposing sides of an analyte-containing sample, wherein light from the energy source is transmitted to the input element and onto the sample, and light transmitted through the analyte-containing sample then passes through the output element to the spectrum analyzer. Proper masking of the non-fiber based tissue sampling interface ensures that the input light travels a minimum distance in the tissue and contains valid attribute information.

Figure 17:
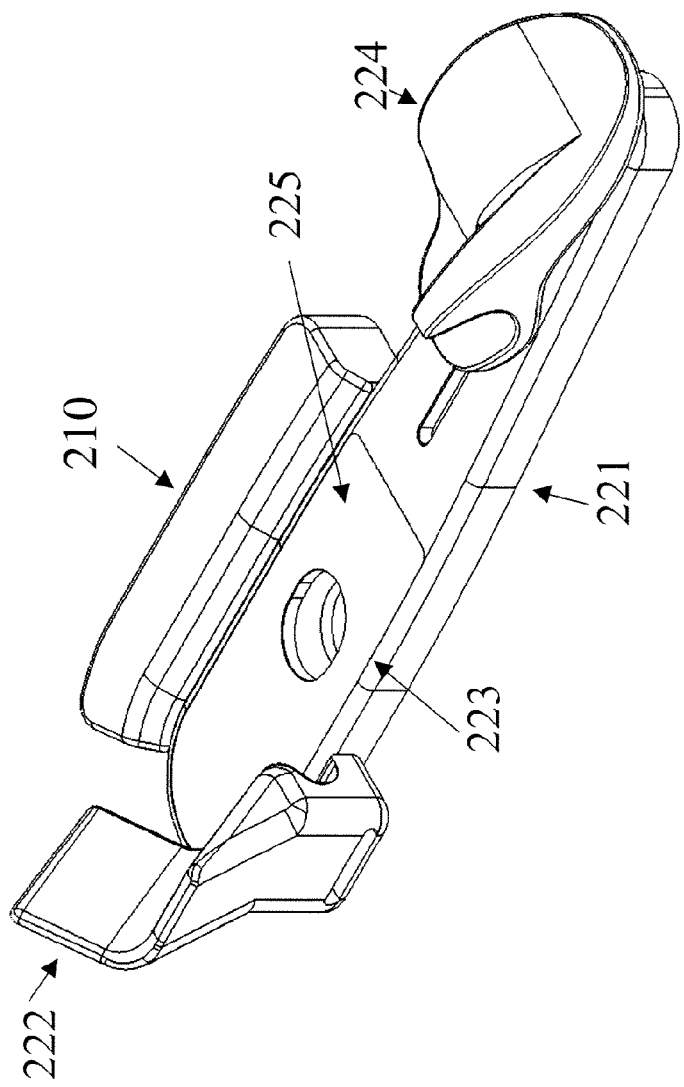
FIG. 17 is a perspective view of an ergonomic apparatus for holding the sampling surface and positioning a tissue surface thereon.

The tissue sampling subsystem can employ an ergonomic apparatus or cradle 210 that positions the tissue over the sampling interface in a reproducible manner. An example ergonomic apparatus 210 is depicted in FIG. 17. In the case of sampling the underside of the forearm, an ergonomic cradle design is essential to ensure good contact with the sampling interface. The ergonomic cradle 210 includes a base 221 having an opening 223 therethrough. The opening is sized for receiving the sample head 216 therein to position the sampling surface 204 generally coplanar with an upper surface 225 of the base 221. The ergonomic cradle 210 references the elbow and upper arm of the subject via a bracket 222 in conjunction with a float-to-fit handgrip 224 to accurately position the forearm on the tissue sampling interface. Careful attention must be given to the ergonomics of the tissue sampling interface or significant sampling error can result.

The example ergonomic cradle 210 is designed such that the forearm of the subject is reliably located over the sampling head 216. The bracket 222 forms an elbow rest that sets the proper angle between the upper arm and the sampling head 216, and also serves as a registration point for the arm. The adjustable hand rest 224 is designed to hold the fingers in a relaxed manner. The hand rest position is adjusted for each subject to accommodate different forearm lengths. In some embodiments, a lifting mechanism is included which raises and lowers the cradle periodically during sampling to break and reform the tissue interface. Reformation of the interface facilitates reduction of sampling errors due to the rough nature and heterogeneity of the skin. Alternate sites, for example fingertips, can also be accommodated using variations of the systems described herein.

Figure 25:
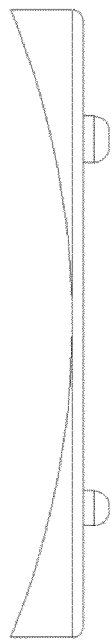
FIG. 25 is a diagramed view of an alternative positioning device for the tissue relative to the sampling surface.
Figure 25:
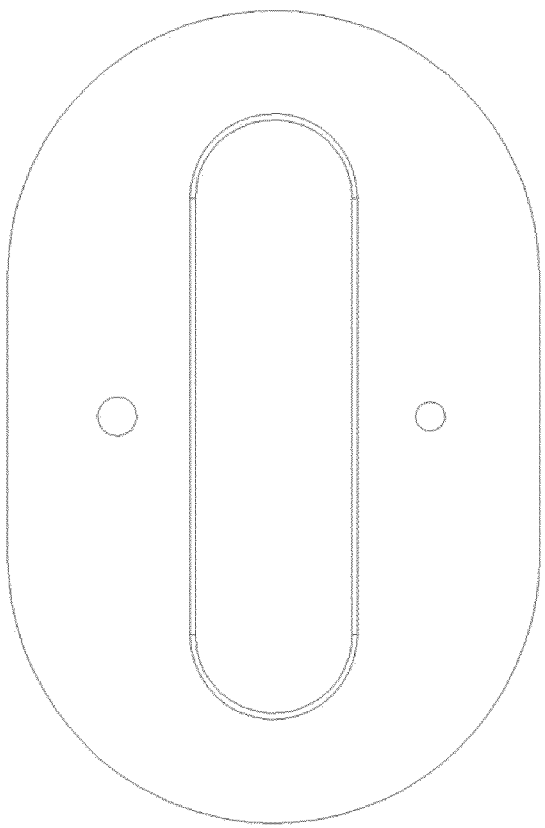
Figure 26:
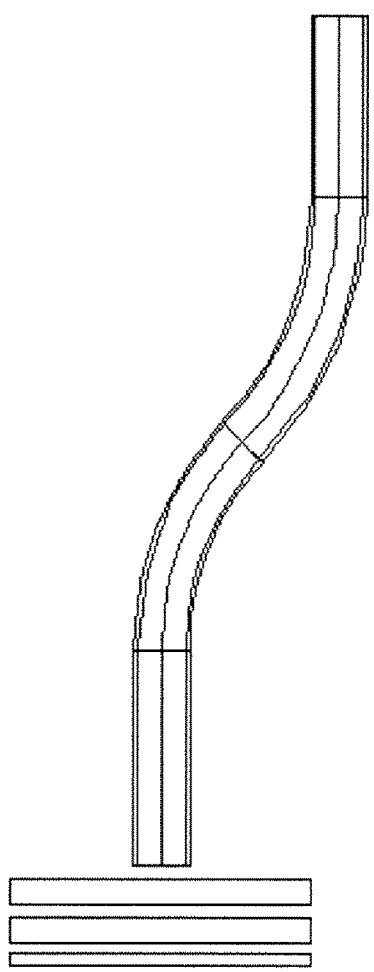
FIG. 26 is a diagramed view of a system of the present invention using a means for spatially and angularly homogenizing emitted radiation.

An alternative to the ergonomic cradle is diagramed in FIG. 25. Instead of a cradle located on the measurement system, the positioning device is located on the tissue. The positioning device can either be reusable or disposable and can be adhered to the tissue with medical adhesive. The positioning device can also include an optically transparent film or other material that prevents physical contact with the sampling subsystem while preserving the desired optical characteristics of the measurement. The positioning device interfaces to the sampling subsystem in a pre-determined manner, such as alignment pins, in order to reproducibly locate the tissue to the sampling subsystem. The positioning device also prevents movement of the tissue relative to the sampling subsystem during the measurement process.

The output of the tissue sampling subsystem 200 transfers the portion of the light not absorbed by the tissue that has traveled an acceptable path through the tissue to the optical detector in the data acquisition subsystem 300. The output of the tissue sampling subsystem 200 can use any combination of refractive and/or reflective optics to focus the output light onto the optical detector. In some embodiments, the collected light is homogenized (see U.S. Pat. No. 6,684,099, "Apparatus and Methods for Reducing Spectral Complexity in Optical Sampling," which is incorporated herein by reference) in order to mitigate for spatial and angular effects that might be sample dependent (see FIG. 26).

As an example application, the noninvasive measurement of alcohol in humans places extreme requirements on the performance of the instrumentation due to the small size of the alcohol absorption spectrum relative to the water absorption of the body. In addition, interferences due to absorption of other spectroscopically active compounds such as collagen, lipids, protein, etc. reduce the useful portions of the alcohol absorption spectrum, yielding a net attribute signal that is small. To first order approximation, 1 mg/dl of alcohol concentration change is equivalent to 7 µAu of spectral variance for the effective pathlength light travels through tissue using the present invention. Therefore, in order to measure alcohol noninvasively with clinically acceptable accuracy, the spectrometer portion of the noninvasive alcohol monitor must have a large signal-to-noise ratio (SNR) and excellent photometric accuracy.

Data Acquisition Subsystem 300

Figure 27:
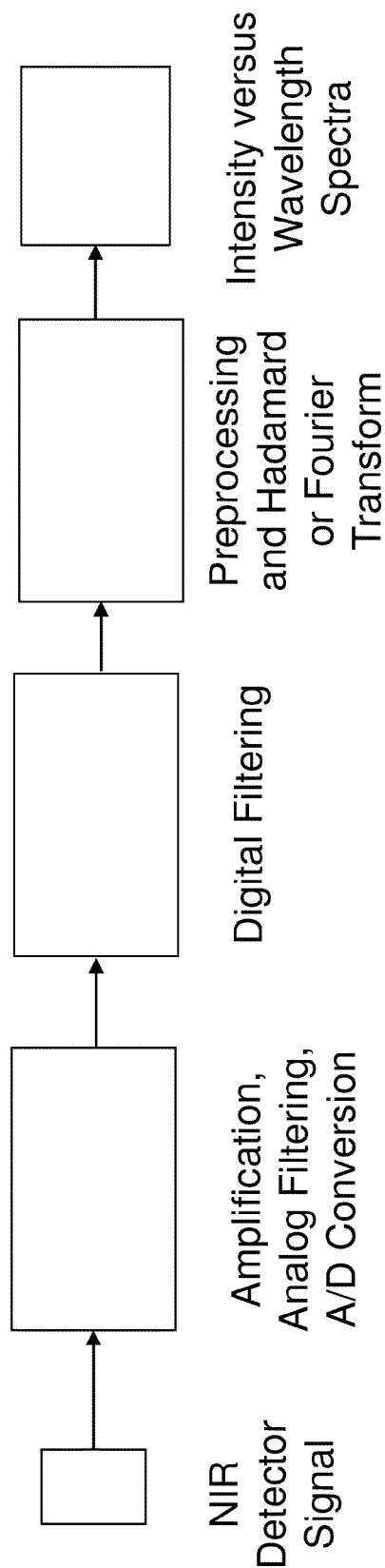
FIG. 27 is a schematic representation of the data acquisition subsystem.

The data acquisition subsystem 300 converts the optical output signal from the sampling subsystem into a digital representation. FIG. 27 is a schematic representation of the data acquisition subsystem. An important aspect of the present invention is that, similar to an interferometric spectrometer, only a single element detector is required to measure all desired wavelengths. Array detectors and their supporting electronics are a significant drawback due to their expensive nature.

The optical detector converts the incident light into an electrical signal as a function of time. Examples of detectors that are sensitive in the spectral range of 1.0 to 2.5 µm include InGaAs, InAs, InSb, Ge, PbS, and PbSe. An example embodiment of the present invention can utilize a 1-mm, thermo-electrically cooled, extended range InGaAs detector that is sensitive to light in the 1.0 to 2.5 µm range. The 2.5 µm, extended range InGaAs detector has low Johnson noise and, as a result, allows Shot noise limited performance for the photon flux emanating from the tissue sampling subsystem. The extended InGaAs detector has peak sensitivity in the 2.0 to 2.5 µm spectral region where three very important alcohol absorption features are located. In comparison with the liquid nitrogen cooled InSb detector, the thermo-electrically cooled, extended range InGaAs can be more practical for a commercial product. Also, this detector exhibits over 120 dbc of linearity in the 1.0 to 2.5 µm spectral region. Alternative detectors can be suitable if the alcohol measurement system utilizes alternative wavelength regions. For example, a silicon detector can be suitable if the wavelength range of interest were within the 300-1100 nm range.

Any photodetector can be used with the present invention as long as the given photodetector satisfies basic sensitivity, noise and speed requirements. A suitable photodetector can have a shunt resistance greater than 6000 ohms, a terminal capacitance less than 6 nano farads and a minimum photo-sensitivity of 0.15 amps per watt over the 1.0 to 2.5 micron spectral region. In addition, the photodetector can have a cut-off frequency greater than or equal to 1000 hertz. The shunt resistance of the photodetector defines the Johnson or thermal noise of the detector. The Johnson noise of the detector must be low relative to the photon flux at the detector to ensure Shot noise limited performance by the detector. The terminal capacitance governs the cut-off frequency of the photodetector and may also be a factor in the high frequency noise gain of the photodetector amplifier. The photo sensitivity is an important factor in the conversion of light to an electrical current and directly impacts the signal portion of the SNR equation.

The remainder of the data acquisition subsystem 300 amplifies and filters the electrical signal from the detector and then converts the resulting analog electrical signal to its digital representation with an analog to digital converter, digital filtering, and re-sampling of the digital signal from equal time spacing to equal position spacing. The analog electronics and ADC must support the high SNR and linearity inherent in the signal. To preserve the SNR and linearity of the signal, the data acquisition subsystem 300 can support at least 100 dbc of SNR plus distortion. The data acquisition subsystem 300 can produce a digitized representation of the signal. In some embodiments, a 24-bit delta-sigma ADC can be operated at 96 or 192 kilohertz. If system performance requirements permit, alternate analog to digital converters can be used in which the sample acquisition is synchronized with the light source modulation rather than captured at equal time intervals. The digitized signal can be passed to an embedded computer subsystem 400 for further processing, as discussed below.

Further, the data acquisition subsystem 300 can utilize a constant time sampling, dual channel, delta-sigma analog-to-digital converter (ADC) to support the SNR and photometric accuracy requirements of the present noninvasive analyte measurement. In some embodiments, the delta-sigma ADC utilized supports sampling rates of over 100 kHz per channel, has a dynamic range in excess of 117 dbc and has total harmonic distortion less than −105 dbc. In a system that has only one channel of signal to digitize (instead of the two more common in delta-sigma ADC's), the signal can be passed into both inputs of the ADC and averaged following digitization. This operation can help to reduce any uncorrelated noise introduced by the ADC.

The constant time sampling data acquisition subsystem 300 has several distinct advantages over other methods of digitizing signals. These advantages include greater dynamic range, lower noise, reduced spectral artifacts; detector noise limited operation and simpler and less expensive analog electronics. In addition, the constant time sampling technique allows digital compensation for frequency response distortions introduced by the analog electronics prior to the ADC. This includes non-linear phase error in amplification and filtering circuits as well as the non-ideal frequency response of the optical detector. The uniformly sampled digital signal allows for the application of one or more digital filters whose cumulative frequency response is the inverse of the analog electronics' transfer function (see, e.g., U.S. Pat. No. 7,446,878, which is incorporated herein by reference).

Computing Subsystem 400

Figure 28:
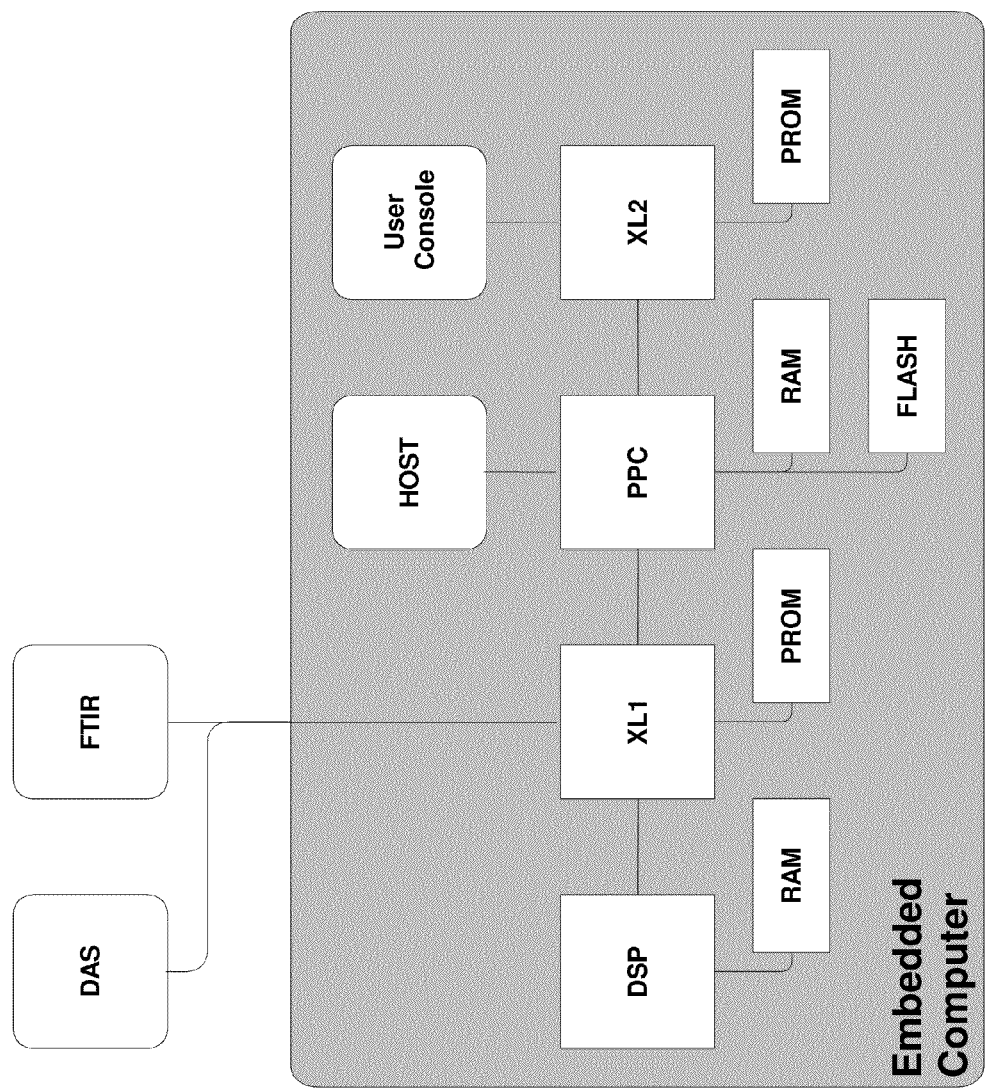
FIG. 28 is a schematic representation that shows the various aspects of the computing subsystem.

The computing subsystem 400 performs multiple functions such as converting the digitized data obtained from the data acquisition subsystem 300 to single beam spectra, performing spectral outlier checks on the single beam spectra, spectral preprocessing in preparation for prediction of the attribute of interest, prediction of the attribute of interest, system status checks, all display and processing requirements associated with the user interface, and data transfer and storage. FIG. 28 is a schematic representation that shows the various aspects of a suitable computing subsystem. In some embodiments, the computing subsystem is contained in a dedicated personal computer or laptop computer that is connected to the other subsystems of the invention. In other embodiments, the computing subsystem is a dedicated, embedded computer.

After converting the digitized data from the detector to single beam spectra, the computer system can check the single beam spectra for outliers or bad scans. An outlier sample or bad scan is one that violates the hypothesized relationship between the measured signal and the properties of interest. Examples of outlier conditions include conditions where the calibrated instrument is operated outside of the specified operating ranges for ambient temperature, ambient humidity, vibration tolerance, component tolerance, power levels, etc. In addition, an outlier can occur if the composition or concentration of the sample is different than the composition or concentration range of the samples used to build the calibration model. The calibration model will be discussed as part of the calibration subsystem later in this disclosure. Any outliers or bad scans can be deleted and the remaining good spectra can be averaged together to produce an average single beam spectrum for the measurement. The average single beam spectrum can be converted to absorbance by taking the negative base 10 logarithm (log 10) of the spectrum. The absorbance spectrum can be scaled by a single beam spectrum to renormalize the noise.

The scaled absorbance spectrum can be used to determine the attribute of interest in conjunction with a calibration model that is obtained from the calibration subsystem 500. After determination of the attribute of interest, the computing subsystem 400 can report the result, e.g., to the subject, to an operator or administrator, to a recording system, or to a remote monitor. The computing subsystem 400 can also report the level of confidence in the goodness of the result. If the confidence level is low, the computing subsystem 400 can withhold the result and ask the subject to retest. If required, additional information can be conveyed that directs the user to perform a corrective action. See, e.g., US Appl. Pub. No. 2004/0204868, which is incorporated herein by reference. The results can be reported visually on a display, by audio and/or by printed means. Additionally, the results can be stored to form a historical record of the attribute. In other embodiments, the results can be stored and transferred to a remote monitoring or storage facility via the internet phone line, or cell phone service.

The computing subsystem 400 includes a central processing unit (CPU), memory, storage, a display and preferably a communication link. An example of a CPU is the Intel Pentium microprocessor. The memory can be, e.g., static random access memory (RAM) and/or dynamic random access memory. The storage can be accomplished with non-volatile RAM or a disk drive. A liquid crystal display can be suitable. The communication link can be, as examples, a high speed serial link, an Ethernet link, or a wireless communication link. The computer subsystem can, for example, produce attribute measurements from the received and processed interferograms, perform calibration maintenance, perform calibration transfer, run instrument diagnostics, store a history of measured alcohol concentrations and other pertinent information, and in some embodiments, communicate with remote hosts to send and receive data and new software updates.

The computing subsystem 400 can also contain a communication link that allows transfer of a subject's alcohol measurement records and the corresponding spectra to an external database. In addition, the communication link can be used to download new software to the computer and update the multivariate calibration model. The computer system can be viewed as an information appliance. Examples of information appliances include personal digital assistants, web-enabled cellular phones and handheld computers.

Calibration Subsystem 500

A calibration model is used in connection with the spectral information in order to obtain alcohol measurements. In some embodiments, the calibration model is formed by acquiring blood reference measurements and contemporaneous spectroscopic data on multiple subjects in a wide variety of environmental conditions. In these embodiments, spectroscopic data can be acquired from each subject over a range of blood alcohol concentrations. In other embodiments, a hybrid calibration model can be used to measure the alcohol concentrations of subject spectra. In this case, the term hybrid model denotes that a partial least squares (PLS) calibration model was developed using a combination of in vitro and in vivo spectral data. The in vitro portion of the data can be a 0.1 mm pathlength transmission spectrum of 500 mg/dL alcohol in water measured using the noninvasive measurement system configured for transmission measurements. The transmission spectrum can be ratioed to a 0.1 mm pathlength transmission spectrum of water, converted to absorbance, and normalized to unit pathlength and concentration.

Light propagation through tissue is a complex function of the diffuse reflectance optical tissue sampler design, physiological variables, and wavenumber. Consequently, the pathlength of light through tissue has a wavenumber dependence that is not encountered in scatter-free transmission measurements. In order to account for the wavenumber dependence, the interaction of the optical tissue sampler with the scattering properties of human tissue can be modeled via Monte-Carlo simulation using a commercial optical ray-tracing software package (TracePro). Using the resulting model of the photon-tissue interactions, an estimate of the effective pathlength of light through the dermis and subcutaneous tissue layers as a function of wavenumber can be generated. The effective pathlength ($l_{\mathit{eff}}$) is defined as $$l_{\mathit{eff}}(v) = \frac{\sum_{i=1}^{N} l_i \exp(-\mu_a(v) l_i)}{\sum_{i=1}^{N} l_i}, \quad (\text{eq. 1})$$

where ν is wavenumber, $l_i$ is the pathlength traversed by the $i^{th}$ ray in the Monte Carlo simulation [mm], N is the total number of rays in the simulation, and $\mu_a$ is the (wavenumber-dependent) absorption coefficient [mm$^{-1}$]. Due to its large absorption in vivo, water is the only analyte that has a significant effect on the effective pathlength. Therefore, for the purposes of the effective pathlength calculation, the absorption coefficients used can be those of water at physiological concentrations. The alcohol absorbance spectrum (as measured in transmission) can then be scaled by the computed path function to form a corrected alcohol spectrum representative of the wavenumber dependent pathlength measured by the diffuse reflectance optical sampler.

The Beer-Lambert law is commonly invoked in absorption spectroscopy to elucidate the relationship between the measured signal and the property of interest (alcohol concentration). For a sample containing a single absorbing analyte that is spectroscopically measured at a single wavelength, the Beer-Lambert Law can be expressed as:

$$A_\lambda = \in_\lambda lc \quad \text{(eq. 2)}$$

where $A_\lambda$ is the absorption of the sample at wavelength λ, $\in_\lambda$ is the absorptivity of the single analyte in the sample at wavelength λ, l is the pathlength that the light travels through the sample, and c is the concentration of the analyte. As such, the Beer-Lambert Law states that a linear relationship between the absorbance of the sample and the concentration of the analyte in the sample. In order to determine the concentration of the analyte in practice, $\in_\lambda$ and l must be known quantities such that upon experimental measurement of $A_\lambda$, the concentration (c) is the only remaining unknown.

The Beer-Lambert Law can be extended to samples containing more than one analyte; however, additional wavelengths must be measured in order to determine the property of interest. For example, a sample containing 2 analytes must be measured at two wavelengths according to the following equations:

$$A_{\lambda 1} = \in_{\alpha\lambda 1} lc_\alpha + \in_{\beta\lambda 1} lc_\beta \text{ and } A_{\lambda 2} = \in_{\alpha\lambda 2} lc_\alpha + \in_{\beta\lambda 2} lc_\beta \quad \text{(eqs. 3 and 4)}$$

where α and β represent the 2 analytes and λ1 and λ2 are the two measured wavelengths. From a mathematical perspective, the number of unknowns (concentrations) in the system of equations can never exceed the number of equations, thus necessitating the measurement of additional wavelengths (to add more equations) and complete characterization of the sample (all ∈ terms must be separately determined and the pathlength l must be known). This places a significant burden on the direct application of the Beer-Lambert Law and similar direct solution methods such as Classical Least Squares (CLS) as all analytes present in the sample must be identified and their absorptivities determined.

Spectral measurements of complex media, such as human tissue, can be comprised of many overlapping spectral signatures from a large number of chemical analytes. While feasible in some situations depending on the measurement objectives, the Beer-Lambert/CLS class of approaches can be difficult to implement due to the large number of variables. In such cases, alternative multivariate analysis methods can be used to decouple the signal of the analyte of interest from the signals of other analytes in the system (interferents). Partial Least Squares (PLS) regression is a well established multivariate analysis method that has been applied to quantitative analysis of spectroscopic measurements and will be used for demonstrative purposes for the remainder of the disclosure. However, other multivariate analysis methods such as Principal Components Regression (PCR), Ridge Regression, Multiple Linear Regression (MLR) and Neural Networks are also suitable for the present invention. One skilled in the art will recognize that other methods of similar functionality can also be applicable.

In PLS regression, a set of spectroscopic calibration measurements is acquired where each spectroscopic measurement has a corresponding reference value for the property of interest (e.g., blood alcohol concentration). The calibration spectral data are then decomposed into a series of factors (spectral shapes that are sometimes called loading vectors or latent variables) and scores (the magnitude of the projection of each spectrum onto a given factor) such that the squared covariance between the reference values and the scores on each successive PLS loading vector is maximized. The scores of the calibration spectra are then regressed onto the reference values in a multiple linear regression (MLR) step in order to calculate a set of spectral weights (one weight per wavenumber in the spectra) that minimizes the analyte measurement error of the calibration measurements in a least-squares sense. These spectral weights are called the regression vector of the calibration model. Once the calibration model is established, subsequent measurements are obtained by calculating the vector dot product of the regression vector and each measured spectrum.

An advantage of PLS and similar methods (commonly referred to as indirect methods) is that the ∈ terms in the Beer-Lambert Law (and thus the complete composition of the sample) do not need to be known. Furthermore, inverse methods tend to be more robust at dealing with nonlinearities in the spectral measurement such as those caused by instrumental drift, light scattering, environmental noise, and chemical interactions.

Functionally, the goal of the multivariate calibration (PLS or otherwise) in the present invention is to determine the part of the spectroscopic signal of alcohol that is effectively orthogonal (contravariant) to the spectra of all interferents in the sample. This part of the signal is referred to as the net attribute signal and can be calculated using the regression vector (b) described above using equation 4. If there are no interfering species, the net attribute spectrum is equal to the pure spectrum of alcohol. If interfering species with similar spectra to the analyte are present, the net attribute signal will be reduced relative to the entire spectrum. The concept of net attribute signal for a three-analyte system is depicted graphically in FIG. 15.

$$NAS = \frac{\hat{b}}{\|\hat{b}\|_2^2} \quad \text{(eq. 5)}$$

In other embodiments of the present invention, a hybrid calibration model can be used to measure the alcohol concentrations of subject spectra. The term hybrid model denotes that a partial least squares (PLS) calibration model was developed using a combination of in vitro and in vivo spectral data. The in vitro portion of the data can comprise a 0.1 mm pathlength transmission spectrum of 500 mg/dL alcohol in water measured using a noninvasive measurement system configured for transmission measurements. The transmission spectrum can be ratioed to a 0.1 mm pathlength transmission spectrum of water, converted to absorbance, and normalized to unit pathlength and concentration.

Figure 29:
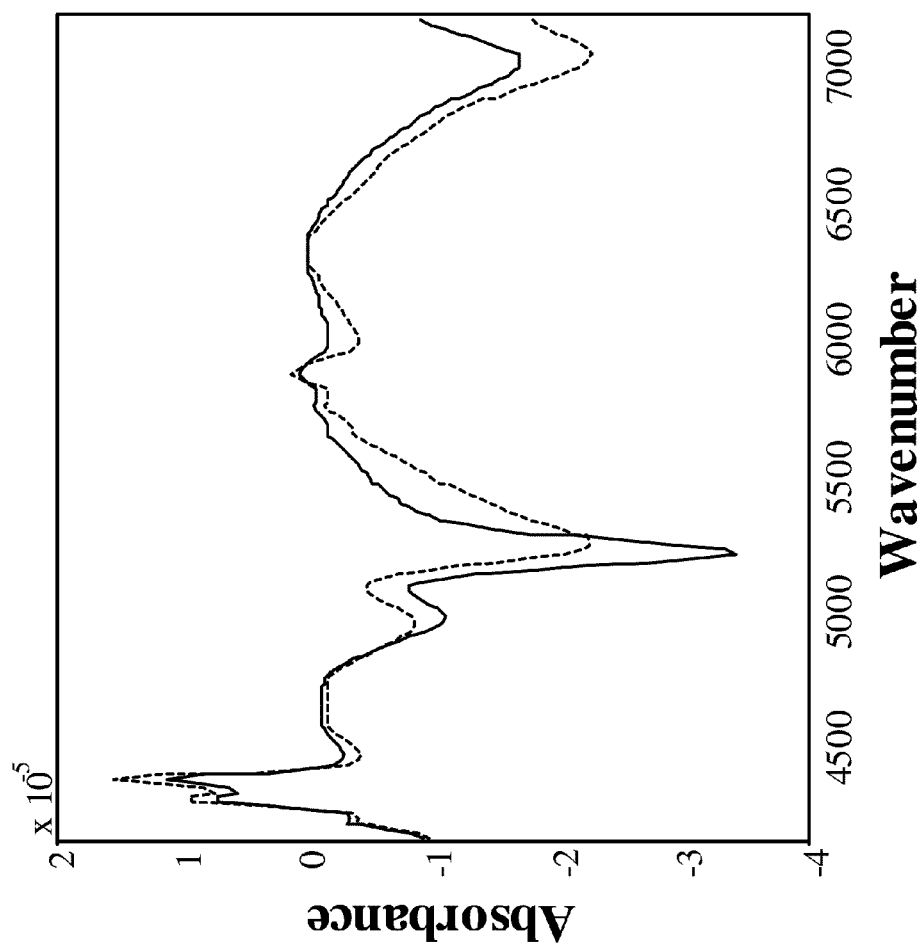
FIG. 29 is the spectrum of water before and after path length correction to account for photon propagation through tissue.

The alcohol absorbance spectrum (as measured in transmission) can then be scaled by a computed effective path function (see equation 1) to form a corrected alcohol spectrum representative of the wavenumber dependent pathlength measured by the diffuse reflectance optical sampler. FIG. 29 shows the alcohol absorbance spectrum before and after correction by the path function. This corrected spectrum formed the base spectrum for the mathematical addition of alcohol to the calibration spectra.

Figure 30:
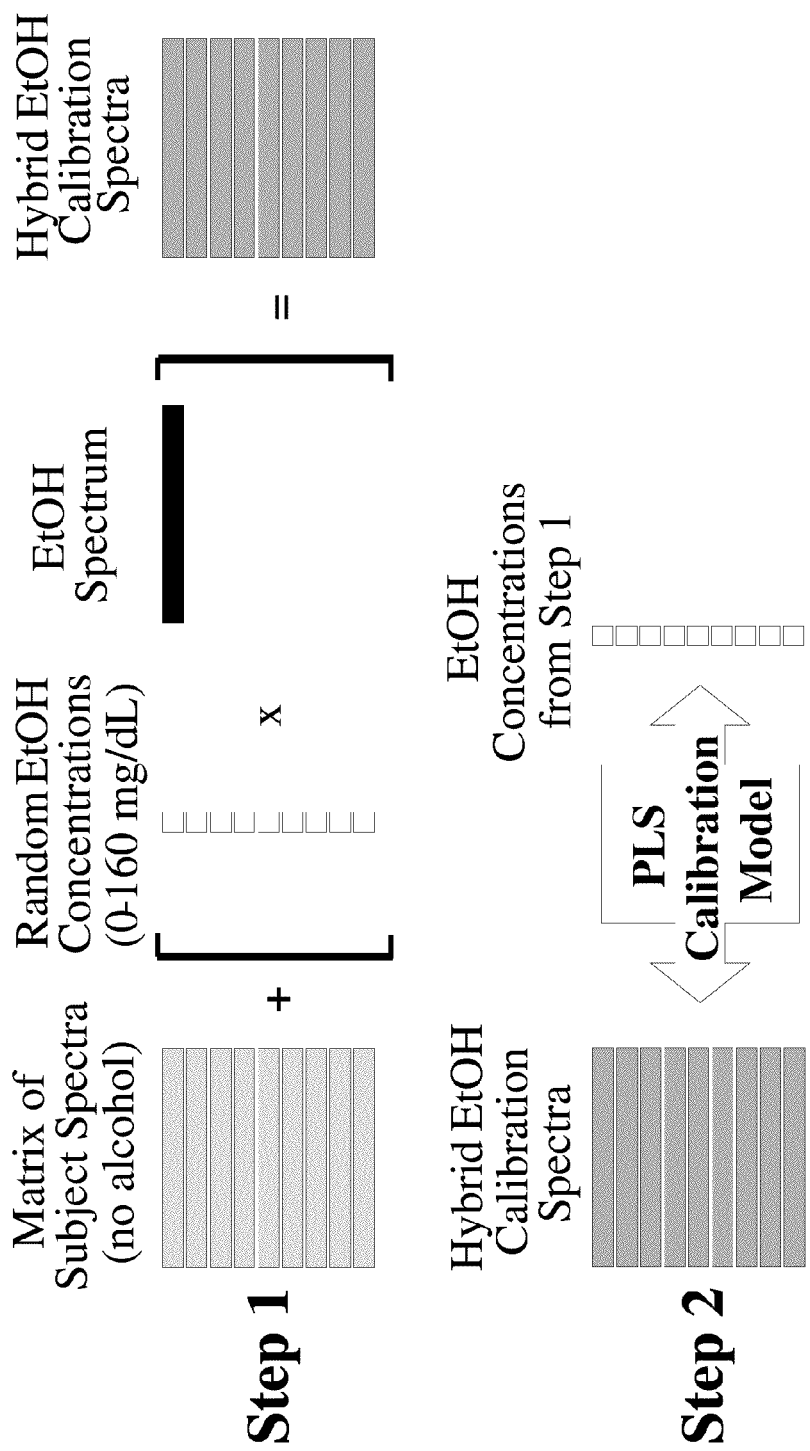
FIG. 30 is a diagram of the hybrid calibration formation process.

The in vivo data can comprise noninvasive tissue spectra collected from persons who had not consumed alcohol. A hybrid model can be formed by adding the alcohol pure component spectrum, weighted by various alcohol "concentrations" (ranging from 0 to 160 mg/dL), to the noninvasive tissue spectral data. The PLS calibration model can be built by regressing the synthetic alcohol concentrations on the hybrid spectral data. FIG. 30 is a schematic representation of a hybrid calibration formation process.

The use of hybrid calibration models, rather than calibration models built from spectra acquired from subjects who have consumed alcohol, can provide significant advantages. The hybrid modeling process makes it possible to generate calibration spectra that contain higher concentrations (e.g., up to 160 mg/dL) of alcohol than would be considered safe for consumption in a human subject study (120 mg/dL is considered a safe upper limit). This can result in a stronger calibration with a wider range of analyte concentrations that is able to predict higher alcohol concentrations more accurately. This can be important because alcohol concentrations observed in the field can be more than double the maximum safe dosage in a clinical research setting. The hybrid calibration process also allows the prevention of correlations between alcohol and the spectral interferents in tissue. For example, the random addition of alcohol signal to the calibration spectra prevents alcohol concentration from being correlated with water concentration. Thus, the hybrid approach prevents the possibility that the measurement could spuriously track changes in tissue water content instead of alcohol concentration.

Alternative calibration strategies can be used in place of, or in conjunction with, the above described methods. For example, in some embodiments biometric enrollment information is acquired from each person to be measured on the device in the future. In such cases, the enrollment measurements can also be used to improve the accuracy and precision of the alcohol or substance of abuse measurement. In this scenario, the calibration spectra are mean-centered by subject (all spectra from a subject are located, the mean of those spectra is subtracted from each, and the "mean centered" spectra are returned to the spectral set). In this manner, the majority of inter-subject spectral differences caused by variations in physiology are removed from the calibration measurements and the range of spectral interferents correspondingly reduced. The centered spectra and associated analyte reference values (blood alcohol concentrations) are then presented to a multivariate analysis method such as partial least squares regression. This process is sometimes referred to as generating an "enrolled", "generic", or "tailored" calibration. Additional details on this approach are described in U.S. Pat. No. 6,157,041, titled "Methods and Apparatus for Tailoring Spectroscopic Calibration Models," the disclosure of which is incorporated by reference.

In practice, once a future, post calibration, subject is enrolled on a noninvasive device their enrollment spectrum can be subtracted from subsequent measurements prior to determining the alcohol or substance of abuse concentration using the generic calibration model. Similar to the mean-centering by subject operation of the calibration spectra, the subtraction of the enrollment spectrum removes the average spectroscopic signature of the subject while preserving the signal of the attribute of interest (alcohol or substance of abuse). In some embodiments, significant performance advantages can be realized relative to the use of a non-generic calibration method.

Once formed, it is desirable that a calibration remain stable and produce accurate attribute predictions over an extended period of time. This process is referred to as calibration maintenance and can be comprised of multiple methods that can be used individually or in conjunction. The first method is to create the calibration in a manner that inherently makes it robust. Several different types of instrumental and environmental variation can affect the prediction capability of a calibration model. It is possible and desirable to reduce the magnitude of the effect of instrumental and environmental variation by incorporating this variation into the calibration model.

It is difficult, however, to span the entire possible range of instrument states during the calibration period. System perturbations can result in the instrument being operated outside the space of the calibration model. Measurements made while the instrument is in an inadequately modeled state can exhibit prediction errors. In the case of in vivo optical measurements of medically significant analytes, these types of errors can result in erroneous measurements that degrade the utility of the system. Therefore it is often advantageous to use additional calibration maintenance techniques during the life of the instrument in order to continually verify and correct for the instrument's status.

Examples of problematic instrument and environmental variation include, but are not limited to: changes in the levels of environmental interferents such as water vapor or $CO_2$ gas, changes in the alignment of the instrument's optical components, fluctuations in the output power of the instrument's illumination system, and changes in the spatial and angular distribution of the light output by the instrument's illumination system.

Calibration maintenance techniques are discussed in U.S. Pat. No. 6,983,176, "Optically Similar Reference Samples and Related Methods for Multivariate Calibration Models Used in Optical Spectroscopy"; U.S. Pat. No. 7,092,832, "Adaptive Compensation for Measurement Distortions in Spectroscopy"; U.S. Pat. No. 7,098,037, "Accommodating Subject and Instrument Variations in Spectroscopic Determinations"; and U.S. Pat. No. 7,202,091, "Optically Similar Reference Samples", each of which is incorporated herein by reference. In some of the disclosed methods, an environmentally inert non-tissue sample, such as an integrating sphere, that may or may not contain the attribute of interest is used in order to monitor the instrument over time. The sample can be incorporated into the optical path of the instrument or interface with the sampling subsystem in a manner similar to that of tissue measurements. The sample can be used in transmission or in reflectance and can contain stable spectral features or contribute no spectral features of its own. The material can be a solid, liquid, or gel material as long as its spectrum is stable or predicable over time. Any unexplained change in the spectra acquired from the sample over time indicate that the instrument has undergone a perturbation or drift due to environmental effects. The spectral change can then be used to correct subsequent tissue measurements in humans in order to ensure and accurate attribute measurement.

Another means for achieving successful calibration maintenance is to update the calibration using measurements acquired on the instrument over time. Usually, knowledge of the reference value of the analyte property of interest is required in order to perform such an update. However, in some applications, it is known that the reference value is usually, but not always, a specific value. In this case, this knowledge can be used to update the calibration even though the specific value of the analyte property is not known for each measurement. For example, in alcohol screening in residential treatment centers, the vast majority of measurements are performed on individuals that have complied with their alcohol consumption restrictions and therefore have an alcohol concentration of zero. In this case, the alcohol concentration measurement or the associated spectrum obtained from the device of the present invention can be used in conjunction with a presumed zero as a reference value. Thus, the calibration can be updated to include new information as it is acquired in the field. This approach can also be used to perform calibration transfer as measurements with presumed zeros can be used at the time of system manufacture or installation in order to remove any system-specific bias in the analyte property measurements of interest. The calibration maintenance update or calibration transfer implementation can be accomplished by a variety of means such as, but not limited to, orthogonal signal correction (OSV), orthogonal modeling techniques, neural networks, inverse regression methods (PLS, PCR, MLR), direct regression methods (CLS), classification schemes, simple median or moving windows, principal components analysis, or combinations thereof.

Wavelength axis stability can be an important aspect of calibration maintenance. The previously discussed etalon and grating based methods for tuning the emission wavelengths of light sources are equally suitable to ensuring wavelength stability over time. In some embodiments, however, stabilized light source temperature via a temperature control circuit, stabilized light source drive current, or light source drive voltage can be sufficient to achieve the desired emission wavelength stability. In other embodiments, combinations of the above methods are used to achieve the desired stability.

Once a calibration is formed, it is often desirable to transfer the calibration to all existing and future units. This process is commonly referred to as calibration transfer. While not required, calibration transfer prevents the need for a calibration to be determined on each system that is manufactured. This represents a significant time and cost savings that can affect the difference between success or failure of a commercial product. Calibration transfer arises from the fact that optical and electronic components vary from unit to unit which, in aggregate, can result in a significant difference in spectra obtained from multiple instruments. For example, two light sources can have different color temperatures thereby resulting in a different light distribution for the two sources. The responsivity of two detectors can also differ significantly, which can result in additional spectral differences.

Similar to calibration maintenance, multiple methods can be used in order to effectively achieve calibration transfer. The first method is to build the calibration with multiple instruments. The presence of multiple instruments allows the spectral variation associated with instrument differences to be determined and made orthogonal to the attribute signal during the calibration formation process. While this approach reduces the net attribute signal, it can be an effective means of calibration transfer.

Additional calibration transfer methods involve explicitly determining the difference in the spectral signature of a system relative to those used to build the calibration. In this case, the spectral difference can then be used to correct a spectral measurement prior to attribute prediction on a system or it can be used to correct the predicted attribute value directly. The spectral signature specific to an instrument can be determined from the relative difference in spectra of a stable sample acquired from the system of interest and those used to build the calibration. The samples described in the calibration maintenance section are also applicable to calibration transfer. See, e.g., U.S. Pat. No. 6,441,388, "Method and Apparatus for Spectroscopic Calibration Transfer", which is incorporated herein by reference.

Consistency of the wavelength axis between instruments is also an important aspect of calibration transfer. The previously discussed etalon and grating based methods for tuning the emission wavelengths of light sources are equally suitable to ensuring wavelength stability over time. This is accomplished by tuning the one or more light sources in all instruments to a predefined set of emission wavelengths. For example, in an embodiment was comprised of 10 light sources, all devices of that embodiment would have the light sources tuned to the same predefined set of 10 emission wavelengths.

Additional Aspects of the Present Invention

Alcohol Measurement Modalities

Depending on the application of interest, the measurement of an analyte property can be considered in terms of two modalities. The first modality is "walk up" or "universal" and represents an analyte property determination wherein prior measurements of the sample (e.g., subject) are not used in determining the analyte property from the current measurement of interest. In the case of measuring in vivo alcohol, driving under the influence enforcement would fall into this modality as in most cases the person being tested will not have been previously measured on the alcohol measurement device. Thus, no prior knowledge of that person is available for use in the current determination of the analyte property.

The second modality is termed "enrolled" or "tailored" and represents situations where prior measurements from the sample or subject are available for use in determining the analyte property of the current measurement. An example of an environment where this modality can be applied is vehicle interlocks where a limited number of people are permitted to drive or operate a vehicle or machine. Additional information regarding embodiments of enrolled and tailored applications can be found in U.S. Pat. Nos. 6,157,041 and 6,528,809, titled "Method and Apparatus for Tailoring Spectroscopic Calibration Models", each of which is incorporated herein by reference. In enrolled applications, the combination of the analyte property measurement with a biometric measurement can be particularly advantageous as the same spectroscopic measurement can assess if a prospective operator is authorized to use the equipment or vehicle via the biometric while the analyte property can access their fitness level (e.g., sobriety).

Methods for Determining Biometric Verification or Identification from Spectroscopic Signals Biometric identification describes the process of using one or more physical or behavioral features to identify a person or other biological entity. There are two common biometric modes: identification and verification. Biometric identification attempts to answer the question of, "do I know you?". The biometric measurement device collects a set of biometric data from a target individual. From this information alone it assesses whether the person was previously enrolled in the biometric system. Systems that perform the biometric identification task, such as the FBI's Automatic Fingerprint Identification System (AFIS), are generally very expensive (several million dollars or more) and require many minutes to detect a match between an unknown sample and a large database containing hundreds of thousands or millions of entries. In biometric verification the relevant question is, "are you who you say you are?". This mode is used in cases where an individual makes a claim of identity using a code, magnetic card, or other means, and the device uses the biometric data to confirm the identity of the person by comparing the target biometric data with the enrolled data that corresponds with the purported identity. The present apparatus and methods for monitoring the presence or concentration of alcohol or substances of abuse in controlled environments can use either biometric mode.

There also exists at least one variant between these two modes that is also suitable for use in the present invention. This variant occurs in the case where a small number of individuals are contained in the enrolled database and the biometric application requires the determination of only whether a target individual is among the enrolled set. In this case, the exact identity of the individual is not required and thus the task is somewhat different (and often easier) than the identification task described above. This variant might be useful in applications where the biometric system is used in methods where the tested individual must be both part of the authorized group and sober but their specific identity is not required. The term "identity characteristic" includes all of the above modes, variants, and combinations or variations thereof.

There are three major data elements associated with a biometric measurement: calibration, enrollment, and target spectral data. The calibration data are used to establish spectral features that are important for biometric determinations. This set of data consists of series of spectroscopic tissue measurements that are collected from an individual or individuals of known identity. Preferably, these data are collected over a period of time and a set of conditions such that multiple spectra are collected on each individual while they span nearly the full range of physiological states that a person is expected to go through. In addition, the instrument or instruments used for spectral collection generally should also span the full range of instrumental and environmental effects that it or sister instruments are likely to see in actual use. These calibration data are then analyzed in such a way as to establish spectral wavelengths or "factors" (i.e. linear combinations of wavelengths or spectral shapes) that are sensitive to between-person spectral differences while minimizing sensitivity to within-person, instrumental (both within- and between-instruments), and environmental effects. These wavelengths or factors are then used subsequently to perform the biometric determination tasks.

The second major set of spectral data used for biometric determinations is the enrollment spectral data. The purpose of the enrollment spectra for a given subject or individual is to generate a "representation" of that subject's unique spectroscopic characteristics. Enrollment spectra are collected from individuals who are authorized or otherwise required to be recognized by the biometric system. Each enrollment spectrum can be collected over a period of seconds or minutes. Two or more enrollment measurements can be collected from the individual to ensure similarity between the measurements and rule out one or more measurements if artifacts are detected. If one or more measurements are discarded, additional enrollment spectra can be collected. The enrollment measurements for a given subject can be averaged together, otherwise combined, or stored separately. In any case, the data are stored in an enrollment database. In some cases, each set of enrollment data are linked with an identifier (e.g., a password or key code) for the persons on whom the spectra were measured. In the case of an identification task, the identifier can be used for record keeping purposes of who accessed the biometric system at which times. For a verification task, the identifier is used to extract the proper set of enrollment data against which verification is performed.

The third and final major set of data used for the biometric system is the spectral data collected when a person attempts to use the biometric system for identification or verification. These data are referred to as target spectra. They are compared to the measurements stored in the enrollment database (or subset of the database in the case of identity verification) using the classification wavelengths or factors obtained from the calibration set. In the case of biometric identification, the system compares the target spectrum to all of the enrollment spectra and reports a match if one or more of the enrolled individual's data is sufficiently similar to the target spectrum. If more than one enrolled individual matches the target, then either all of the matching individuals can be reported, or the best match can be reported as the identified person. In the case of biometric verification, the target spectrum is accompanied by an asserted identity that is collected using a magnetic card, a typed user name or identifier, a transponder, a signal from another biometric system, or other means. The asserted identity is then used to retrieve the corresponding set of spectral data from the enrollment database, against which the biometric similarity determination is made and the identity verified or denied. If the similarity is inadequate, then the biometric determination is cancelled and a new target measurement may be attempted.

In one method of verification, principle component analysis is applied to the calibration data to generate spectral factors. These factors are then applied to the spectral difference taken between a target spectrum and an enrollment spectrum to generate Mahalanobis distance and spectral residual magnitude values as similarity metrics. Identify is verified only if the aforementioned distance and magnitude are less than a predetermined threshold set for each. Similarly, in an example method for biometric identification, the Mahalanobis distance and spectral residual magnitude are calculated for the target spectrum relative each of the database spectra. The identity of the person providing the test spectrum is established as the person or persons associated with the database measurement that gave the smallest Mahalanobis distance and spectral residual magnitude that is less than a predetermined threshold set for each.

In an example method, the identification or verification task is implemented when a person seeks to perform an operation for which there are a limited number of people authorized (e.g., perform a spectroscopic measurement, enter a controlled facility, pass through an immigration checkpoint, etc.). The person's spectral data is used for identification or verification of the person's identity. In this preferred method, the person initially enrolls in the system by collecting one or more representative tissue spectra. If two or more spectra are collected during the enrollment, then these spectra can be checked for consistency and recorded only if they are sufficiently similar, limiting the possibility of a sample artifact corrupting the enrollment data. For a verification implementation, an identifier such as a PIN code, magnetic card number, username, badge, voice pattern, other biometric, or some other identifier can also be collected and associated with the confirmed enrollment spectrum or spectra.

In subsequent use, biometric identification can take place by collecting a spectrum from a person attempting to gain authorization. This spectrum can then be compared to the spectra in the enrolled authorization database and an identification made if the match to an authorized database entry was better than a predetermined threshold. The verification task is similar, but can require that the person present the identifier in addition to a collected spectrum. The identifier can then be used to select a particular enrollment database spectrum and authorization can be granted if the current spectrum is sufficiently similar to the selected enrollment spectrum. If the biometric task is associated with an operation for which only a single person is authorized, then the verification task and identification task are the same and both simplify to an assurance that the sole authorized individual is attempting the operation without the need for a separate identifier.

The biometric measurement, regardless of mode, can be performed in a variety of ways including linear discriminant analysis, quadratic discriminant analysis, K-nearest neighbors, neural networks, and other multivariate analysis techniques or classification techniques. Some of these methods rely upon establishing the underlying spectral shapes (factors, loading vectors, eigenvectors, latent variables, etc.) in the intra-person calibration database, and then using standard outlier methodologies (spectral F ratios, Mahalanobis distances, Euclidean distances, etc.) to determine the consistency of an incoming measurement with the enrollment database. The underlying spectral shapes can be generated by multiple means as disclosed herein.

First, the underlying spectral shapes can be generated based upon simple spectral decompositions (eigen analysis, Fourier analysis, etc.) of the calibration data. The second method of generating underlying spectral shapes relates to the development of a generic model as described in U.S. Pat. No. 6,157,041, titled "Methods and Apparatus for Tailoring Spectroscopic Calibration Models," which is incorporated by reference. In this application, the underlying spectral shapes are generated through a calibration procedure performed on intra-person spectral features. The underlying spectral shapes can be generated by the development of a calibration based upon simulated constituent variation. The simulated constituent variation can model the variation introduced by real physiological or environmental or instrumental variation or can be simply be an artificial spectroscopic variation. It is recognized that other means of determining underlying shapes would be applicable to the identification and verification methods of the present invention. These methods can be used either in conjunction with, or in lieu of the aforementioned techniques.

Calibration Check Samples

In addition to disposables to ensure subject safety, disposable calibration check samples can be used to verify that the instrument is in proper working condition. In many commercial applications of alcohol measurements, the status of the instrument must be verified to ensure that subsequent measurements will provide accurate alcohol concentrations or analyte estimates. The instrument status is often checked immediately prior to a subject measurement. In some embodiments, the calibration check sample can include alcohol. In other embodiments, the check sample can be an environmentally stable and spectrally inert sample, such as an integrating sphere. The check sample can be a gas or liquid that is injected or flowed through a spectroscopic sampling chamber. The check sample can also be a solid, such as a gel, that may contain alcohol. The check sample can be constructed to interface with the sampling subsystem or it can be incorporated into another area of the optical path of the system. These examples are meant to be illustrative and are not limiting to the various possible calibration check samples.

Direction of Change (DOC) and Rate of Change (ROC)

The present invention also comprises methods for measurement of the direction and magnitude of concentration changes of tissue constituents, such as alcohol, using spectroscopy. The noninvasive measurement obtained from the current invention is inherently semi-time resolved. This allows analytes, such as alcohol concentration, to be determined as a function of time. The time resolved alcohol concentrations can then be used to determine the rate and direction of change of the alcohol concentration. In addition, the direction of change information can be used to partially compensate for any difference in blood and noninvasive alcohol concentration that is caused by physiological kinetics. See U.S. Pat. No. 7,016,713, "Determination of Direction and Rate of Change of an Analyte", and U.S. Appl. Publ. No. 2006/0167349, "Apparatus for Noninvasive Determination of Rate of Change of an Analyte", each of which is incorporated herein by reference. A variety of techniques for enhancing the rate and direction signal have been uncovered. Some of these techniques include heating elements, rubrifractants, and index-matching media. They should not be interpreted as limiting the present invention to these particular forms of enhancement or equilibration. These enhancements are not required to practice the present invention, but are included for illustrative purposes only.

Subject Safety

Another aspect of noninvasive alcohol measurements is the safety of the subjects during the measurements. In order to prevent measurement contamination or transfer of pathogens between subjects it is desirable, but not necessary, to use disposable cleaning agents and/or protective surfaces in order to protect each subject and prevent fluid or pathogen transfer between subjects. For example, in some embodiments an isopropyl wipe can be used to clean each subject's sampling site and/or the sampling subsystem surface prior to measurement. In other embodiments, a disposable thin film of material such as ACLAR can be placed between the sampling subsystem and the subject prior to each measurement in order to prevent physical contact between the subject and the instrument. In other embodiments, both cleaning and a film can be used simultaneously. As mentioned in the sampling subsystem portion of this disclosure, the film can also be attached to a positioning device and then applied to the subject's sampling site. In this embodiment, the positioning device can interface with the sampling subsystem and prevent the subject from moving during the measurement while the film serves its protective role.

Topical Interferents

Figure 31:
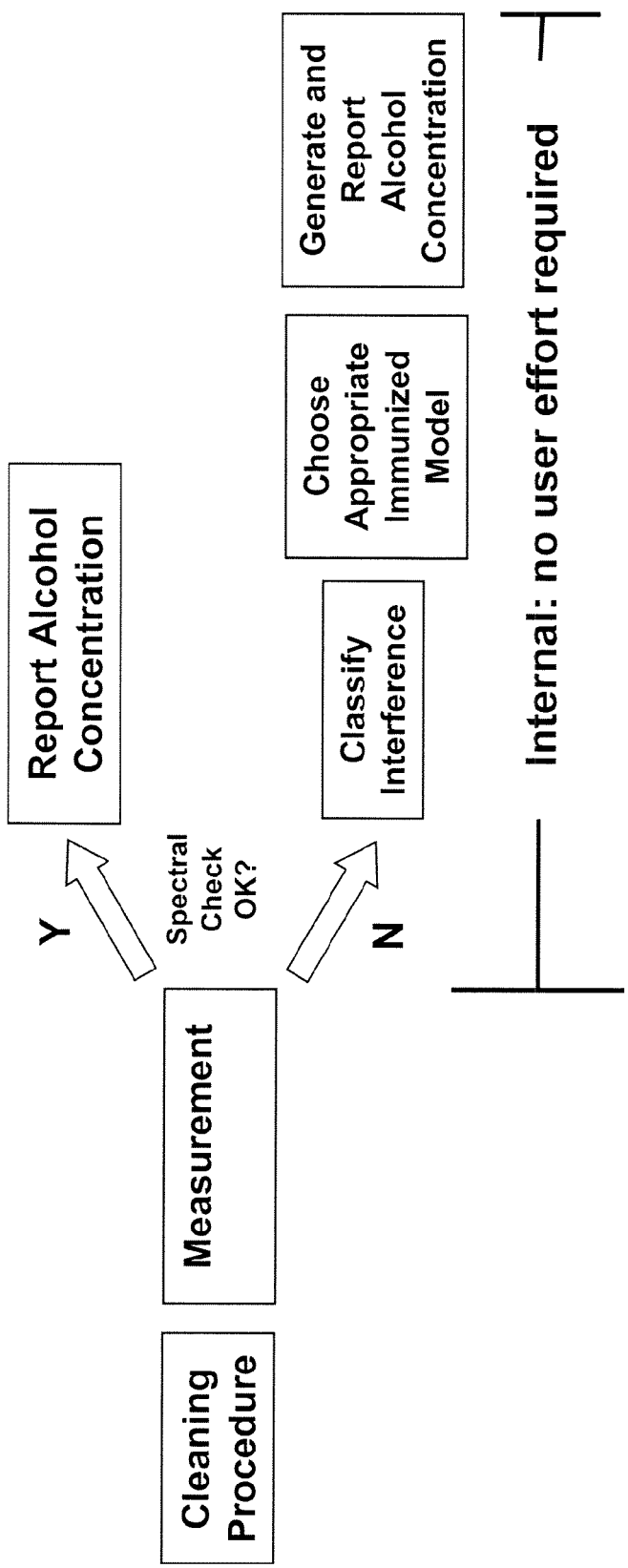
FIG. 31 is a schematic representation of a decision process that combines three topical interferent mitigation strategies.

In subject measurements the presence of topical interferents on the sampling site is a significant concern. Many topical interferents have spectral signatures in the near infrared region and can therefore contribute significant measurement error when present. The present invention deals with the potential for topical interferents in three ways that can be used individually or in conjunction. FIG. 31 shows a flow diagram that describes a method for combining the three topical interferent mitigation approaches into one combined process. First, a disposable cleaning agent similar to that described in the subject safety section can be used. The use of the cleaning agent can either be at the discretion of the system operator or a mandatory step in the measurement process. Multiple cleaning agents can also be used that individually target different types of topical interferents. For example, one cleaning agent can be used to remove grease and oils, while another can be used to remove consumer goods such as cologne or perfume. The purpose of the cleaning agents is to remove topical interferents prior to the attribute measurement in order to prevent them from influencing the accuracy of the system.

Figure 32:
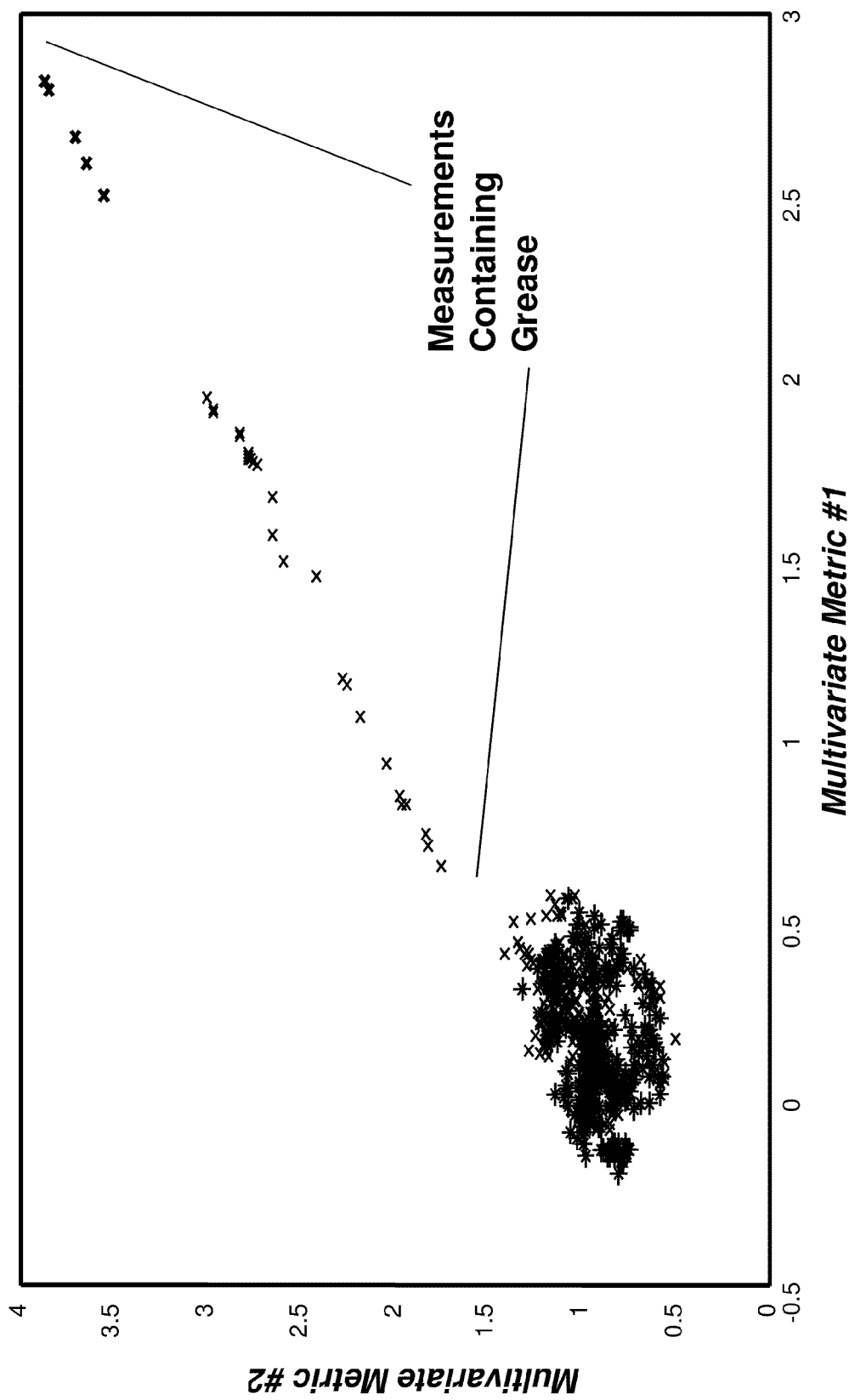
FIG. 32 demonstrates the effectiveness of multivariate calibration outlier metrics for detecting the presence of topical interferents.

The second method for mitigating the presence of topical interferents is to determine if one or more interferents is present on the sampling site. The multivariate calibration models used in the calibration subsystem offer inherent outlier metrics that yield important information regarding the presence of un-modeled interferents (topical or otherwise). As a result, they provide insight into the trustworthiness of the attribute measurement. FIG. 32 shows example outlier metric values from noninvasive measurements using the present invention acquired during the clinical studies. All of the large metric values (clearly separated from the majority of the points) correspond to measurements where grease had been intentionally applied to the subject's sampling site. These metrics do not specifically identify the cause of the outlier, but they do indicate that the associated attribute measurement is suspect. An inflated outlier metric value (a value beyond a fixed threshold, for example) can be used to trigger a fixed response such as a repeat of the measurement, application of an alternative calibration model, or a sampling site cleaning procedure. This is represented in FIG. 31 as the "Spectral Check OK?" decision point.

The final topical interferent mitigation method involves adapting the calibration model to include the spectral signature of the topical interferent. The adapted calibration model can either be created on demand or selected from an existing library of calibration models. Each calibration in the library would be targeted at mitigating a different interferent or class of interferents such as oils. In some embodiments, the appropriate calibration model can be chosen based on the portion of an acquired spectrum that is unexplained by the original calibration model. This portion of the spectrum is referred to as the calibration model residual. Because each topical interferent or class of interferents has a unique near infrared spectrum, the calibration model residual can be used to identify the topical interferent.

The model residual or the pure spectrum (obtained from a stored library) of the interferents can then be incorporated into the spectra used to form the calibration. The multivariate calibration is then reformed with the new spectra such that the portion of the attribute signal that is orthogonal to the interferent can be determined. The new calibration model is then used to measure the attribute of interest and thereby reduce the effects of the topical interferent on attribute measurement accuracy. The resulting model will reduce the effect of the interferent on the alcohol measurement at the expense of measurement precision when no interferents are present. This process is referred to as calibration immunization. The immunization process is similar to the hybrid calibration formation process shown in FIG. 31, but includes the additional step of the mathematical addition of the interferent's spectral variation. It should be noted that, due to the impact of the immunization process on measurement precision, it can be desirable to identify possible interferents for each measurement and immunize specifically against them rather than attempt to develop a calibration that is immunized against all possible interferents. Additional details can be found in U.S. Appl. Publ. No. 2007/0142720, "Apparatus and methods for mitigating the effects of foreign interferents on analyte measurements in spectroscopy", which is incorporated herein by reference.

Description of Example Embodiments

Figure 33:
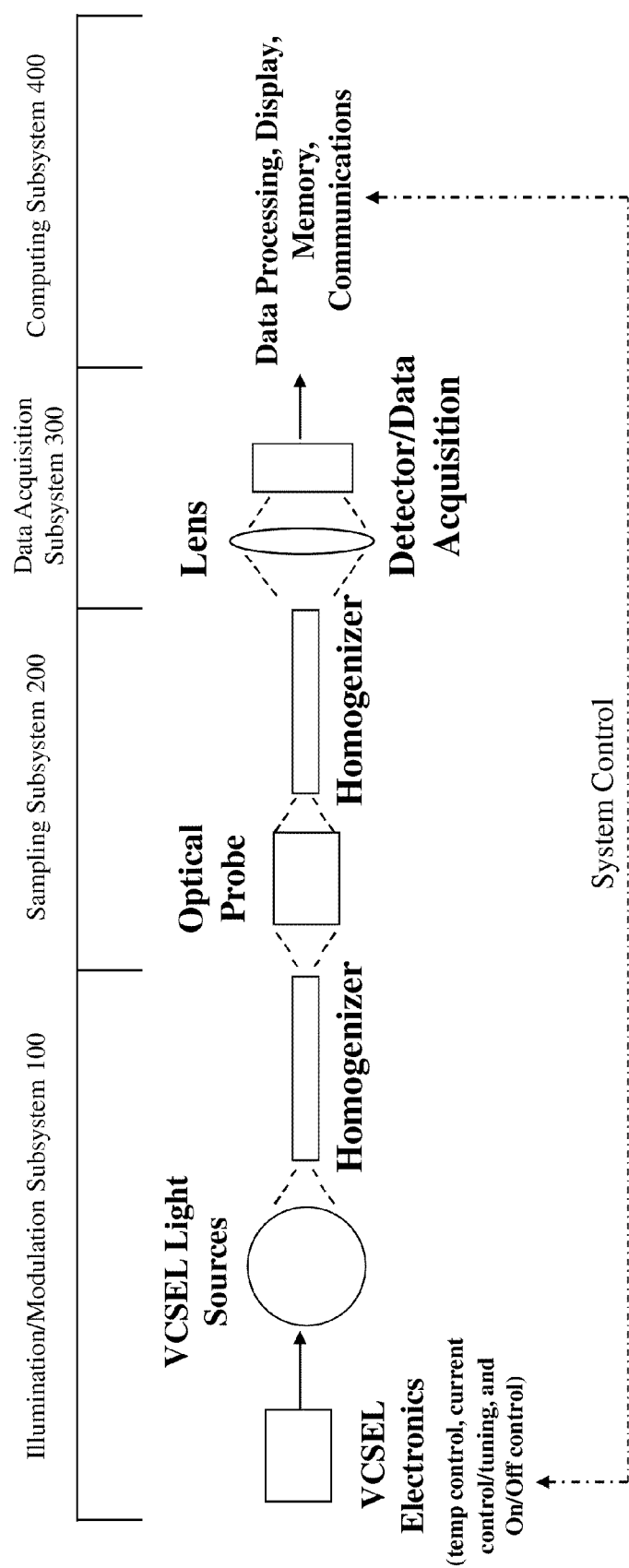
FIG. 33 shows a schematic of the components of a preferred embodiment of the present invention

In an example embodiment of the present invention (schematically depicted in FIG. 33), a noninvasive alcohol measurement system is comprised of 13 VCSEL's that are used to measure 22 discrete wavelengths. Table 1 shows a list of each VCSEL and the associated target peak wavelengths that can be interrogated during the course of the measurement. In this embodiment, each VCSEL is stabilized to a constant temperature. The peak wavelength of each VCSEL is controlled based on the circuit shown in FIG. 34 (each VCSEL having its own circuit), which also enables the VCSEL to be turned On and Off. The specific state (On/Off) of each VCSEL at a given time during a measurement is determined by a predetermined Hadamard matrix. In example embodiments incorporating solid state light sources the Hadamard matrix is a pattern of On/Off states versus time for each VCSEL that is stored in software rather than a physical mask or chopper. This allows the On/Off states stored in software to be conveyed to the electronic control circuits of each VCSEL during the measurement.

As several of the VCSEL's in Table 1 are responsible for 2 wavelength locations, a Hadamard scheme that incorporates all wavelengths can be difficult to achieve. In this case, a combination of scanning and Hadamard encoding can allow all target wavelengths to be measured. In the present embodiment, all VCSEL's are tuned to their $1^{st}$ target wavelength (for those with more than 1 target wavelength) and a Hadamard encoding scheme used to achieve the associated multiplex benefit. The VCSEL's can then be tuned to their second target wavelength and a $2^{nd}$ Hadamard encoding scheme used. VCSEL's with only 1 target wavelength can be measured in either or both groups or divided among the groups.

Furthermore, the groups can be interleaved in time. For example, for a 2 second measurement, the first group can be measured for the $1^{st}$ second and the $2^{nd}$ group for the $2^{nd}$ second. Alternatively, the measurement can alternate at 0.5 second intervals for 2 seconds. The measurement times do not need to be symmetric across the groups. For example, it can be desirable to optimize signal to noise ratio by weighting the measurement time towards one or the other group. One skilled in the art recognizes that many permutations of measurement time, balancing the number of groups, balancing the ratio of scanning to Hadamard, and interleaving are possible and contemplated in the embodiments of the present invention.

In the example embodiment, the output of each VCSEL is combined and homogenized using a hexagonal cross-sectioned light pipe. In some embodiments, the light pipe can contain one or more bends in order to provide angular homogenization in addition to spatial homogenization. Regardless, at the output of the light pipe, the emission of all VCSEL's is preferably spatially and angularly homogenized such that all wavelengths have substantially equivalent spatial and angular content upon introduction to the input of the sampling subsystem 200.

Figure 34:
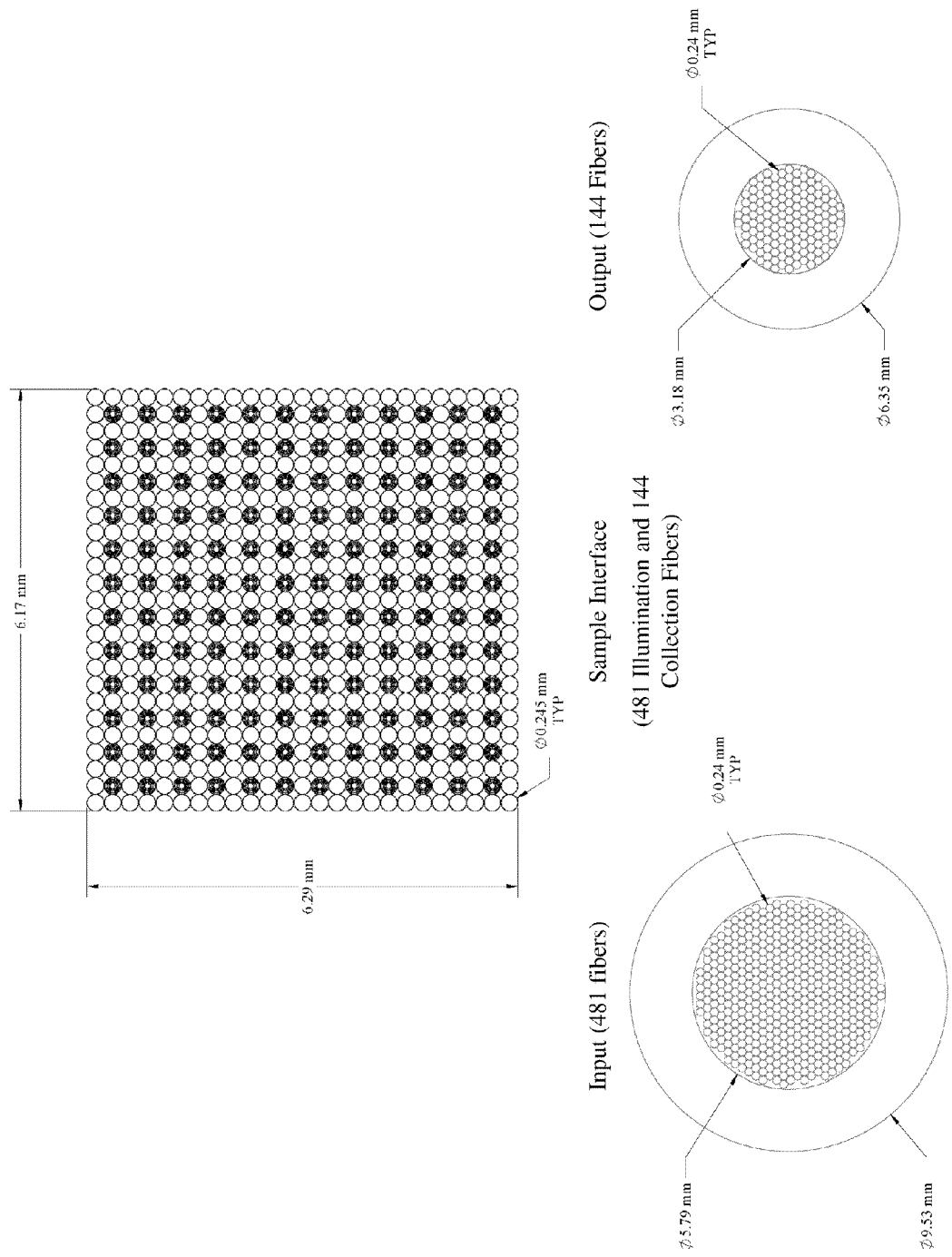
FIG. 34 is a schematic of the arrangement of illumination and collection fibers at the sample interface for a preferred embodiment of an optical probe of the present invention.

The homogenized light is introduced to the input of an optical probe. In the example embodiment, the input is comprised of 225, 0.37 NA silica-silica optical fibers (referred to as illumination fibers) arranged in a geometry consistent with the cross section of the light homogenizer. The light is then transferred to the sample interface. The light exits the optical probe and enters the sample, a portion of that light interacts with the sample and is collected by 64 collection fibers. In the present preferred embodiment, the collection fibers are 0.37 NA silica-silica fibers. FIG. 34 shows the spatial relationship between the illumination and collection fibers at the sample interface.

The optical probe output arranges the collection fibers into a geometry consistent with the introduction to a homogenizer. For the example embodiment, the homogenizer is a hexagonal light pipe. The homogenizer ensures that the content of each collection fiber contributes substantially equally to the measured optical signal. This can be important for samples, such as human tissue, that can be heterogeneous in nature. The output of the homogenizer is then focused onto an optical detector. In the present preferred embodiment, the optical detector is an extended InGaAs diode whose output current varies based upon the amount of incident light.

The processing subsystem then filters and processes the current and then converts it to a digital signal using a 2 channel delta-sigma ADC. In the example embodiment, the processed analog detector signal is divided and introduced to both ADC channels. As the example embodiment involves VCSEL's with 2 measurement groups (e.g., 2 target wavelengths), a Hadamard transform is applied to the spectroscopic signal obtained from each group and the subsequent transforms combined to form an intensity spectrum. The intensity spectrum is then base 10 log transformed prior to subsequent alcohol concentration determination.

The example embodiment is suitable for either "enrolled" or "walk-up/universal" modalities as well as applications combining alcohol with other analyte properties such as substances of abuse. Furthermore, any of the discussed modalities or combinations can be considered independently or combined with the measurement of a biometric property.

Figure 35:
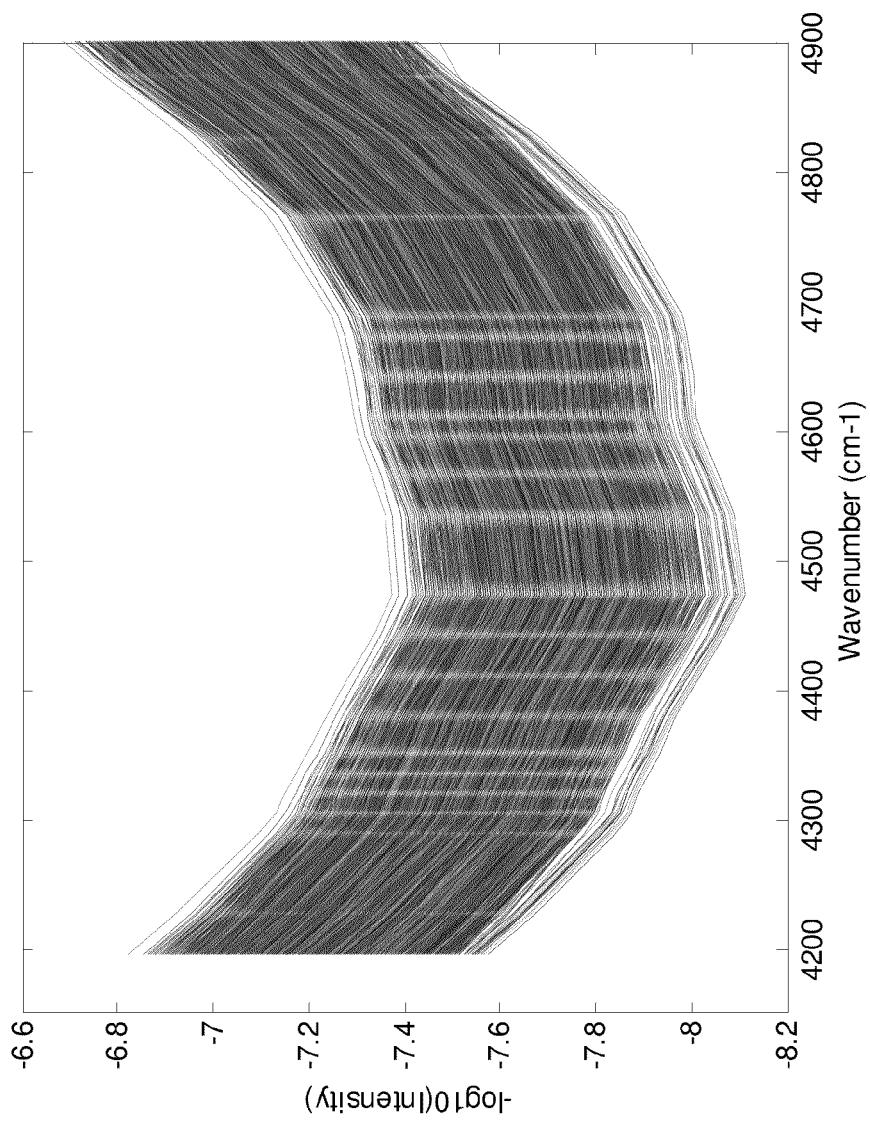
FIG. 35 depicts noninvasive tissue spectra acquired using 22 wavelengths.
Figure 36:
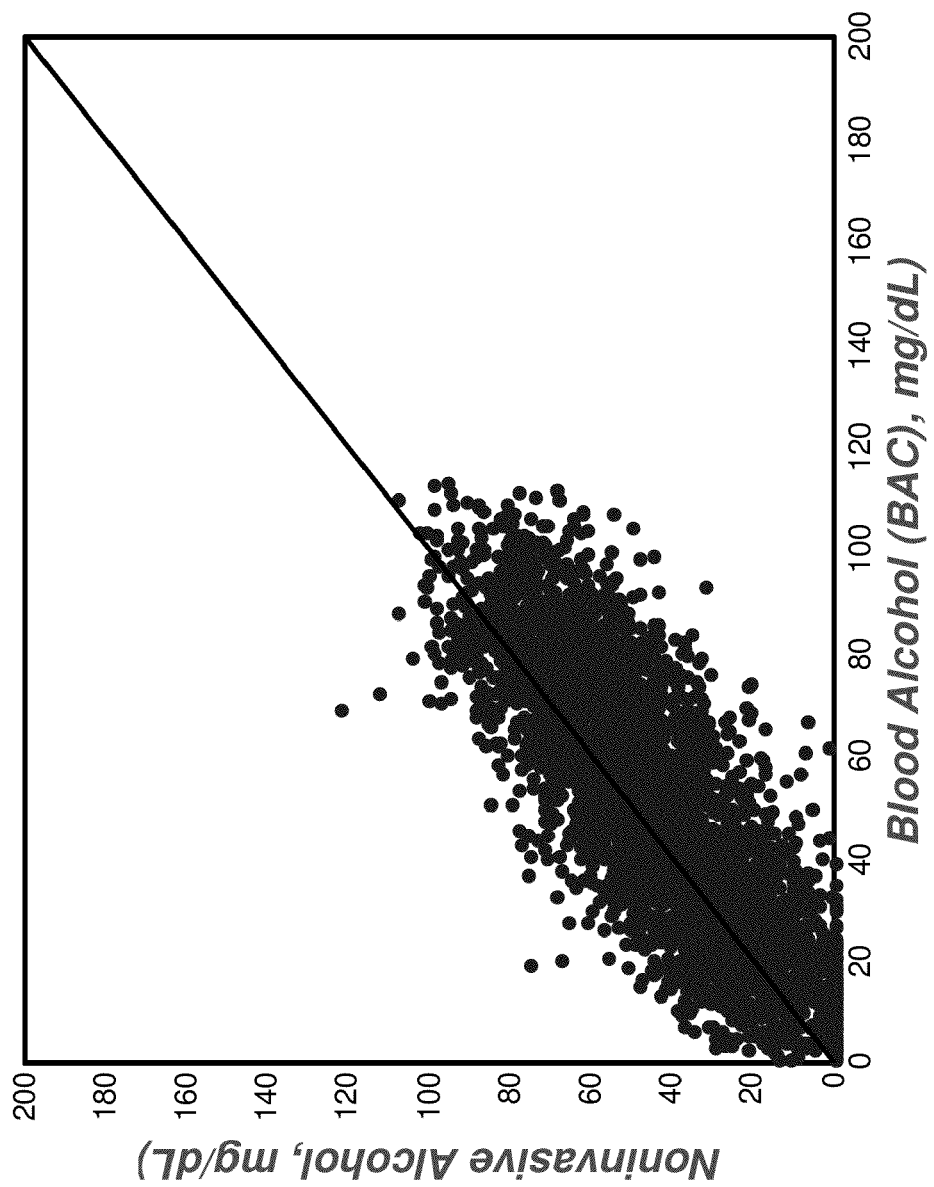
FIG. 36 compares noninvasive tissue alcohol concentrations obtained from the spectra in FIG. 28 to contemporaneous capillary blood alcohol concentration.

3,245 alcohol measurements were obtained from 89 people on 5 noninvasive alcohol systems that measured spectra incorporating 22 wavelengths in the "walk-up" modality. The measurements spanned a wide range of demographic and environmental. FIG. 35 shows the near-infrared spectroscopic measurements obtained from the study. FIG. 36 compares noninvasive alcohol concentrations obtained from the spectroscopic measurements shown in FIG. 35 to contemporaneous capillary blood alcohol concentration (BAC) alcohol.

In another example embodiment, 50 wavelengths are measured using 24 VCSEL's. Table 2 shows the VCSEL's and their target wavelengths. As some of the VCSEL's contain 3 target wavelengths, there are 3 groups, each with its own Hadamard encoding scheme. The remainder of the system parameters, including the optical probe design, light homogenizers, detector, and processing is identical to the earlier described preferred embodiment.

In some example embodiments, calibration transfer can be performed using a small number of measurements on samples with known analyte properties. In the case of noninvasive alcohol measurements, each instrument can have a small number of measurements performed on individuals with no alcohol present. Any non-zero alcohol result on the instrument translates into a measurement error that can be used to correct subsequent measurements on that instrument. The number of measurements used to estimate the correction can vary and generally depends on the required accuracy of the correction. In general, this process is analogous to an instrument specific calibration consistent with alcohol devices, such as breath testers, that are calibrated individually.

A similar approach can be applied to calibration maintenance. In many applications of alcohol testing, the majority of measurements are performed on individuals where alcohol is unlikely to be present. For example in workplace safety where employees are routinely tested for alcohol, it is much more likely that an employee will be alcohol free than intoxicated (e.g., most people enter the workplace alcohol-free). In this case, the true alcohol concentration can be assumed to be zero and a median or other means for excluding the infrequent, true alcohol events can be used to estimate an instruments correction. This can implemented as a running median filter, a moving window, or more sophisticated multivariate algorithm for determining the appropriate correction at a given time.

Methods for Performing Actions in Controlled Environments

The signal required to perform the action can be wireless or wired as deemed appropriate for the application. Furthermore, in some embodiments, wireless communication can also be used to report the measurement results or the operational status of the monitoring device to a central monitoring, security, maintenance, or law enforcement facility. One skilled in the art will appreciate the wide variety of environments and systems that could feasibly incorporate or function as the analyte monitoring device of the present invention.

Figure 37:
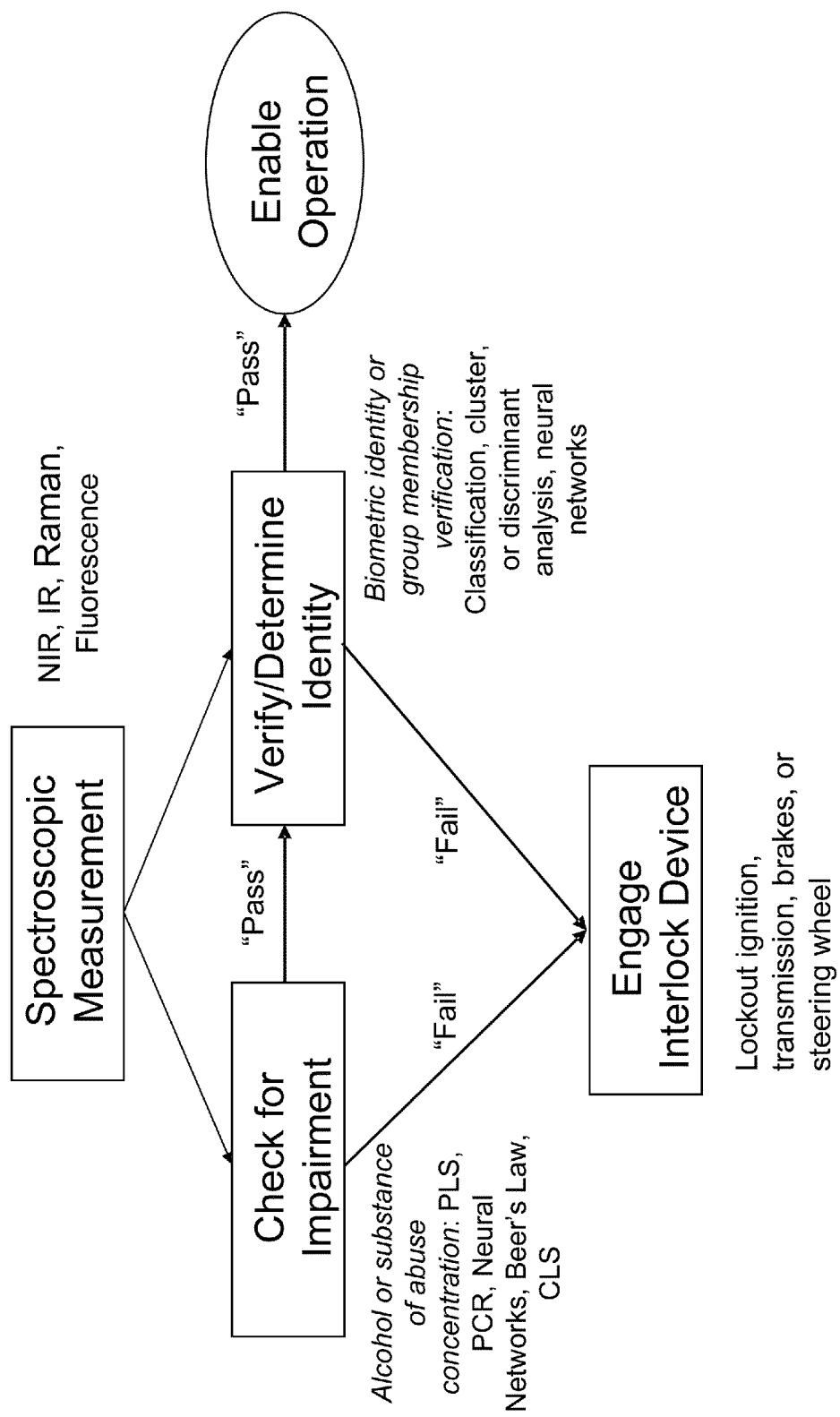
FIGS. 37 and 38 are diagrams of example embodiments of the present invention.
Figure 38:
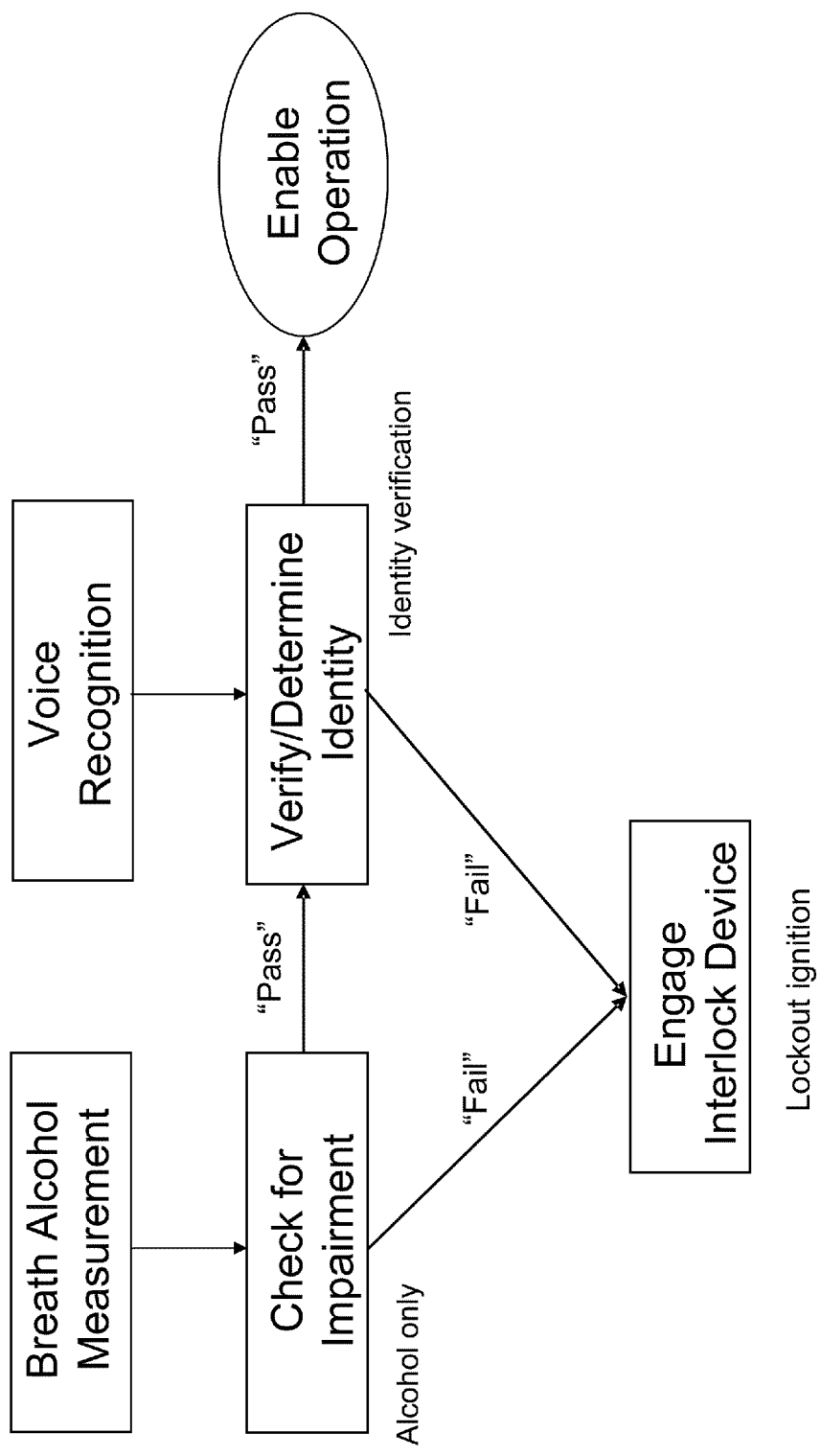

FIG. 37 shows an embodiment of the present invention where a single spectroscopic measurement is used to determine the presence or concentration of an analyte and verify identity of the tested individual. A significant advantage of the present invention is the potential to detect impairment caused by alcohol and/or substances of abuse rather than alcohol alone which significantly increases the utility of the present invention. FIG. 38 shows another example embodiment, with spectroscopic analyte measurement used in combination with voice recognition (or other) identity determination or verification.

Remote Storage of Enrollment Data/Smartkeys

Additional security, convenience, and policy control may be achieved by storing an individual's biometric data on an external communication device rather than internally in a given measurement device. A "smartkey" which can comprise an electronic storage and communication device can store, encrypt, and securely communicate data to the measurement device. For example, in some embodiments the smartkey can enable physical access control to a facility by utilizing a digital two key authentication scheme. The first key can be an authorized electronic access code which is specific to a facility that the user is authorized to enter. The second key can be linked to the individual's enrollment data which requires that only the authorized individual use that key.

This type of system has several advantages. First, the system can use existing technology which has been developed for secure encryption, data transmission, and authentication transactions using smart cards/tokens. Second, in applications where an individual might be required to frequently move between multiple secure locations the use of a smartkey to store biometric data allows centralized administration of both location specific and user specific security and alcohol/substance of abuse policies. An individual can be enrolled in an administrator's office or specified location on a master device and the resulting enrollment information and individual specific security policy can be encoded on that individual's key. The individual can then perform alcohol and biometric measurements on multiple devices, even if the individual has never before used that specific device. An additional advantage of some embodiments is that centralized administration tasks, e.g., restricting or revoking an individual's privileges, can be handled using a single database. Security policy updates can be relayed to the appropriate devices in other locations via RF uplinks or other electronic transmission means. In some embodiments, the use of RF communication and an individual's smartkey can provide rapid, seamless access to a facility via the touch based biometric verification step. No access codes are required from the individual. Third, in applications where updated enrollment is desired, such as restricted access to multiple buildings in a large facility, an individual's enrollment data may become out of date at a given location that he or she seldom uses. By storing the enrollment data on a user specific smartkey, the individual can always maintain the most current enrollment information regardless of the testing location. In some embodiments, profile updates can be handled via two-way communication with the smartkey upon successful biometric identity verification. Finally, concerns regarding the theft, manipulation, or dissemination of an individual's biometric identity information is greatly reduced as only a single copy of that data exists, in a secure, encrypted format, under physical control of the individual at all times.

Some embodiments for remotely storing enrollment data are comprised of a means for storing data, a means for providing power, a means for communication and data transfer. The means for storing data can be any electronic or magnetic storage media consistent with the form factor desired. Some example embodiments of the means for providing power include, but are not limited to, a battery or external RF power via the communication uplink. Some example embodiments of the means for communication and data transfer include, but are not limited to, serial or other secure data protocol via RF, optical, sonic, or direct electrical connections. These components can be combined in many possible form factors. Some examples include car key, plastic transponder, credit card style smart card, employee id badge, lapel pin, etc.

One application that can benefit from the transfer of enrollment data is networks of remote, unattended monitoring systems. In one embodiment, the network can be comprised of one or more kiosks located in multiple locations. In this type of scenario, an individual that is required to check-in and provide proof of conformance to alcohol or substance of abuse restrictions could find the nearest kiosk that is part of the network. In this case, the individual's enrollment data can be provided by the SmartKey embodiment above or transferred to the kiosk via another kiosk or central station using any of a variety of means such as wireless, telephone line, cable line, fiber optics, or any other means of data transfer. In this scenario, the remote kiosk would verify that the purported individual is being tested and subsequently screen or test for alcohol and/or substances of abuse. Such approaches can provide improved flexibility and increased testing frequency relative to tests performed at a single facility.

Experimental Results: Alcohol

Two clinical studies were performed in order to demonstrate the alcohol measurement capability of the present invention. The first was a calibration study based upon the hybrid calibration model approach described above. The in vitro portion of the data was a 1.0 mm pathlength spectrum of 501.65 mg/dL alcohol in water measured in transmission. The spectrum was ratioed to a 1.0 mm pathlength transmission spectrum of carbon tetrachloride and converted to absorbance. The contribution of water to the 501.65 mg/dL alcohol spectrum was removed by subtracting an absorbance spectrum of pure water scaled to the appropriate concentration to account for the displacement effects of alcohol. Given the level of dilution of the alcohol solution, this is a reasonable first approximation since water is the dominant component of the matrix and is likely not significantly affected (in a chemical sense) by the presence of the minute quantity of alcohol. The resulting water-corrected 501.65 mg/dL alcohol spectrum was normalized to unit pathlength and concentration (absorptivity per mg/dL) and pathlength scaled for tissue as shown in FIG. 29.

The in vivo calibration data consisted of noninvasive tissue spectra collected from individuals who had not consumed alcohol. The hybrid model spectra were formed by adding the alcohol pure component spectrum at various simulated alcohol "concentrations" according to the schematic process shown in FIG. 30. The concentration for each simulated spectrum was simply drawn randomly from a uniform distribution spanning the expected range of alcohol concentrations in vivo (0 to 160 mg/dL). Each spectrum was treated as completely independent of all others, so no inter- or intra-subject differences or time dependencies were incorporated in the concentration assignments. A partial least squares (PLS) calibration model was built by regressing the synthetic alcohol concentrations on the hybrid calibration spectral data. The hybrid calibration contained approximately 1500 noninvasive NIR measurements collected from 133 subjects over three months.

The second study was a prospective validation experiment where ten volunteer subjects were measured in a clinical laboratory over a period of 5 days to assess the noninvasive alcohol measurement accuracy relative to blood and breath alcohol measurements. None of these ten subjects participated in the calibration experiment, so they represented an objective and prospective assessment of the noninvasive NIR measurement performance. Subjects were consented according to an IRB-approved protocol. Alcohol doses were administered to achieve peak blood alcohol concentration (BAC) values of 120 mg/dL (0.12%) assuming ingested alcohol would be completely absorbed into the bloodstream. The subjects were asked to consume the total alcohol dose within a 20-minute time period.

Baseline capillary blood, breath, and noninvasive alcohol measurements were acquired from each subject upon arrival in order to verify zero initial blood alcohol concentration. The blood measurements were acquired using a Yellow Springs Incorporated 2700 Select blood analyzer (YSI). Breath testing was accomplished using an Intoximeters EC/IR in "quick test" mode. Each subject then consumed his or her alcohol dose. Repeated cycles of blood, breath, and noninvasive measurements were then acquired to monitor alcohol concentration throughout each subject's alcohol excursion (about 10-12 minutes per cycle). A total of 372 sets of noninvasive, blood, and breath alcohol measurements were acquired from the 10 subjects in the validation study.

Figure 39:
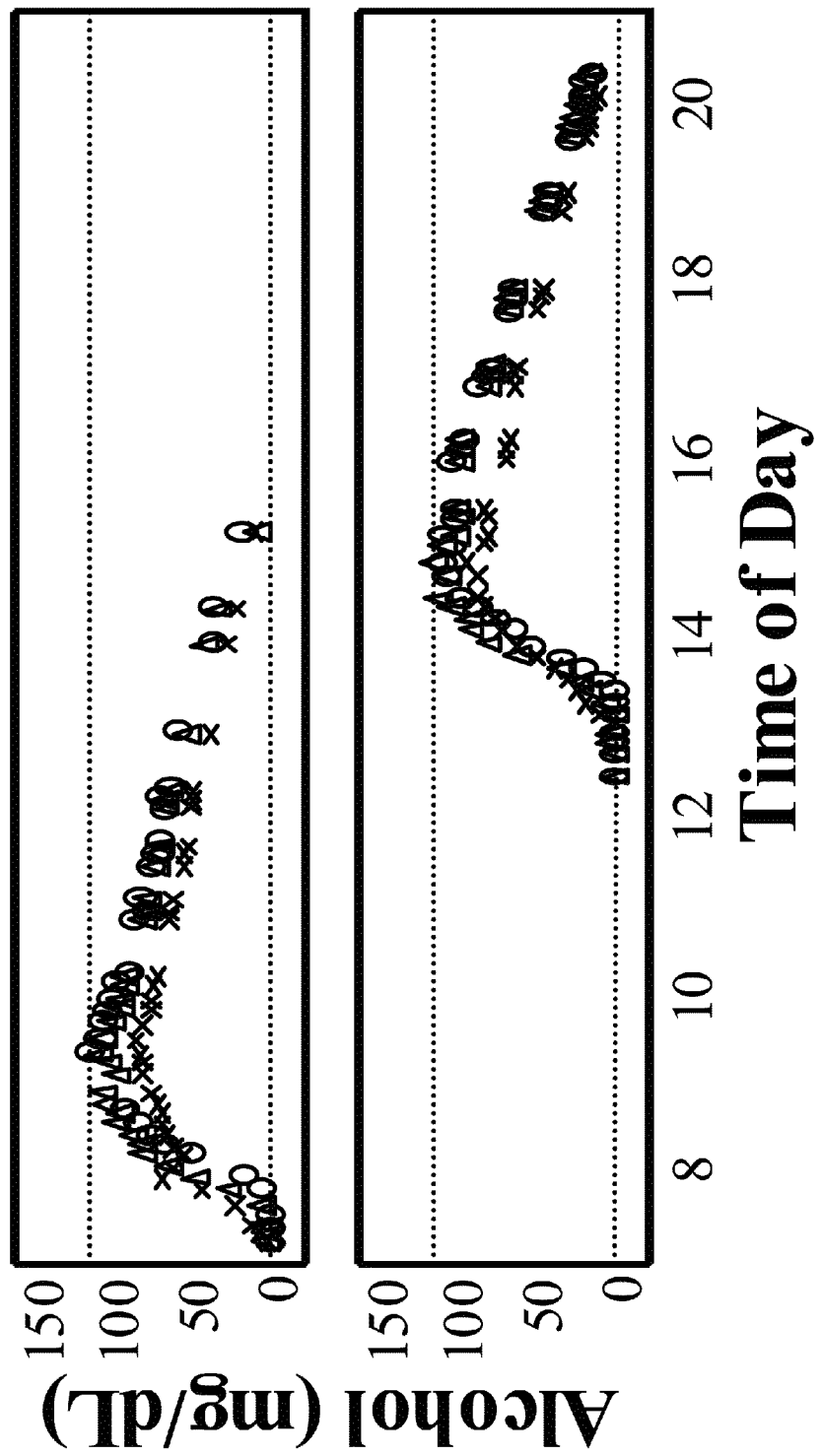
FIG. 39 shows blood, breath, and noninvasive alcohol (obtained from the present invention) over time for two subjects during induced alcohol excursions.
Figure 40:
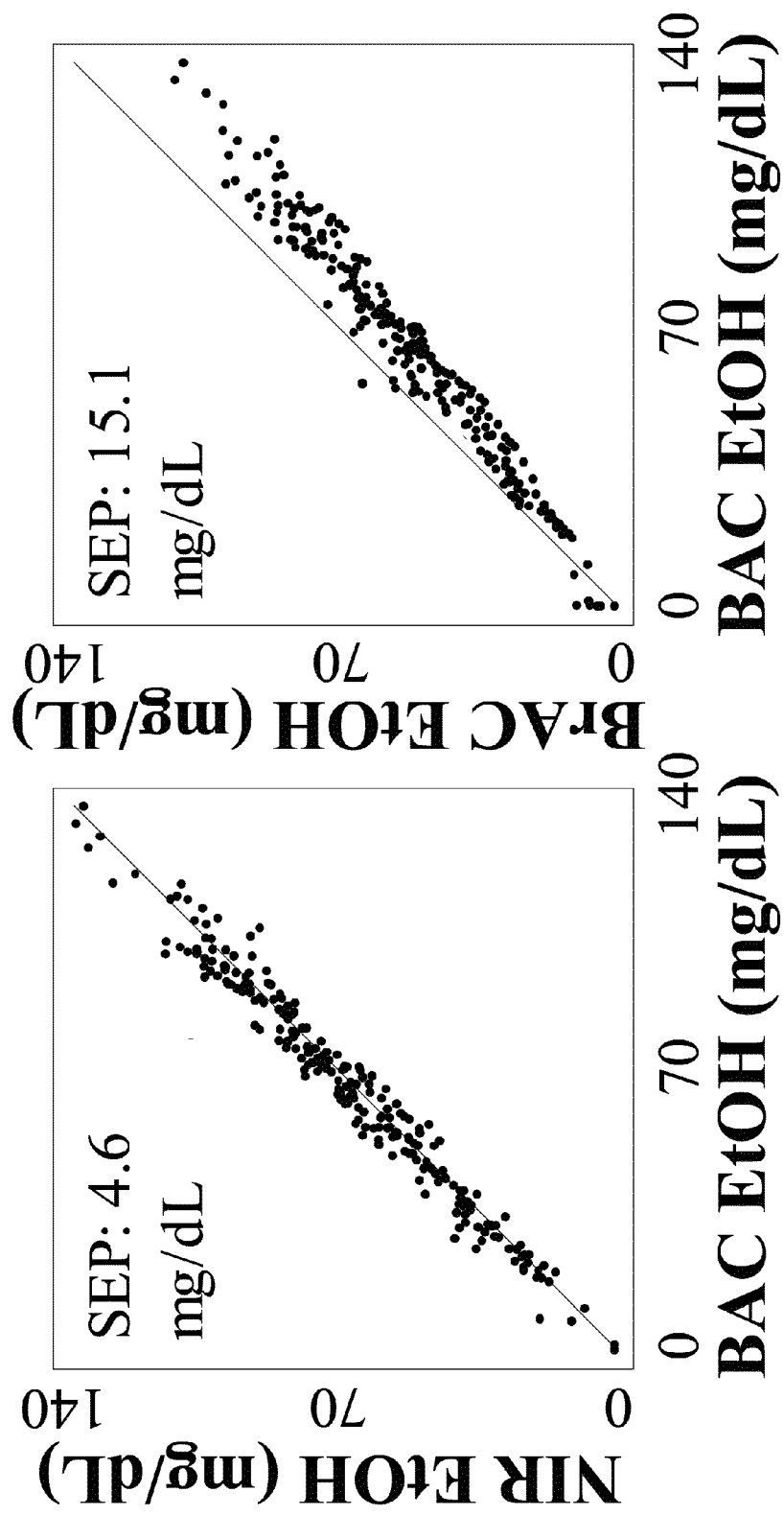
FIG. 40 is a graph of noninvasive alcohol measurements versus blood alcohol reference for multiple human subjects that demonstrates the ability of the system of the present invention to derive clinically relevant alcohol measurements.

FIG. 39 depicts the alcohol measurements acquired from two of the 10 validation subjects during their induced alcohol excursions. Each window contains the blood, breath, and noninvasive alcohol concentrations versus time that were measured during the alcohol excursion for that subject. FIG. 40 shows a side-by-side comparison of the noninvasive spectroscopic alcohol measurements of the present invention versus blood (BAC) alcohol and breath (BrAC) versus blood (BAC) alcohol that were acquired from the 10 study subjects. Examination of FIG. 39 demonstrates that the breath measurements exhibit a proportional error relative to blood alcohol. This is due to the globally applied blood-breath partition coefficient of 2100 mg EtOH/dL blood per mg EtOH/dL air that relates the concentration of alcohol in expired air from the lungs to blood alcohol. The comparison of the breath and noninvasive measurements demonstrates that under identical experimental conditions the precision of the current invention's measurement is substantially equal to that of a commonly used state-of-the-art breath alcohol instrument. In addition, the noninvasive measurement accuracy is superior to the breath measurement because it does not exhibit a proportional error.

Experimental Results: Biometric

An experiment was conducted to determine the viability of utilizing the methodology disclosed herein to verify the identification of an individual using near infrared spectroscopic measurements of skin tissue. The design of the instrumentation used was identical to that described for the experimental alcohol results discussed above. The sampling of the human tissue was done on the volar side of the forearm, consistent with the alcohol experiment. Spectra were acquired, and the recorded 4,200 to 7,200 $cm^{-1}$ NIR spectra converted to absorbance. The spectra consisted of two distinct sets. The first set was a calibration set comprised of 10,951 noninvasive spectroscopic measurements acquired from 209 subjects. On average, approximately 5 measurements were acquired from each subject for each of approximately 10 days. The second set of spectra was a validation set comprised of 3,159 noninvasive spectral measurements from 37 subjects. Each subject was measured approximately 85 times over a 2 month period.

The calibration spectra were processed to produce generic data as described in U.S. Pat. No. 6,157,041, titled "Methods and Apparatus for Tailoring Spectroscopic Calibration Models," incorporated herein by reference. A PCA decomposition of these data was performed to generate 50 factors (also called latent variables, loadings, or eigenvectors) and associated scores (also called weights or eigenvalues). The validation measurements were then split into enrollment and test sets. The enrollment set was comprised of 37 spectra that were obtained by averaging the first three measurements acquired from each of the 37 validation subjects. The test set was comprised of the remaining validation spectra.

In order to evaluate the ability of the present invention to correctly verify the identity of a person, the enrollment spectrum of each subject was subtracted from his or her spectra in the test set. The Mahalanobis distances of the resulting "authorized" spectral differences were then calculated using the calibration factors and scores. In order to evaluate the ability to correctly reject "intruders" (an unauthorized person who claims to be authorized in order enter or leave a controlled environment), the enrollment spectrum for a given subject was subtracted from the test spectra for the other 36 validation subjects. This was done for each validation subject in round-robin fashion in order to test all possible enrollment/test permutations. Similar to the "authorized" case, the Mahalanobis distance for each of the resulting "intruder" difference spectra was computed relative to the calibration factors and scores.

The "authorized" and "intruder" Mahalanobis distances were then used to examine the biometric performance of the spectroscopic method using multiple distance thresholds. In this framework, if the distance of a given spectral difference (whether from the "authorized" or "intruder" group) is less than the threshold distance, then the purported identity is verified. The case where an "authorized" spectral difference is below the threshold (and the identity verified) is referred to as a "True Accept" (also called a True Positive or True Admission). The case where an "authorized" spectral difference is above the threshold (the device erroneously rejects an authorized user) is referred to as a "False Reject" or "False Negative". Similarly, a "True Reject" or "True Negative" occurs when an "intruder" distance is above the threshold and a "False Accept" occurs when an "intruder" distance is below the threshold.

Figure 41:
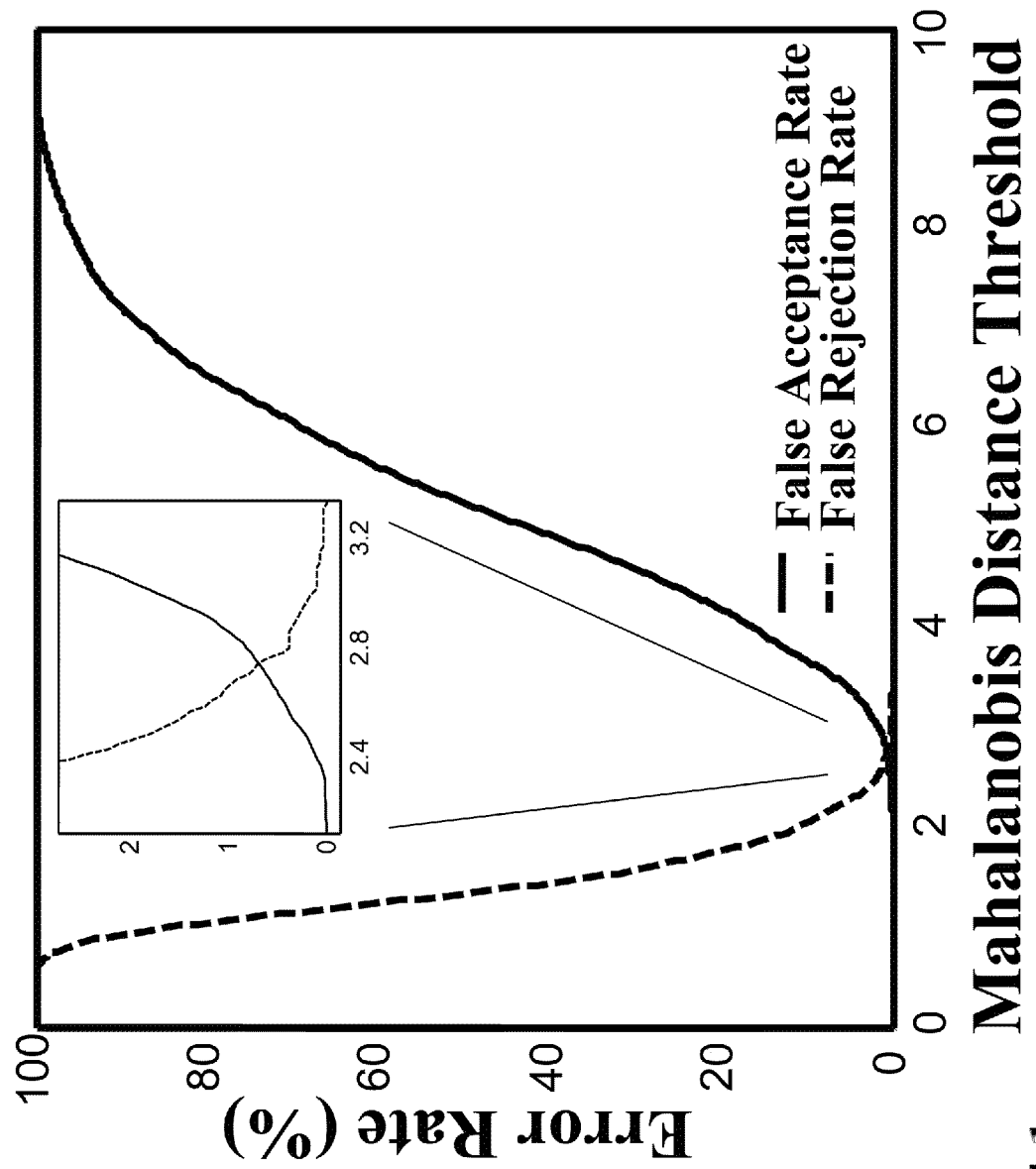
FIG. 41 shows the biometric verification false acceptance, false rejection, and equal error rates obtained using the spectroscopic method of the present invention in clinical studies.

The overall performance of a technique can be compactly summarized at a given threshold by calculating the "false acceptance rate" and the "false rejection rate". The false acceptance rate is the percentage of measurements acquired from intruders that are erroneously flagged as authorized. Conversely, the false rejection rate is the percentage of measurements acquired from authorized persons that are erroneously flagged as intruders. The threshold is a tunable variable that can be used to influence the relative security of the biometric measurement. For example, the threshold can be set to a low value (high security) that can minimize the false acceptance rate at the expense of an increase in the false rejection rate. Likewise, a low security setting would correspond to a high threshold value. In this scenario, authorized users would be rejected less frequently at the expense of an increase in intruder admission. FIG. 41 shows the false acceptance and false rejection rates at a variety of thresholds for the test data discussed above. The "equal error rate" occurs when the false acceptance and rejection rates are equal and is a common metric often used to compare biometric performance across techniques. The equal error rate for these data is approximately 0.7% demonstrating a high degree of biometric capability over an extended period of time.

The particular sizes and equipment discussed herein are cited merely to illustrate particular embodiments of the invention. It is contemplated that the use of the invention can involve components having different sizes and characteristics. It is intended that the scope of the invention be defined by the claims appended hereto. The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

TABLE 1

| Light Source # | Wavelengths Measured (cm$^{-1}$) |
| --- | --- |
| 1 | 4196.35, 4227.2 |
| 2 | 4288.91, 4304.34 |
| 3 | 4319.77, 4335.20 |
| 4 | 4350.62 |
| 5 | 4381.48, 4412.34 |
| 6 | 4443.19, 4474.05 |
| 7 | 4535.76, 4566.61 |
| 8 | 4597.47, 4612.90 |
| 9 | 4643.75 |
| 10 | 4674.61, 4690.04 |
| 11 | 4767.17 |
| 12 | 4828.88 |
| 13 | 4875.17, 4906.02 |

TABLE 2

| Light Source # | Wavelengths Measured (cm$^{-1}$) |
| --- | --- |
| 1 | 4150.06 |
| 2 | 4227.20 |
| 3 | 4304.34, 4319.77, 4335.20 |
| 4 | 4350.62, 4366.05, 4381.48 |
| 5 | 4396.91, 4412.34, 4427.76 |
| 6 | 4443.19, 4458.62 |
| 7 | 4535.76 |
| 8 | 4566.61, 4582.04 |
| 9 | 4674.61, 4690.04, 4705.46 |
| 10 | 4751.75, 4767.17 |
| 11 | 4782.60, 4798.03 |
| 12 | 4890.60, 4906.02 |
| 13 | 5291.72, 5322.57 |
| 14 | 5384.28 |
| 15 | 5461.42, 5476.85 |
| 16 | 5708.27, 5723.69 |
| 17 | 5800.83, 5816.26 |
| 18 | 5847.12, 5862.54, 5877.97 |
| 19 | 5893.40, 5908.83 |
| 20 | 5939.68, 5955.11, 5970.54 |
| 21 | 6016.82, 6032.25 |
| 22 | 6063.10 |
| 23 | 6124.82, 6140.24 |
| 24 | 7189.33, 7204.76 |

What is claimed is:

1. An apparatus for initiating an action responsive to an individual entering or leaving or attempting to enter or leave a controlled environment, comprising:
   a) a spectroscopic system adapted to determine a spectroscopic signal from the response of at least a portion of the individual's tissue to incident electromagnetic radiation, wherein the spectroscopic system comprises:
   i) an illumination/modulation subsystem;
   ii) a tissue sampling subsystem;
   iii) a data acquisition subsystem;
   iv) an analysis subsystem adapted to determine from the spectroscopic signal one or more analyte properties characteristic of the individual; and
   v) a calibration subsystem;
  b) an action initiation system adapted to initiate an action responsive to the one or more analyte properties.

2. An apparatus as in claim 1, wherein the analysis system is further adapted to determine an identity characteristic of the individual from the spectroscopic signal, and wherein the action initiation system is adapted to initiate an action responsive to both the identity characteristic and the one or more analyte properties.

3. An apparatus as in claim 2, where the identity characteristic comprises verification or nonverification of the purported identity of the subject.

4. An apparatus as in claim 3, further comprising an identity input system comprising at least one of: an alphanumeric password entry device, a key input device, a magnetic swipe card reader, a GPS location device, a finger print reader, a voice recognition system, a retina scanner, bar code scanner, or an implanted sensor or material.

5. An apparatus as in claim 2, where the identity characteristic comprises determination of whether the individual is part of a predetermined group, without requiring the individual to indicate a purported identity.

6. An apparatus as in claim 5, where the authorized group consists of only one individual.

7. An apparatus as in claim 1, wherein the one or more analyte properties comprises the presence of alcohol or one or more alcohol byproducts in the individual; the concentration of alcohol or one or more alcohol byproducts in the individual; the presence of a substance of abuse in the individual; the concentration of a substance of abuse in the individual; or a combination of the preceding.

8. An apparatus as in claim 1, wherein the action initiation system is adapted to perform at least one of: communicate the one or more analyte properties to an agent associated with the controlled environment; record the one or more analyte properties; allow or disallow access to the controlled environment based on the one or more analyte properties; or communicate to an agent associated with the controlled environment the result of a comparison of the one or more analyte properties with predetermined values.

9. An apparatus as in claim 1, wherein the portion of the individual's tissue comprises at least one of: the finger, forearm, ear lobe, palm, lip, hand, or skin of the individual.

10. An apparatus as in claim 1, where the controlled environment or site is one of: a hospital, area of a hospital, surgical suite, prison, area of a prison, jail, health clinic, dental office, aircraft cockpit, airport terminal, area of an airport, automobile, a truck, a bus, parole office, probation office, court building, courtroom, home arrest location, residential treatment center, office building, warehouse, storage facility, office or offices within a building, factory, regions within a factory, construction site, sports facility, recreational facility, amusement park, school, school activity site, dormitory, restaurant, bar, club, day care facility, ship, military installation, roadside stop, traffic accident site, DUI checkpoint, train control room, train, research facilities, laboratories, maintenance facilities, classified facilities, air traffic control facility, security center, historic sites, parks, machine shop, dispatch office, dispatch center, garages, school bus facilities, a space from which alcohol is accessed, or a power plant.

11. An apparatus as in claim 1, wherein the analysis system is adapted to determine from the spectroscopic signal the presence of topical or chemical interferents.

12. An apparatus as in claim 1, wherein the analysis system determines the one or more analyte properties in part by correcting, filtering, or adjusting the spectroscopic signal for topical or chemical interferents.

13. An apparatus as in claim 1, wherein the spectroscopic system is adapted to determine the response of the portion of tissue at a single distribution of path lengths through the portion of tissue.

14. An apparatus as in claim 1, wherein the spectroscopic system is adapted to determine the response of the portion of tissue at a first distribution of path lengths through the tissue, and at a second distribution of path lengths through the tissue, wherein the second distribution of path lengths is different from the first distribution of path lengths.

15. An apparatus as in claim 1, wherein:
  a) the illumination/modulation subsystem comprises a plurality of light sources, wherein each light source emits light at a different narrow range of wavelengths, and a modulator for modulating the intensity of each of the light sources;
  b) the tissue sampling subsystem is adapted to introduce the light emitted by the illumination subsystem into the tissue of the subject and to collect an optical output signal comprising the portion of the light not absorbed by the tissue; and
  c) the data acquisition subsystem comprises a single element detector adapted to detect the optical output signal as a function of time.

16. An apparatus as in claim 1, wherein the illumination/modulation subsystem comprises at least one of a solid state light source, a light emitting diode, a vertical cavity surface emitting laser, or a quantum cascade laser.

17. An apparatus as in claim 1, wherein the illumination/modulation subsystem comprises a plurality of solid state light sources, each modulated in intensity at a frequency different from that of at least one other of said light sources, and with the output of the plurality of light sources optically combined into a single beam.

18. An apparatus as in claim 1 wherein the illumination/modulation subsystem comprises one or more solid state light sources, and electronic circuitry to control at least one of the drive current, the drive voltage, or the temperature of the solid state light source.

19. An apparatus as in claim 1, wherein the illumination/modulation subsystem comprises a plurality of solid state light sources, and a light homogenizer that accepts light from the solid state light sources and provide angular homogenization, spatial homogenization, or both, of the light.

20. An apparatus as in claim 1, wherein the illumination/modulation subsystem produces illumination light at a plurality of wavelengths, and wherein the illumination/modulation subsystem comprises an etalon with transmission peaks at wavelengths desired for the spectroscopic signal, or a dispersive grating configured to encode the wavelengths into separate spatial locations.

21. An apparatus as in claim 1, wherein the tissue sampling subsystem is adapted to communicate light with a hand of a subject.

22. An apparatus as in claim 1, wherein the tissue sampling subsystem is adapted to communicate light with the top of one or more fingers of a subject, between the first and second knuckles of said finger or fingers.

23. An apparatus as in claim 1, wherein the tissue sampling subsystem is adapted to communicate light multiple sample locations on the skin of a subject.

24. An apparatus as in claim 1, wherein the analysis system comprises a model relating spectroscopic signal to analyte property, and wherein the analysis system is adapted to modify the model responsive to spectroscopic signals acquired from individuals with presumed analyte properties.

25. An apparatus for monitoring compliance of an individual with requirements relating to the consumption of alcohol, comprising:
  a) a spectroscopic system adapted to determine a spectroscopic signal from the response of at least a portion of the individual's tissue to incident electromagnetic radiation, wherein the spectroscopic system comprises:
    i) an illumination/modulation subsystem;
    ii) a tissue sampling subsystem;
    iii) a data acquisition subsystem;
    iv) an analysis subsystem adapted to determine from the spectroscopic signal the presence, concentration, or both, of alcohol or an alcohol byproduct in the individual's tissue, and further adapted to determine an identity characteristic of the individual from the spectroscopic signal; and
    v) a calibration subsystem;
  b) an output system adapted to communicate a signal responsive to the determination of the analysis system.

26. An apparatus as in claim 25, wherein:
  a) the illumination/modulation subsystem comprises a plurality of light sources, wherein each light source emits light at different narrow range of wavelengths, and a modulator for modulating the intensity of each of the light sources;
  b) the tissue sampling subsystem is adapted to introduce the light emitted by the illumination subsystem into the tissue of the subject and to collect an optical output signal comprising the portion of the light not absorbed by the tissue; and
  c) the data acquisition subsystem comprises a single element detector adapted to detect the optical output signal as a function of time.

27. An apparatus as in claim 25, wherein the illumination/modulation subsystem comprises at least one of a solid state light source, a light emitting diode, a vertical cavity surface emitting laser, or a quantum cascade laser.

28. An apparatus as in claim 25, wherein the illumination/modulation subsystem comprises a plurality of solid state light sources, each modulated in intensity at a frequency different from that of at least one other of said light sources, and with the output of the plurality of light sources optically combined into a single beam.

29. An apparatus as in claim 25 wherein the illumination/modulation subsystem comprises one or more solid state light sources, and electronic circuitry to control at least one of the drive current, the drive voltage, or the temperature of the solid state light source.

30. An apparatus as in claim 25, wherein the illumination/modulation subsystem comprises a plurality of solid state light sources, and a light homogenizer that accepts light from the solid state light sources and provide angular homogenization, spatial homogenization, or both, of the light.

31. An apparatus as in claim 25, wherein the illumination/modulation subsystem produces illumination light at a plurality of wavelengths, and wherein the illumination/modulation subsystem comprises an etalon with transmission peaks at wavelengths desired for the spectroscopic signal, or a dispersive grating configured to encode the wavelengths into separate spatial locations.

32. A system for monitoring compliance with requirements related to alcohol or substance of abuse consumption, comprising a plurality of apparatuses as in claim 25 disposed in a plurality of locations remote from each other, with each such apparatus connected to a communication system, wherein each such apparatus is adapted to communicate to a remote monitor the identity and the alcohol status of an individual presenting to the apparatus.

33. A method of remotely monitoring compliance of a plurality of individuals with requirements related to alcohol consumption, comprising disposing a plurality of apparatuses as in claim 25 in a plurality of locations remote from each other, determining with one of such apparatuses the identity and alcohol status of an individual presenting to the apparatus, and communicating the determined identity and determined alcohol status to a remote monitor, and wherein each of the plurality of individuals can present to any of the plurality of apparatuses.

34. An apparatus as in claim 25, wherein the analysis system comprises a model relating spectroscopic signal to presence, concentration, or both, of alcohol or an alcohol byproduct in the individual's tissue, and wherein the analysis system is adapted to modify the model responsive to spectroscopic signals acquired from individuals with presumed zero presence or concentration of alcohol or an alcohol byproduct in the individual's tissue.

* * * * *